(12) United States Patent
Bonfanti et al.

(10) Patent No.: US 9,725,432 B2
(45) Date of Patent: Aug. 8, 2017

(54) PYRIMIDINE DERIVATIVES FOR THE TREATMENT OF BACTERIAL DISEASES

(71) Applicant: JANSSEN R&D IRELAND, Co Cork (IE)

(72) Inventors: Jean-Francois Bonfanti, Ande (FR); Philippe Muller, Ande (FR); Frederic Marc Maurice Doublet, Isneauville (FR); Jerome Michel Claude Fortin, Igoville (FR); Nacer Lounis, Beerse (BE)

(73) Assignee: Janssen Sciences Ireland US, Cork (IE)

(*) Notice: Subject to any disclaimer, the term of this patent is extended or adjusted under 35 U.S.C. 154(b) by 0 days.

(21) Appl. No.: 14/397,501

(22) PCT Filed: Apr. 30, 2013

(86) PCT No.: PCT/EP2013/058980
§ 371 (c)(1),
(2) Date: Oct. 28, 2014

(87) PCT Pub. No.: WO2013/164337
PCT Pub. Date: Nov. 7, 2013

(65) Prior Publication Data
US 2015/0087651 A1  Mar. 26, 2015

(30) Foreign Application Priority Data
Apr. 30, 2012  (EP) .................................. 12166140

(51) Int. Cl.
| | | |
|---|---|---|
| *A61K 31/497* | (2006.01) | |
| *C07D 401/04* | (2006.01) | |
| *C07D 405/14* | (2006.01) | |
| *C07D 403/04* | (2006.01) | |
| *C07D 239/26* | (2006.01) | |
| *C07D 239/42* | (2006.01) | |
| *C07D 409/14* | (2006.01) | |
| *A61K 31/506* | (2006.01) | |
| *A61K 45/06* | (2006.01) | |
| *C07D 401/14* | (2006.01) | |

(52) U.S. Cl.
CPC .......... *C07D 401/04* (2013.01); *A61K 31/506* (2013.01); *A61K 45/06* (2013.01); *C07D 239/26* (2013.01); *C07D 239/42* (2013.01); *C07D 401/14* (2013.01); *C07D 403/04* (2013.01); *C07D 405/14* (2013.01); *C07D 409/14* (2013.01)

(58) Field of Classification Search
USPC ..................... 514/252.18, 256; 544/333, 330
See application file for complete search history.

(56) References Cited

U.S. PATENT DOCUMENTS

| 6,887,870 B1* | 5/2005 | Ahmad et al. ............. 514/235.8 |
|---|---|---|
| 2005/0137216 A1* | 6/2005 | Ahmad et al. ............... 514/269 |
| 2005/0182073 A1 | 8/2005 | Gebauer et al. | |

FOREIGN PATENT DOCUMENTS

| JP | 2005-520821 | 7/2005 |
|---|---|---|
| JP | 2008-536950 | 9/2008 |
| WO | WO 01/27107 | 4/2001 |
| WO | WO 03/077656 | 9/2003 |
| WO | WO 03/077656 A1 | 9/2003 |
| WO | WO 2005/070899 A1 | 8/2005 |
| WO | WO 2006/113704 | 10/2006 |
| WO | WO 2009/095773 * | 8/2009 |
| WO | WO 2011/060976 A1 | 5/2011 |
| WO | WO 2011/061214 A1 | 5/2011 |
| WO | WO 2011/073378 A1 | 6/2011 |

OTHER PUBLICATIONS

Gabrielsen et al. CAS: 156: 247925, 2012.*
Ahmad et al. CAS: 134: 311218, 2001.*
European Search Report mailed Oct. 16, 2013 for corresponding Application No. PCT/EP2013/058980.
M. Gabrielsen et al., European Journal of Medicinal Chemistry 47 (2012) 24-37.
1069567-76-5/RN, STN on the Web, published on Nov. 2, 2008.
1065610-31-2/RN, STN on the Web, published on Oct. 24, 2008.
1060430-47-8/RN, STN on the Web, published on Oct. 13, 2008.
1060386-34-6/RN, STN on the Web, published on Oct. 13, 2008.
1060384-06-6/RN, STN on the Web, published on Oct. 13, 2008.
1060376-66-0/RN, STN on the Web, published on Oct. 13, 2008.

(Continued)

*Primary Examiner* — Rei-Tsang Shiao
(74) *Attorney, Agent, or Firm* — Thomas J. Dodd

(57) ABSTRACT

The present invention relates to novel compounds of formula I:

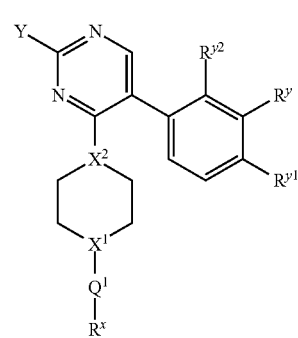

or a pharmaceutically acceptable salt thereof, wherein the integers are as defined in the description.
The claimed compounds are useful for the treatment of a bacterial infection. Also claimed is a composition comprising a pharmaceutically acceptable carrier and, as active ingredient, a therapeutically effective amount of the claimed compounds, the use of the claimed compounds or compositions for the manufacture of a medicament for the treatment of a bacterial infection and a process for preparing the claimed compounds.

4 Claims, No Drawings

(56) References Cited

OTHER PUBLICATIONS

CAS Registry No. 1065596-27-1, Entered STN Oct. 24, 2008.
CAS Registry No. 1069845-99-3, Entered STN Nov. 2, 2008.
CAS Registry No. 1070341-91-1, Entered STN Nov. 3, 2008.
CAS Registry No. 1070689-58-5, Entered STN Nov. 4, 2008.
CAS Registry No. 1070735-55-5, Entered STN Nov. 4, 2008.
CAS Registry No. 1070761-21-5, Entered STN Nov. 4, 2008.
Database chemcats [Online], Chemical Abstracts Service, Columbus, Ohio, US; Jan. 1, 2012 (Jan. 1, 2012), XP002682630, retrieved from STN, Amb11123585/ON, Amb10985987/ON, Amb11124074/ON, Amb11122037/ON, Amb11121846/ON, Amb10987155, Amb11123263/ON, Amb11125998/ON, Amb10985820/ON, Amb10986959/ON, 11129309/ON & Jan. 1, 2012 (Jan. 1, 2012), Ambinter Stock Screeining Collection.
CAS Registry No. 1070464-18-4.
CAS Registry No. 1070442-57-7.
CAS Registry No. 1069931-18-5.
CAS Registry No. 1069901-39-8.
CAS Registry No. 1069788-76-6.
CAS Registry No. 1069774-13-5.
CAS Registry No. 1069762-46-4.
CAS Registry No. 1069713-04-7.
CAS Registry No. 1069773-66-5, Entered STN Nov. 2, 2008.
CAS Registry No. 1069557-77-2, Entered STN Nov. 2, 2008.
Database Registry [Online]: Chemical Abstracts Service, Columbus, Ohio, USA. Retrieved from STN Registry No. 1069673-21-7, 1069667-19-1, 1069581-80-1, 1069557-77-2, 10649484-50-9, 1066992-98-0, 1065635-06-4.
Database Registry [Online]: Chemical Abstracts Service, Columbus, Ohio, USA. Retrieved from STN, Registry No. 1206793-33-0, 1185567-90-1, 1185479-09-7, 1185383-88-3, 1070761-21-5, 1070491-00-7, 1070464-42-4, 1070464-18-4, 1070456-25-5, 1070410-21-7, 1070361-37-3, 1070361-02-2, 1070357-11-7, 1070341-91-1, 1069949-30-9, 1069944-48-4, 1069925-90-1, 1069901-39-8, 1069900-50-0, 1069900-49-7, 1069845-99-3, 1069836-86-7, 1069799-91-2, 1069789-74-7' 1069788-76-6, 1069774-13-5, 1069773-66-5, 1069762-46-4, 1069758-76-4, 1069756-10-1, 1069753-56-5, 1069750-24-8, 1069738-47-1, 1069733-53-4, 1069731-54-9, 1069713-04-7' 1069694-85-4, 1069679-24-8, 1069667-29-3, 1069662-81-2, 1069662-26-5, 1069644-72-9, 1069644-54-7, 1069642-28-9, 1069634-79-2, 1069621-41-5, 1069618-39-8, 1069588-62-1, 1069587-36-5, 1069567-76-5, 1069554-39-7, 1069554-25-1, 1069588-62-1, 1069587-36-5, 1069567-76-5, 1069554-39-7, 1069554-25-1, 1069552-77-7, 1069540-90-4, 1069538-00-6, 1069531-70-9, 1069517-62-9, 1069516-16-0, 1069515-59-8, 1069515-33-8, 1069506-85-9, 1069504-61-5, 1069482-96-7, 1069481-08-8, 1067062-06-9, 1067054-23-2, 1066993-46-1, 1066983-40-1, 1066944-58-8, 1066919-16-1, 1066916-08-2, 1066892-19-0, 1066885-49-1, 1065630-42-3, 1065615-45-3, 1065610-31-2, 1065600-94-3, 1065593-01-2, 1065590-78-4, 1065584-38-4, 1065582-39-9, 1065552-33-1, 1065541-00-5, 1065512-19-7, 1065507-77-8, 1065494-19-0, 1061137-39-0, 1061135-53-2, 1061095-48-4, 1061075-37-3, 1061050-36-9, 1061048-76-7, 1061041-68-6, 1061036-71-2, 1060967-35-2, 1060951-24-7, 1060947-72-9, 1061041-68-6, 1061036-71-2, 1060967-35-2, 1060951-24-7, 1060947-72-9, 1060936-27-7, 1060930-54-2, 1060928-59-7, 1060536-06-2, 1060533-98-3, 1060528-95-1, 1060499-15-1, 1060478-50-3, 1060470-27-0, 1060465-54-4, 1060452-53-0, 1060431-54-0, 1060430-47-8, 1060429-55-1, 1060411-28-0, 1060406-86-1, 1060397-21-8, 1060392-62-2, 1060391-88-9, 1060386-99-3, 1060386-34-6, 1060384-06-6, 1060383-22-3.
CAS RN 1066919-16-1, STN Entry Date Oct. 27, 2008.
CAS RN 1069789-74-7, STN Entry Date Nov. 2, 2008.
CAS RN 1070342-60-7, STN Entry Date Nov. 3, 2008.
CAS RN 1060455-88-0, STN Entry Date Oct. 13, 2008.
CAS RN 1060928-59-7, STN Entry Date Oct. 14, 2008.

* cited by examiner

PYRIMIDINE DERIVATIVES FOR THE TREATMENT OF BACTERIAL DISEASES

CROSS-REFERENCE TO RELATED APPLICATIONS

The present application claims priority of the benefits of the filing of Application Nos. EP 12166140.9 filed Apr. 30, 2012, and PCT/EP2013/058980 (WO2013/164337 A9) filed Apr. 30, 2013. The complete disclosures of the aforementioned related patent applications are hereby incorporated herein by reference for all purposes.

The present invention relates to compounds useful for the treatment of a bacterial disease, in particular diseases caused by a certain non-*mycobacterium*, *Staphylococcus aureus*. The compounds may be useful in any mammal (e.g. human or animal). The invention also relates to novel compounds, compositions, processes and uses.

BACKGROUND OF THE INVENTION

Bacterial infections are prevalent in the world and there is a high need for compounds that treat bacterial infections. There are several known types/strains of bacteria that exist and it is a particular goal in the medical field to find compounds that are selectively active against certain types/strains of bacteria.

There are already several drugs known that have activity against non-mycobacteria, but there remains a need for such compounds, particularly because bacteria can gain resistance to certain compounds/drugs. Compounds that have selective activity against certain types/strains of bacteria will clearly be advantageous, for instance these compounds may have the advantage that the bacteria cannot build up resistance to other strains of bacteria.

Indeed, the purpose of the present invention is to provide compounds that have selective activity against a particular non-*mycobacterium*, specifically *Staphylococcus aureus*.

Certain pyrimidine compounds are publically available or have been disclosed via Chemical Abstracts Service, but such compounds have not had any particular use ascribed to them. International patent application WO 2005/070899 and US patent application US 2005/182073 both disclose certain pyrimidines that may be useful for controlling harmful organisms (for instance organisms that attack plants). International patent application WO 2003/077656 discloses certain pyrimidines that may be useful as antibacterials. These documents only disclose certain types of pyrimidines.

US patent U.S. Pat. No. 6,887,870 B1 discloses various compounds as sodium/proton exchange inhibitors, but does not disclose such compounds for use in the treatment of bacterial infections. International patent applications WO 2011/073378, WO 2011/060976 and WO 2011/061214 apparently disclose certain compounds for use as antibacterials, but these documents only disclose a limited range of compounds.

SUMMARY OF THE INVENTION

There is provided a compound of formula I for use as medicament/pharmaceutical, wherein formula I represents:

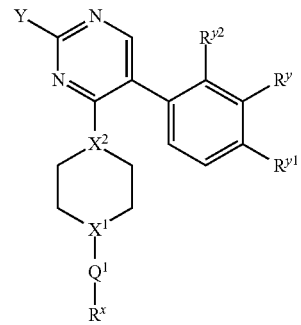

wherein:
Y represents:

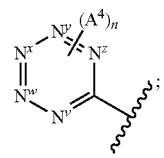

(ii) —$CF_3$;
(iii) —$N(C_{1-6}$ alkyl$)_2$ (e.g. —$N(CH_3)_2$); or
(iv) $C_{3-6}$ cycloalkyl (e.g. cyclopropyl);
$N^v$, $N^w$, $N^x$, $N^y$ and $N^z$ independently represent —N= or —C(H)= (or —$C(A^4)$=) but wherein only a maximum of three of $N^v$, $N^w$, $N^x$, $N^y$ and $N^z$ may represent —N=;
n represents 0, 1 or 2 (but preferably represents 0);
$X^1$ and $X^2$ independently represent —N— or —C(H)—;
when $X^1$ represents —N—, $Q^1$ represents a direct bond, —C(O)— or —$S(O)_2$—;
when $X^1$ represents —C(H)—, $Q^1$ represents a direct bond or —$N(R^z)$—;
$R^z$ represents hydrogen or $C_{1-6}$ alkyl;
$R^x$ represents $C_{1-6}$ alkyl (optionally substituted by one or more substituents selected from =O and $A^1$), aryl or heteroaryl (which latter two groups are each optionally substituted by one or more substituents selected from $A^2$ and $A^3$, respectively);
$R^y$, $R^{y1}$ and $R^{y2}$ independently represent hydrogen, halo, —CN, —$OR^{10}$, —$N(R^{11})(R^{12})$ or $C_{1-6}$ alkyl (optionally substituted by one or more halo (e.g. fluoro) atoms);
$A^1$, $A^2$, $A^3$ and $A^4$ independently represent halo, —CN, —$OR^1$, —$S(O)_{0-2}C_{1-3}$alkyl, $C_{1-6}$ alkyl (optionally substituted by one or more halo substituents), heterocyloalkyl (optionally substituted by one or more substituents selected from $C_{1-3}$ alkyl and halo), aryl or heteroaryl (which latter two groups are optionally substituted by one or more substituents selected from $B^1$ and $B^2$, respectively);
each $R^1$ and $R^{10}$ independently represent hydrogen, $C_{1-6}$ alkyl (optionally substituted by one or more halo substituents), aryl or heteroaryl (which latter two groups are optionally substituted by one or more substituents selected from halo, $C_{1-3}$ alkyl and —O—$C_{1-3}$ alkyl);
$R^{11}$ and $R^{12}$ independently represent hydrogen or $C_{1-6}$ alkyl;
$B^1$ and $B^2$ independently represent halo (e.g. chloro or fluoro), —CN, $C_{1-6}$ alkyl (optionally substituted by one or more halo (e.g. fluoro) atoms), —OH or —O—$C_{1-6}$ alkyl (optionally substituted by one or more halo (e.g. fluoro) atoms),
or a pharmaceutically acceptable salt thereof The above-mentioned compounds of formula I (which are useful as medicaments) may be referred to herein as "compounds of the invention".

The compounds of the invention that may be mentioned include those as hereinbefore defined but:

(a) with the proviso that the compound is not:

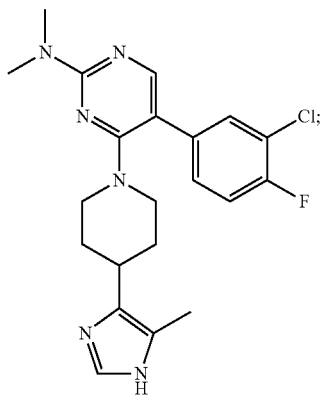 [SMILES: Cc1[nH]cnc1C1CCN(c2nc(N(C)C)ncc2-c2ccc(F)c(Cl)c2)CC1]

or (b) wherein Y represents:

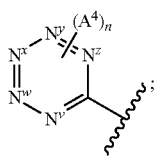

(ii) —CF$_3$; or (iii) C$_{3-6}$ cycloalkyl (e.g. cyclopropyl).

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

For the purposes of this invention solvates, prodrugs, N-oxides and stereoisomers of compounds of the invention are also included within the scope of the invention.

The term "prodrug" of a relevant compound of the invention includes any compound that, following oral or parenteral administration, is metabolised in vivo to form that compound in an experimentally-detectable amount, and within a predetermined time (e.g. within a dosing interval of between 6 and 24 hours (i.e. once to four times daily)).

For the avoidance of doubt, the term "parenteral" administration includes all forms of administration other than oral administration.

Prodrugs of compounds of the invention may be prepared by modifying functional groups present on the compound in such a way that the modifications are cleaved, in vivo when such prodrug is administered to a mammalian subject. The modifications typically are achieved by synthesising the parent compound with a prodrug substituent. Prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. 1-92, Elesevier, New York-Oxford (1985).

Compounds of the invention may contain double bonds and may thus exist as E (entgegen) and Z (zusammen) geometric isomers about each individual double bond. Positional isomers may also be embraced by the compounds of the invention. All such isomers (e.g. if a compound of the invention incorporates a double bond or a fused ring, the cis- and trans-forms, are embraced) and mixtures thereof are included within the scope of the invention (e.g. single positional isomers and mixtures of positional isomers may be included within the scope of the invention).

Compounds of the invention may also exhibit tautomerism. All tautomeric forms (or tautomers) and mixtures thereof are included within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganisation of some of the bonding electrons.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person.

All stereoisomers (including but not limited to diastereoisomers, enantiomers and atropisomers) and mixtures thereof (e.g. racemic mixtures) are included within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{123}I$, and $^{125}I$. Certain isotopically-labeled compounds of the present invention (e.g., those labeled with $^{3}H$ and $^{14}C$) are useful in compound and for substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$ may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Scheme 1 and/or in the Examples herein below, by substituting an isotopically labeled reagent for a non-isotopically labeled reagent.

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). Such cycloalkyl groups may be monocyclic or bicyclic and may further be bridged. Further, when there is a sufficient number (i.e. a minimum of four) of carbon atoms, such groups may also be part cyclic. Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group).

$C_{3-q}$ cycloalkyl groups (where q is the upper limit of the range) that may be specifically mentioned may be monocyclic or bicyclic alkyl groups, which cycloalkyl groups may further be bridged (so forming, for example, fused ring systems such as three fused cycloalkyl groups). Such cycloalkyl groups may be saturated or unsaturated containing one or more double bonds (forming for example a cycloalkenyl group). Substituents may be attached at any point on the cycloalkyl group. Further, where there is a sufficient number (i e a minimum of four) such cycloalkyl groups may also be part cyclic.

The term "halo", when used herein, preferably includes fluoro, chloro, bromo and iodo.

Heterocycloalkyl groups that may be mentioned include non-aromatic monocyclic and bicyclic heterocycloalkyl groups in which at least one (e.g. one to four) of the atoms in the ring system is other than carbon (i.e. a heteroatom), and in which the total number of atoms in the ring system is between 3 and 20 (e.g. between three and ten, e.g between 3 and 8, such as 5- to 8-). Such heterocycloalkyl groups may also be bridged. Further, such heterocycloalkyl groups may be saturated or unsaturated containing one or more double and/or triple bonds, forming for example a $C_{2-q}$ heterocycloalkenyl (where q is the upper limit of the range) group. $C_{2-q}$ heterocycloalkyl groups that may be mentioned include 7-azabicyclo[2.2.1]heptanyl, 6-azabicyclo[3.1.1]heptanyl, 6-azabicyclo[3.2.1]-octanyl, 8-azabicyclo-[3.2.1]octanyl, aziridinyl, azetidinyl, dihydro-pyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo-[3.2.1]octanyl, oxetanyl, oxiranyl, piperazinyl, piperidinyl, non-aromatic pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form. Heterocycloalkyl mentioned herein may be stated to be specifically monocyclic or bicyclic.

Aryl groups that may be mentioned include $C_{6-20}$, such as $C_{6-12}$ (e.g. $C_{6-10}$) aryl groups. Such groups may be monocyclic, bicyclic or tricyclic and have between 6 and 12 (e.g. 6 and 10) ring carbon atoms, in which at least one ring is aromatic. $C_{6-10}$ aryl groups include phenyl, naphthyl and the like, such as 1,2,3,4-tetrahydronaphthyl. The point of attachment of aryl groups may be via any atom of the ring system. For example, when the aryl group is polycyclic the point of attachment may be via atom including an atom of a non-aromatic ring. However, when aryl groups are polycyclic (e.g. bicyclic or tricyclic), they are preferably linked to the rest of the molecule via an aromatic ring.

Unless otherwise specified, the term "heteroaryl" when used herein refers to an aromatic group containing one or more heteroatom(s) (e.g. one to four heteroatoms) preferably selected from N, O and S. Heteroaryl groups include those which have between 5 and 20 members (e.g. between 5 and 10) and may be monocyclic, bicyclic or tricyclic, provided that at least one of the rings is aromatic (so forming, for example, a mono-, bi-, or tricyclic heteroaromatic group). When the heteroaryl group is polycyclic the point of attachment may be via any atom including an atom of a non-aromatic ring. However, when heteroaryl groups are polycyclic (e.g. bicyclic or tricyclic), they are preferably linked to the rest of the molecule via an aromatic ring. Heteroaryl groups that may be mentioned include 3,4-dihydro-1H-isoquinolinyl, 1,3-dihydroisoindolyl, 1,3-dihydroisoindolyl (e.g. 3,4-dihydro-1H-isoquinolin-2-yl, 1,3-dihydroisoindol-2-yl, 1,3-dihydroisoindol-2-yl; i.e. heteroaryl groups that are linked via a non-aromatic ring), or, preferably, acridinyl, benzimidazolyl, benzodioxanyl, benzodioxepinyl, benzodioxolyl (including 1,3-benzodioxolyl), benzofuranyl, benzofurazanyl, benzothiadiazolyl (including 2,1,3-benzothiadiazolyl), benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazolyl, isothiochromanyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N- or S-oxidised form. Heteroaryl groups mentioned herein may be stated to be specifically monocyclic or bicyclic. When heteroaryl groups are polycyclic in which there is a non-aromatic ring present, then that non-aromatic ring may be substituted by one or more =O group.

It may be specifically stated that the heteroaryl group is monocyclic or bicyclic. In the case where it is specified that the heteroaryl is bicyclic, then it may consist of a five-, six- or seven-membered monocyclic ring (e.g. a monocyclic heteroaryl ring) fused with another five-, six- or seven-membered ring (e.g. a monocyclic aryl or heteroaryl ring).

Heteroatoms that may be mentioned include phosphorus, silicon, boron and, preferably, oxygen, nitrogen and sulfur.

For the avoidance of doubt, where it is stated herein that a group (e.g. a $C_{1-6}$ alkyl group) may be substituted by one or more substituents (e.g. selected from $A^1$), then those substituents (e.g. defined by $A^1$) are independent of one another. That is, such groups may be substituted with the same substituent (e.g. defined by $A^1$) or different substituents (defined by $A^1$).

All individual features (e.g. preferred features) mentioned herein may be taken in isolation or in combination with any other feature (including preferred feature) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

Compounds of the invention that may be mentioned include those in which there is provided a compound of formula I as defined herein but:
provided that when Y represents 2-chloro-phenyl, $R^{y1}$ represents —OCH$_2$CH$_3$, $R^y$ and $R^{y2}$ both represent hydrogen, $X^1$ and $X^2$ both represent N, $Q^1$ represents a direct bond, then $R^x$ does not represent —C(O)O-tert-butyl.

Preferred compounds of the invention will now be described.

Preferred compounds of the invention include those in which:
-$Q^1$-$R^x$ does not represent —CH$_3$;
for instance, when X represents —N—, and $Q^1$ represents a direct bond, and $R^x$ represents alkyl, then, it preferably represents $C_{2-6}$ (e.g. $C_{3-6}$) alkyl (optionally substituted by one or more substituents selected from =O and $A^1$);
when X represents —N— and $Q^1$ represents a direct bond, then $R^x$ preferably represents $C_{2-6}$ (e.g. $C_{3-6}$) alkyl (optionally substituted by one or more substituents selected from =O and $A^1$), aryl or heteroaryl (which latter two groups are optionally substituted by one or more substituents selected from $A^2$ and $A^3$, respectively);
when $R^x$ represents alkyl, then it preferably represents $C_{2-6}$ (e.g. $C_{3-6}$) alkyl (optionally substituted by one or more substituents selected from =O and $A^1$).

Preferred compounds of the invention include those in which:
the following substructure of formula I:

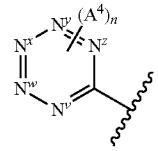

is one in which, preferably:
none, one or two of $N^v$, $N^w$, $N^x$, $N^y$ and $N^z$ (preferably one, $N^x$ or $N^y$) represents —N= and the others represent —C(H)= or, e.g. in the case when the above ring represents phenyl, one of $N^v$, $N^w$, $N^x$, $N^y$ and $N^z$ represents —C($A^4$)=;
when two of $N^v$, $N^w$, $N^x$, $N^y$ and $N^z$ represent —N=, then it is preferably $N^w$ and $N^y$ (so forming a 5-pyrimidinyl group);
n represents 0, 1 or 2 (but preferably represents 0);
$A^4$ (which may be present on any of the carbon atoms of the aromatic ring, including when $N^x/N^y/N^z$ represents —C(H)=) represents halo (e.g. fluoro or bromo), —CN, —OC$_{1-3}$ alkyl (e.g. —OCH$_3$), —S(O)$_2$C$_{1-3}$alkyl, or C$_{1-3}$ alkyl (optionally containing an unsaturation, so forming e.g. —C≡C), although $A^4$ is preferably not present; more preferably, the above sub-structure represents pyrimidinyl or pyridyl (preferably, pyridyl), optionally substituted by one or more substituents selected from $A^4$; most preferably, the above sub-structure represents pyridyl (preferably unsubstituted pyridyl, e.g. 2-pyridyl or, preferably, 3-pyridyl or 4-pyridyl) or substituted phenyl.

In one embodiment of the invention:
Y represents the $N^v$ to $N^z$-ring as defined herein (this is the most preferred).

In another embodiment of the invention:
Y represents —N(C$_{1-6}$ alkyl)$_2$ (e.g. —N(CH$_3$)$_2$).

In another embodiment of the invention:
Y represents C$_{3-6}$ cycloalkyl (e.g. cyclopropyl).

In another embodiment of the invention:
Y represents —CF$_3$.

More preferred compounds of the invention include those in which:
when $X^1$ represents —N—, $Q^1$ represents a direct bond;
$X^2$ represents —C(H)— and $X^1$ represents —N— (so forming a 4-piperidinyl group);
$X^2$ represents —N— and $X^1$ represents —C(H)— (so forming a 1-piperidinyl group);
$X^1$ and $X^2$ represent —N—, so forming a piperazinyl group.

Further preferred compounds of the invention include those in which:
$A^1$ represents heterocycloalkyl (e.g. oxetanyl) or, more preferably, $A^1$ represents halo (e.g. fluoro), —CN, C$_{1-6}$ alkyl (e.g. C$_{3-6}$ cycloalkyl), aryl (optionally substituted by one or more (e.g. one) substituent(s) selected from $B^1$), heteroaryl (optionally substituted by one or more (e.g. one) substituent(s) selected from $B^2$) or —OR$^1$;
when $A^1$ represents aryl, then it is preferably phenyl optionally substituted by one or more (e.g. one or two) substituent(s) selected from $B^1$;
when $A^1$ represents aryl substituted by one or more (e.g. one) $B^1$ substituent(s), then there is at least one substituent located at the meta-position of the phenyl group (and in total, there is preferably one or two $B^1$ substituents);

when $A^1$ represents optionally substituted heteroaryl, it is preferably a 5- or 6-membered heteroaryl group preferably containing one, two or three (e.g. one) heteroatom(s) preferably selected from nitrogen, sulfur and oxygen (e.g. sulfur and/or oxygen), so forming e.g. a thienyl (e.g. 2-thienyl or 3-thienyl) or a furanyl (e.g. 2-furanyl) group;

when $A^1$ represents optionally substituted heteroaryl, then it is optionally substituted by one or two (e.g. one) substituent(s) selected from $B^2$;

when $A^1$ represents $C_{3-6}$ cycloalkyl, then it is preferably cyclohexyl;

$B^1$ represents halo (e.g. fluoro or chloro), —CN, —OH or $C_{1-3}$ alkyl (methyl; optionally substituted by one or more halo, e.g. fluoro, atoms, so forming e.g. a —$CF_3$ group);

$B^2$ preferably represents $C_{1-4}$ alkyl (e.g. $C_{1-2}$ alkyl such as methyl);

$A^1$ represents halo (e.g. fluoro), —CN, thienyl (e.g. 2- or 3-thienyl, such as 3-methyl, 2-thienyl or unsubstituted 3-thienyl), furanyl (e.g. 2-furanyl), $C_{3-6}$ cycloalkyl (e.g. cyclohexyl) or —O-phenyl;

$R^1$ represents aryl (e.g. unsubstituted phenyl);

when $Q^1$ represents —$N(R^z)$—, then $R^x$ represents $C_{1-6}$ alkyl (optionally substituted by one or more substituents selected from =O and $A^1$), so forming e.g. —C(O)—C(H)(CH$_3$)—O-phenyl;

$R^z$ represents hydrogen;

when $Q^1$ represents a direct bond or —C(O)—, then $R^x$ preferably represents:

$C_{1-6}$ alkyl (e.g. acyclic $C_{1-6}$ alkyl or $C_{3-6}$ cycloalkyl) optionally substituted by one or more substituents selected from =O and/or $A^1$, and optionally containing one or more (e.g. one) double bond (so forming a $C_{2-6}$ alkenyl group) or triple bond (so forming a $C_{2-6}$ alkynyl group), so forming e.g. —CH$_2$—C(CH$_3$)$_3$, —CH$_2$CH(CH$_3$)$_2$, cyclopropyl, —CH$_2$—CF$_3$, —CH$_2$—C(H)F$_2$, —CH$_2$C(CH$_3$)$_2$—CN, —C(O)—C(CH$_3$)$_3$, —CH$_2$—CF$_2$CH$_3$, —CH$_2$-[3-methyl, 2-thienyl], —CH$_2$—C(CH$_3$)=CHCH$_3$, —CH$_2$-[3-fluorophenyl], —CH$_2$-[3-thienyl], —CH$_2$-[3-chloro-6-OH-phenyl], —CH$_2$-[3-hydroxyphenyl], —CH$_2$-[2-hydroxyphenyl], —CH$_2$-[2-hydroxy-4-chloro-phenyl], —CH$_2$-[2-hydroxy-5-chlorophenyl], —CH$_2$-phenyl, —CH$_2$-cyclohexyl, —CH$_2$-[2-thienyl], —CH$_2$[2-furanyl], —C(O)—C(H)(CH$_3$)—O-phenyl, —CH$_2$—C(H)(CH$_3$)$_2$, -cyclopropyl, —CH$_2$-[4-fluorophenyl], —C(O)—C(CH$_3$)$_3$, —CH$_2$-(3-trifluoromethyl-phenyl), —CH$_2$-(3-cyanophenyl), —CH$_2$-(4-cyanophenyl), —CH$_2$-(2,4-difluorophenyl), —CH$_2$-(3-methylphenyl), —CH$_2$-(4-methylphenyl), —CH$_2$-(2-fluorophenyl), —CH$_2$-(2-cyanophenyl), —CH$_2$-(3,4-difluorophenyl), —CH$_2$-(4-chlorophenyl), —CH$_2$-(3-chlorophenyl), —CH$_2$-(2-trifluoromethyl-phenyl), —CH$_2$-(2,6-difluorophenyl), —CH$_2$-(3,5-difluorophenyl), —CH$_2$—C≡CH or —CH$_2$—C(CH$_2$)(3-oxetanyl) (most preferably, $R^x$ represents —CH$_2$—C(CH$_3$)$_3$, —CH$_2$—CF$_3$, —CH$_2$—C(H)F$_2$, —CH$_2$C(CH$_3$)$_2$—CN, —C(O)—C(CH$_3$)$_3$ or —CH$_2$—CF$_2$CH$_3$); or $R^x$ represents aryl (e.g. phenyl) optionally substituted by one or more (e.g. one or two) substituents selected from $A^2$, so forming for e.g. unsubstituted phenyl;

$R^{10}$ represents $C_{1-4}$ alkyl (e.g. $C_{1-2}$ alkyl, such as methyl);

$R^{11}$ and $R^{12}$ independently represent hydrogen or, preferably, $C_{1-3}$ alkyl (e.g. methyl); either all of $R^y$, $R^{y1}$ and $R^{y2}$ represent hydrogen or, more preferably, at least one of $R^y$, $R^{y1}$ and $R^{y2}$ (preferably $R^y$) represents a substituent other than hydrogen and the others (preferably $R^{y1}$ and $R^{y2}$) represents hydrogen (i.e. there is preferably one substituent present on the phenyl ring, preferably in the meta-position);

when one of $R^y$, $R^{y1}$ and $R^{y2}$ (e.g. $R^y$) represents a substituent, then it is preferably selected from halo, —OCH$_3$, —N(CH$_3$)$_2$, —CN or $C_{1-3}$ alkyl optionally substituted by one or more fluoro atoms;

$R^y$ represents hydrogen or, preferably, halo (e.g. fluoro or, preferably, chloro), —OCH$_3$, —N(CH$_3$)$_2$, —CN or $C_{1-3}$ alkyl (e.g. —CH$_3$) optionally substituted by one or more fluoro atoms (e.g. —CF$_3$), and most preferably, $R^y$ represents —OCH$_3$ or —CN;

$R^{y1}$ represents hydrogen, or, when $R^y$ represents hydrogen, may represent a substituent selected from —OCH$_3$ and $C_{1-3}$ alkyl (e.g. methyl);

$R^{y2}$ represents hydrogen, or, when $R^y$ and $R^{y1}$ represent hydrogen, may represent a substituent selected from halo (e.g. fluoro) and $C_{1-3}$ alkyl (e.g. methyl);

$R^1$ represents hydrogen;

$A^2$ and $A^3$ independently represent halo (e.g. chloro) or —$OR^1$ (e.g. —OH).

Certain compounds of the invention disclosed herein may be novel per se. And hence in a further embodiment of the invention, there is provided a compound of formula I:

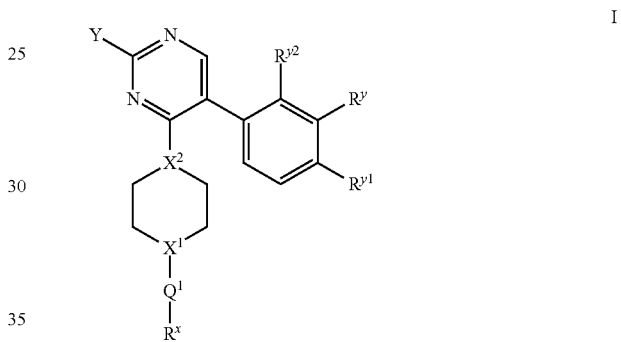

but wherein:
Y represents:

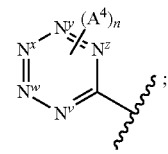

none or one of $N^v$, $N^w$, $N^x$, $N^y$ and $N^z$ (preferably one, e.g. $N^x$ or $N^y$) represent(s) —N= and the others represent —C(H)=;

n represents 0 or 1;

$X^1$ and $X^2$ independently represent —N— or —C(H)—;

when $X^1$ represents —N—, $Q^1$ represents a direct bond;

when $X^1$ represents —C(H)—, $Q^1$ represents a direct bond or —N($R^z$)—;

$R^z$ represents hydrogen or $C_{1-6}$ alkyl;

$R^x$ represents $C_{1-6}$ alkyl (optionally substituted by one or more substituents selected from =O and $A^1$), aryl or heteroaryl (which latter two groups are each optionally substituted by one or more substituents selected from $A^2$ and $A^3$, respectively);

$R^y$, $R^{y1}$ and $R^{y2}$ independently represent hydrogen, halo, —CN, —$OR^{10}$, —$N(R^{11})(R^{12})$ or $C_{1-6}$ alkyl (optionally substituted by one or more halo (e.g. fluoro) atoms);

$A^1$, $A^2$, $A^3$ and $A^4$ independently represent halo, —CN, —$OR^1$, —$S(O)_{0-2}C_{1-3}$alkyl, $C_{1-6}$ alkyl (optionally substituted by one or more halo substituents), heterocycloalkyl (optionally substituted by one or more substituents selected from $C_{1-3}$ alkyl and halo), aryl or heteroaryl (which latter two groups are optionally substituted by one or more substituents selected from $B^1$ and $B^2$, respectively);

each $R^1$ and $R^{10}$ independently represent hydrogen, $C_{1-6}$ alkyl (optionally substituted by one or more halo substituents), aryl or heteroaryl (which latter two groups are optionally substituted by one or more substituents selected from halo, $C_{1-3}$ alkyl and —O—$C_{1-3}$ alkyl);

$R^{11}$ and $R^{12}$ independently represent hydrogen or $C_{1-6}$ alkyl;

$B^1$ and $B^2$ independently represent halo (e.g. chloro or fluoro), —CN, $C_{1-6}$ alkyl (optionally substituted by one or more halo (e.g. fluoro) atoms), —OH or —O—$C_{1-6}$ alkyl (optionally substituted by one or more halo (e.g. fluoro) atoms), or a pharmaceutically acceptable salt thereof, with the proviso that the compound is not:

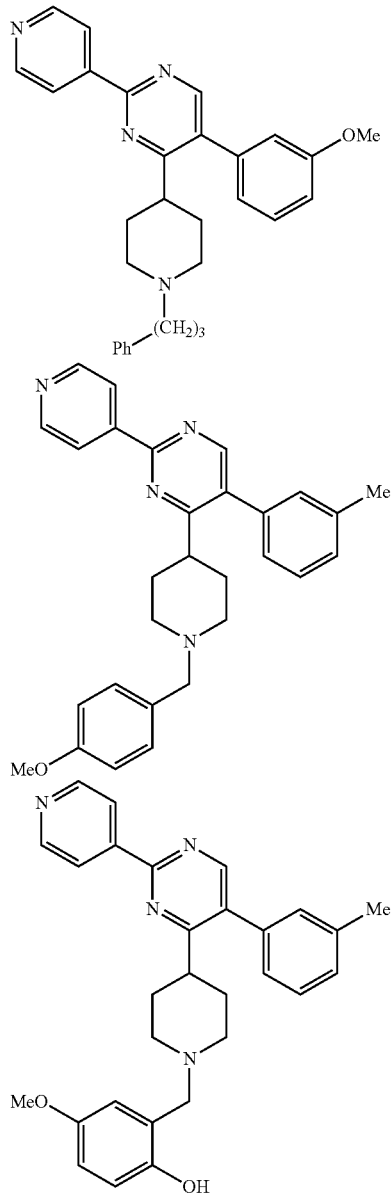

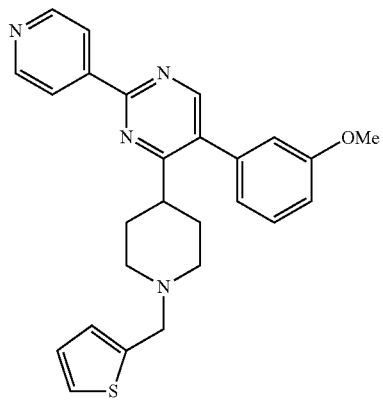

Preferred novel compounds of the invention in accordance with this further aspect of the invention may be those mentioned hereinbefore but in which:

$X^1$ represents —N—;

$X^2$ represent —C(H)—;

$R^x$ represents $C_{1-6}$ alkyl (optionally substituted by one or more substituents selected from =O and $A^1$);

$A^4$ (which is preferably present on a carbon atom of the phenyl ring, and is preferably in the para-position) represents halo (e.g. fluoro), —CN or —$OC_{1-3}$ alkyl (e.g. —$OCH_3$); $A^1$ represents halo (e.g. fluoro), —CN, $C_{1-6}$ alkyl or —$OR^1$;

either all of $R^y$, $R^{y1}$ and $R^{y2}$ represent hydrogen or, more preferably, at least one of $R^y$, $R^{y1}$ and $R^{y2}$ (preferably $R^y$) represents a substituent other than hydrogen and the others (preferably $R^{y1}$ and $R^{y2}$) represents hydrogen (i.e. there is preferably one substituent present on the phenyl ring, preferably in the meta-position);

when $R^y$ is other than hydrogen, it preferably represents halo (e.g. chloro), —$OCH_3$ or —CN; and/or $R^1$ represents hydrogen.

In particular, preferred novel compounds of the invention may be the following:

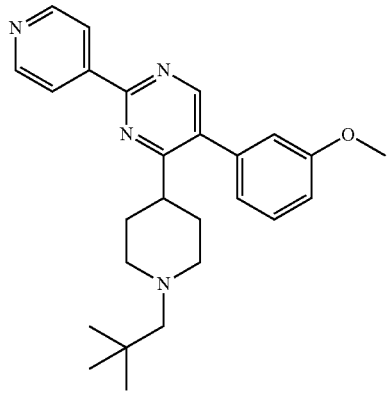 or

-continued

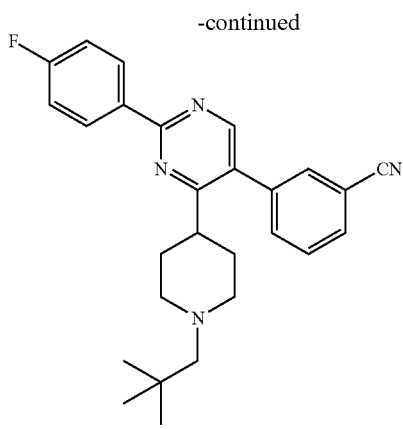

or a pharmaceutically acceptable salt thereof
Pharmacology

The compounds according to the invention have surprisingly been shown to be suitable for the treatment of a certain non-mycobacterial infection, specifically *Staphylococcus aureus*. They are therefore useful as medicaments/pharmaceuticals.

Further, the present invention also relates to the use of the compounds of the invention, the pharmaceutically acceptable salts thereof or the N-oxide forms thereof, as well as any of the pharmaceutical compositions thereof as described hereinafter, for the manufacture of a medicament for the treatment of a certain non-mycobacterial infection, specifically *Staphylococcus aureus*.

Accordingly, in another aspect, the invention provides a method of treating a patient suffering from, or at risk of, a certain non-mycobacterial infection, specifically *Staphylococcus aureus*, which comprises administering to the patient a therapeutically effective amount of a compound or pharmaceutical composition according to the invention.

Compounds of the invention have not only been shown to be suitable for the treatment of a certain non-*mycobaterium*, *Staphylococcus aureus*, but have been shown to selective activity against it. Hence, where "treatment" of a certain non-*mycobacterium* is referred to herein, it preferably means "selective treatment", for instance it has activity against that bacterium (*Staphylococcus aureus*) but may have no or minimal (or less) activity against other bacteria. This may be advantageous as, if the compound/drug is only selective against *Staphylococcus aureus*, then resistance to other strains cannot be built up and the need for unnecessary antibacterial action is prevented.

Bacterial infections which may be treated by the present compounds include, for example, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynaecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients.

Whenever used hereinbefore or hereinafter, that the compounds can treat a bacterial infection it is meant that the compounds can treat an infection with a certain non-mycobacterial infection, specifically *Staphylococcus aureus*.

The invention also relates to a composition comprising a pharmaceutically acceptable carrier and, as active ingredient, a therapeutically effective amount of a compound according to the invention. The compounds according to the invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight, even more preferably from 0.1 to 50% by weight of the active ingredient(s), and, from 1 to 99.95% by weight, more preferably from 30 to 99.9 by weight %, even more preferably from 50 to 99.9 by weight % of a pharmaceutically acceptable carrier, all percentages being based on the total composition.

The pharmaceutical composition may additionally contain various other ingredients known in the art, for example, a lubricant, stabilising agent, buffering agent, emulsifying agent, viscosity-regulating agent, surfactant, preservative, flavouring or colorant.

It is especially advantageous to formulate the aforementioned pharmaceutical compositions in unit dosage form for ease of administration and uniformity of dosage.

Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. The daily dosage of the compound according to the invention will, of course, vary with the compound employed, the mode of administration, the treatment desired and the mycobacterial disease indicated. However, in general, satisfactory results will be obtained when the compound according to the invention is administered at a daily dosage not exceeding 1 gram, e.g. in the range from 10 to 50 mg/kg body weight.

Given the fact that the compounds of the invention are active against bacterial infections (e.g. a certain type as defined herein), the present compounds may be combined with other antibacterial agents in order to effectively combat bacterial infections.

Therefore, the present invention also relates to a combination of (a) a compound according to the invention, and (b) one or more other antibacterial agents.

The present invention also relates to a combination of (a) a compound according to the invention, and (b) one or more other antibacterial agents, for use as a medicine.

The present invention also relates to the use of a combination or pharmaceutical composition as defined directly above for the treatment (e.g. selective treatment) of a bacterial infection (e.g. a certain type as defined herein, *Staphylococcus aureus*).

A pharmaceutical composition comprising a pharmaceutically acceptable carrier and, as active ingredient, a therapeutically effective amount of (a) a compound according to the invention, and (b) one or more other antibacterial agents, is also comprised by the present invention, particularly for use in the treatment of a certain bacterial infection as defined herein.

The weight ratio of (a) the compound according to the invention and (b) the other antibacterial agent(s) when given as a combination may be determined by the person skilled in the art. Said ratio and the exact dosage and frequency of administration depends on the particular compound according to the invention and the other antibacterial agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (Ia) or (Ib) and another antibacterial agent may range from 1/10 to 10/1, more in particular from 1/5 to 5/1, even more in particular from 1/3 to 3/1.

The compounds according to the invention and the one or more other antibacterial agents may be combined in a single preparation or they may be formulated in separate preparations so that they can be administered simultaneously, separately or sequentially. Thus, the present invention also relates to a product containing (a) a compound according to the invention, and (b) one or more other antibacterial agents, as a combined preparation for simultaneous, separate or sequential use in the treatment of a bacterial infection.

General Preparation

The compounds according to the invention can generally be prepared by a succession of steps, each of which is known to the skilled person and/or described below in the following General Schemes:

General scheme 1:

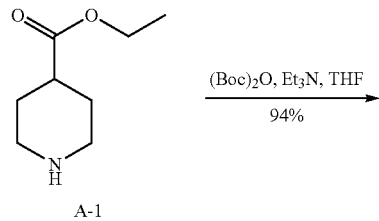

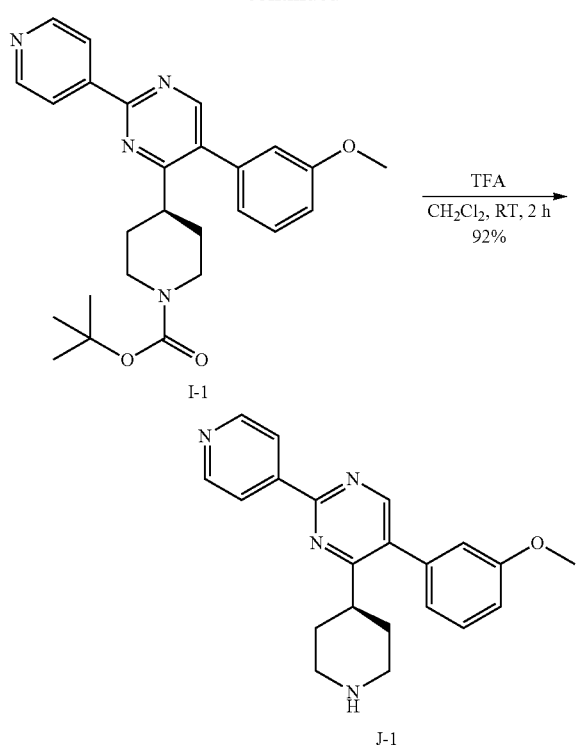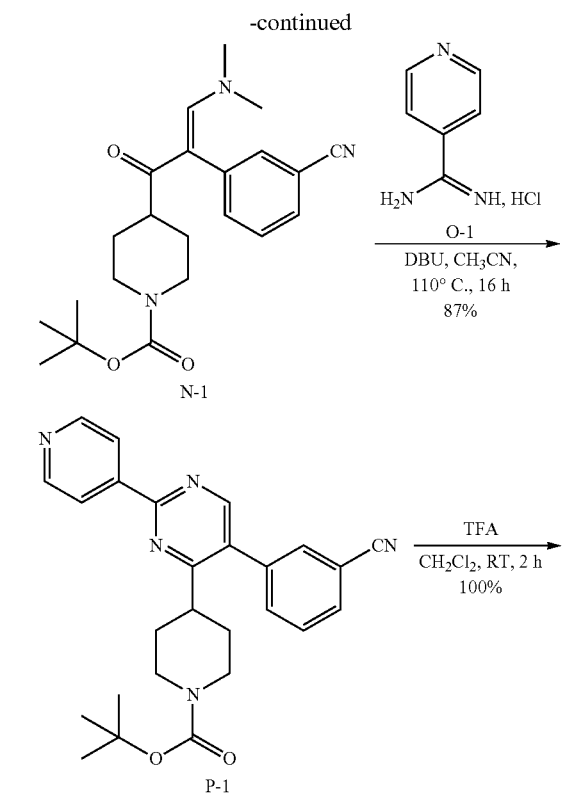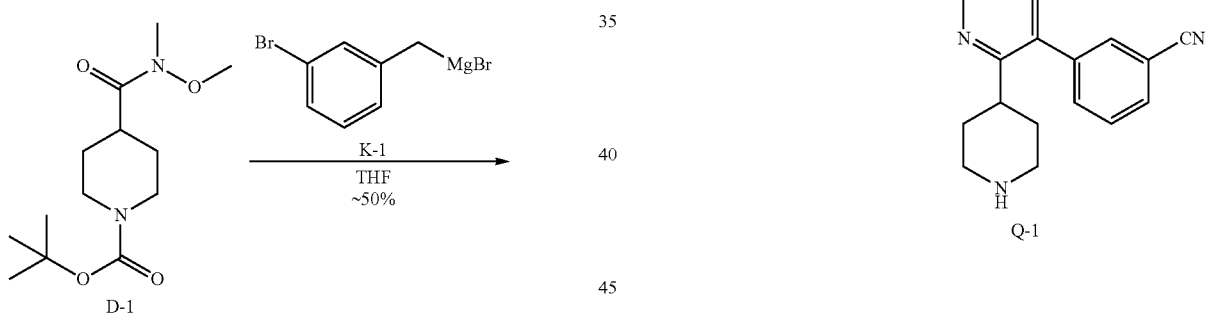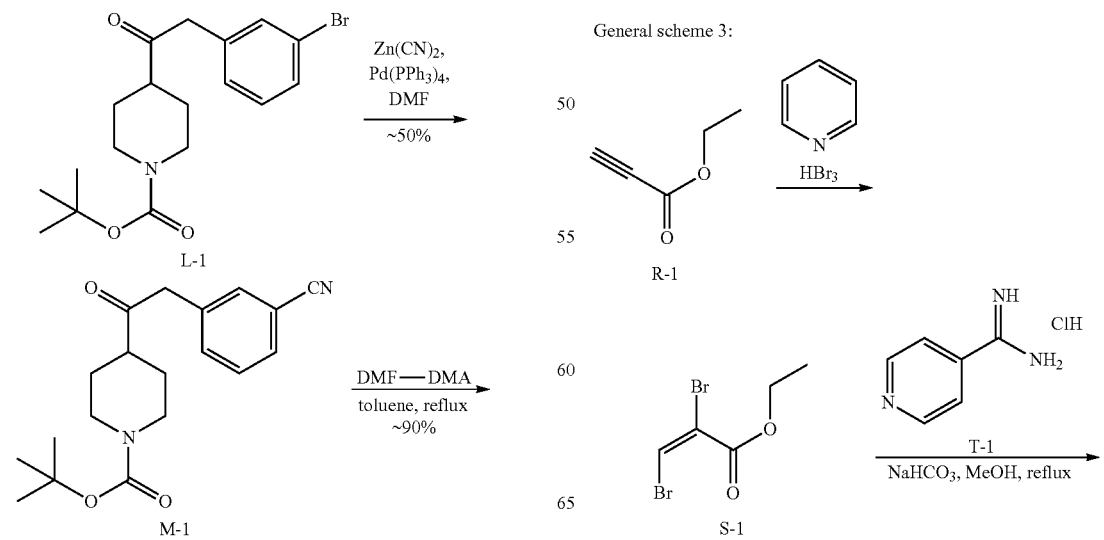

-continued

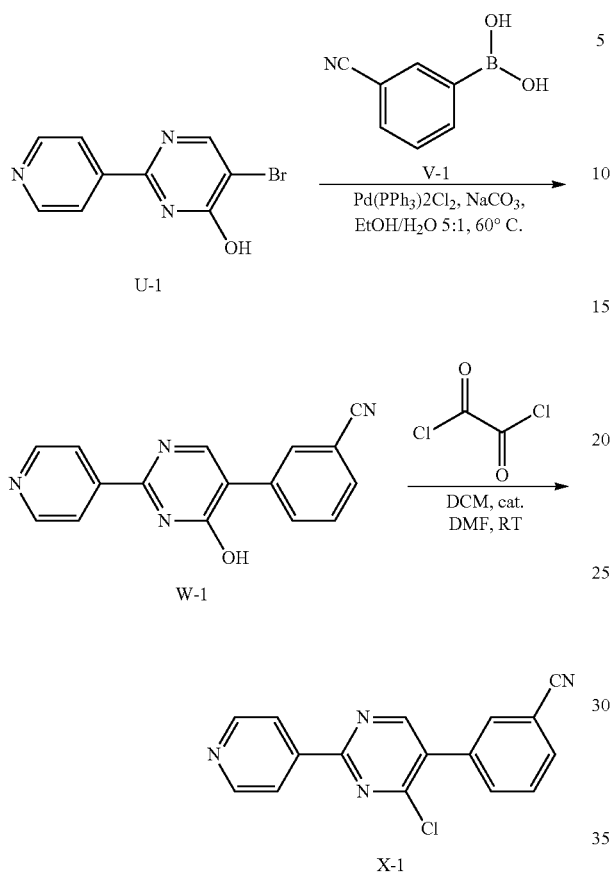

It is considered within the knowledge of the skilled man to explore the appropriate temperatures, dilutions, and reaction times in order to optimize the above reactions in order to obtain a desired compound.

The compounds of formula I may be converted to the corresponding N-oxide forms following art-known procedures for converting a trivalent nitrogen into its N-oxide form. Said N-oxidation reaction may generally be carried out by reacting the starting material of formula I with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarbo-peroxoic acid, peroxoalkanoic acids, e.g. peroxoacetic acid, alkylhydroperoxides, e.g. tert.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

For instance, compounds of formula I in which Y represents the $N^v$ to $N^z$-containing ring may be prepared by the following methods:

(i) For compounds of formula I in which $X^1$ represents —N—, reaction of a compound of formula II,

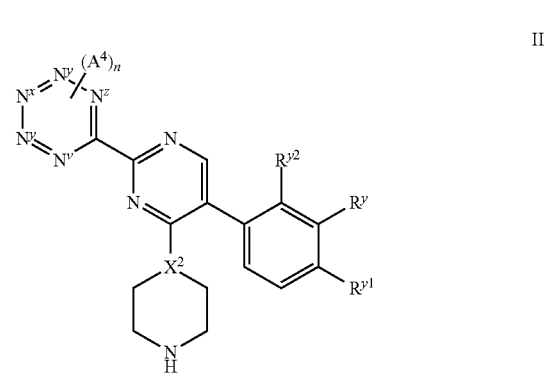

wherein $N^v$, $N^w$, $N^x$, $N^y$, $N^z$, $X^2$, $R^y$, $R^{y1}$, $R^{y2}$, $A^4$ and n are as hereinbefore defined, with:
(a) a compound of formula III,

wherein $L^1$ represents a suitable leaving group, such as chloro, bromo, iodo or a sulfonate group;
(b) for compounds of formula I in which $Q^1$ represents a direct bond and $R^x$ represents a group attached to $Q^1$ with a —CH$_2$—R$^{xx}$ moiety (in which, collectively, this group represents the $R^x$ moiety),

wherein $R^{xx}$ represents a part of the $R^x$ moiety ($R^x$ being hereinbefore defined), and which reaction is performed under reductive amination reaction conditions, for instance conditions known to those skilled in the art, e.g. as a reaction in "one pot", for instance in the presence of a selective reducing agent (which reduces the imine intermediate, but not the aldehyde starting material) such as sodium cyanoborohydride or, preferably, sodium triacetoxyborohydride, for instance in the presence of a mild acid (e.g. acetic acid), in a suitable solvent (e.g. dichloromethane). Alternative conditions may also be employed, for instance, first a condensation reaction, followed by reaction in the presence of a reducing agent (which need not be "imine" selective, e.g. sodium borohydride may be employed when the reaction is performed in two steps);
(ii) for compounds of formula I in which the requisite pyrimidine is attached to $X^2$ in which $X^2$ represents —N—, reaction of a compound of formula V,

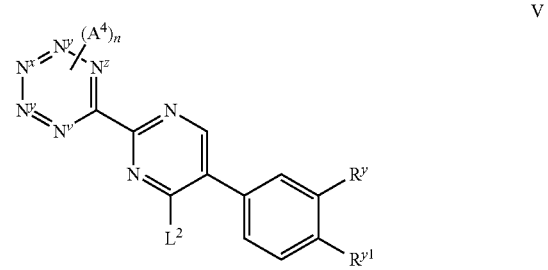

wherein L² represents a suitable leaving group, such as halo (e.g. chloro), with a compound of formula VI

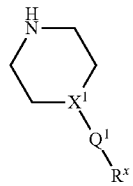

VI wherein X¹, Q¹ and R^x are as hereinbefore defined, under aromatic nucleophilic substitution reaction conditions, for instance such as those known in the art, e.g. in the presence of a base (such as an organic base, e.g. a dialkylamine base, for instance N,N-diisopropylethylamine);
(iii) for compounds in which there is a —CH₂— moiety present, reduction of a corresponding compound in which there is a —C(O)— moiety present, in the presence of a suitable reducing agent, e.g. LiAlH₄;
(iv) reaction with a compound of formula VII,

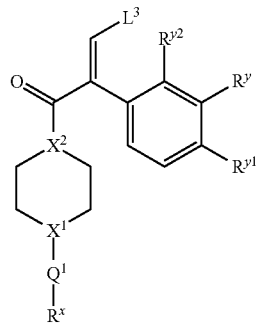

VII wherein L³ represents a suitable leaving group (preferably an amino moiety, such as —N(CH₃)₂), and the integers (e.g. R^y, R^{y1}, R^{y2}, Q¹, R^x, X¹ and X²)) are as hereinbefore defined, with a compound of formula VIII,

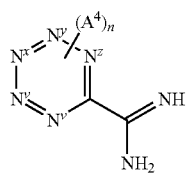

VIII or a derivative thereof (e.g. a salt, such as a HCl salt), in which the integers (e.g. N^v, N^w, N^x, N^y, N^z, A⁴ and n are as hereinbefore defined), under reaction conditions that promotes the cyclisation (e.g. in the presence of a base, such as an inorganic base e.g. tBuOK, and a suitable solvent such as an alcoholic solvent, e.g. ethanol, which reaction may be performed at elevated temperature);
(v) for compounds containing a —C(F)₂— moiety, reaction of a corresponding compound containing a —C(O)-moiety, by reaction with an appropriate "fluoride" reagent (e.g. diethyl amino sulfur trifluoride; e.g. in the presence of a suitable solvent such as dichloromethane).

Compounds of formula II may be prepared by reaction of a compound of formula IX,

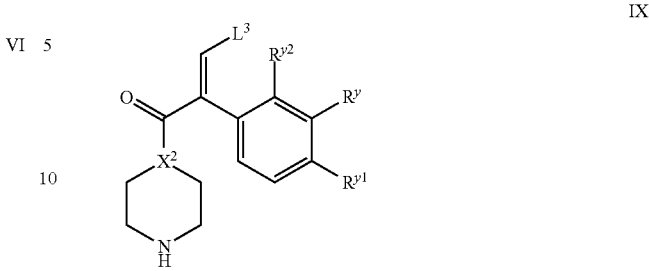

IX or a derivative thereof (such as a protected derivative, e.g. protected on the —N(H)-moiety with e.g. a Boc group) wherein the integers (e.g. L³, R^y, R^{y1}, R^{y2}, Q¹, R^x and X²) are as hereinbefore defined with a compound of formula VIII as hereinbefore defined.

Compounds of formula V may be prepared in accordance with the procedures described herein.

Compounds of VII and IX may be prepared by reaction of a corresponding compound of formula X,

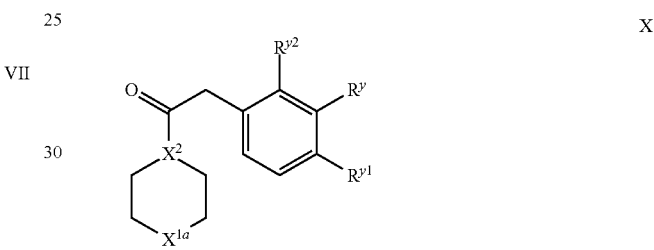

X wherein X^{1a} represents —X¹-Q¹-R^x (in the case of preparation of compounds of formula VII) or —N(H)— (in the case of preparation of compounds of formula IX, or a protected moiety thereof, e.g. —N(Boc)-) and the other integers (e.g. X², R^y, R^{y1} and R^{y2}) are as hereinbefore defined, with a compound of formula XI, $$O=C(H)-L^3$$ XI in which L³ is as hereinbefore defined (and in particular, represents an amino group, such as —N(CH₃)₂ so forming e.g. DMF), for instance reaction of DMF-DMA in the presence of a suitable solvent (e.g. an aromatic solvent, such as toluene) at reflux.

Compounds of formula X may be prepared in accordance with the procedures described herein.

It is evident that in the foregoing and in the following reactions, the reaction products may be isolated from the reaction medium and, if necessary, further purified according to methodologies generally known in the art, such as extraction, crystallization and chromatography. It is further evident that reaction products that exist in more than one enantiomeric form, may be isolated from their mixture by known techniques, in particular preparative chromatography, such as preparative HPLC, chiral chromatography. Individual diastereoisomers or individual enantiomers can also be obtained by Supercritical Fluid Chromatography (SCF).

The starting materials and the intermediates are compounds that are either commercially available or may be prepared according to conventional reaction procedures generally known in the art.

The following examples illustrate the present invention without being limited thereto.

Experimental Part

General scheme 1:

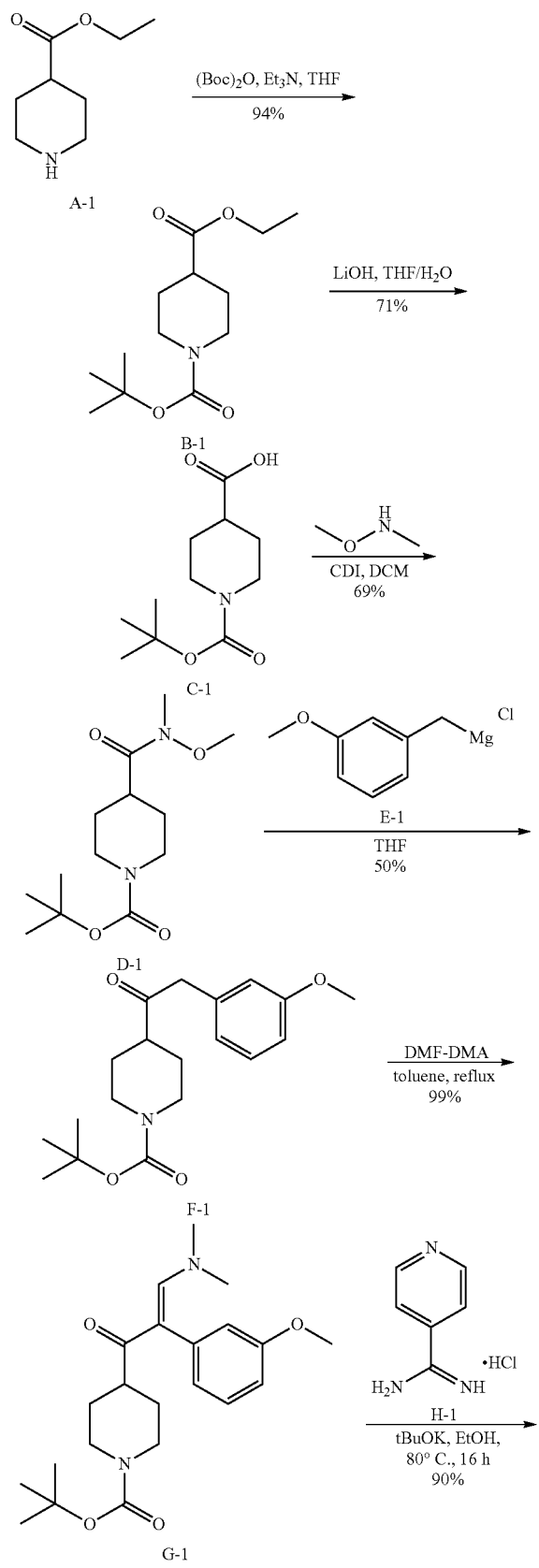

-continued

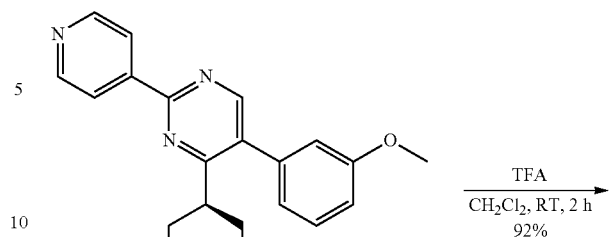

1. Synthesis of Intermediate B-1:

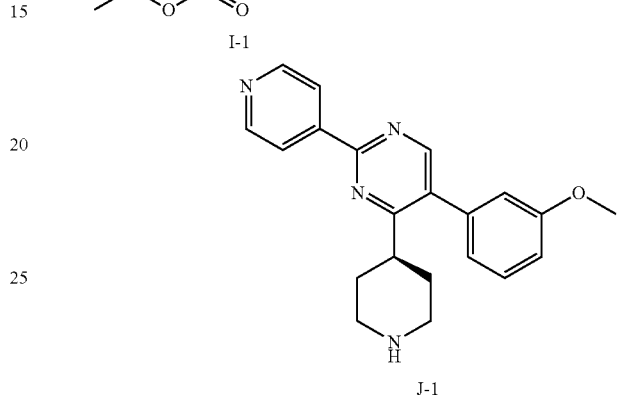

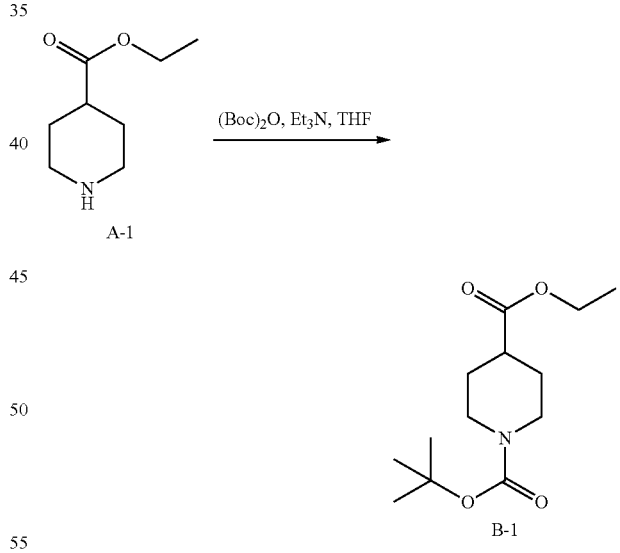

To a solution of A-1 (100 g, 0.64 mol) and Et₃N (64.37 g, 0.64 mol) in THF (1000 mL) was added Boc₂O (138.82 g, 0.64 mol) at 0° C., the mixture was stirred at room temperature for 16 hrs. Then the reaction mixture was poured into H₂O (1000 mL) and extracted with EtOAc (500 mL×3). The combined organic layers were dried over anhydrous Na₂SO₄ and concentrated in vacuum to give intermediate B-1 (138.10 g, yield: 84%).

2. Synthesis of Intermediate C-1:

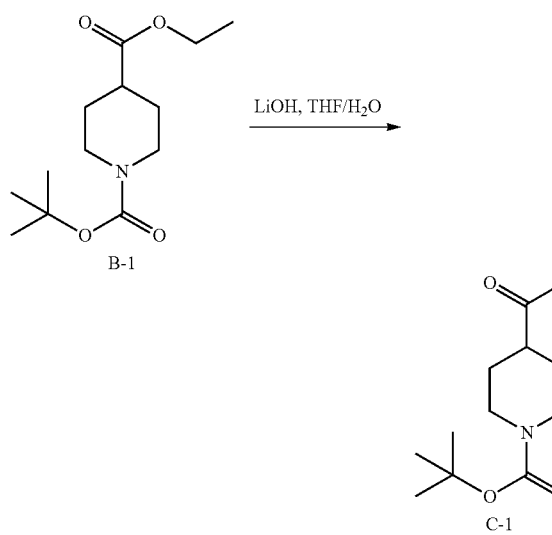

To a solution of B-1 (138 g, 0.54 mol) in 1 L of THF and 1 L of H₂O was added LiOH.H₂O (67.51 g, 1.61 mol) at 0° C. After the addition, the mixture was stirred at 25° C. for 15 hrs. The organic solvent was removed under reduced pressure. The mixture was extracted with EtOAc (500 mL×3), and the aqueous layer was separated and treated with 0.5 M aq. HCl to adjust to pH=3 and extracted with CH₂Cl₂ (1 L×3). The combined organic layers were dried over anhydrous Na₂SO₄ and concentrated to give intermediate C-1 (80 g, 65%) as a white solid.

3. Synthesis of Intermediate D-1:

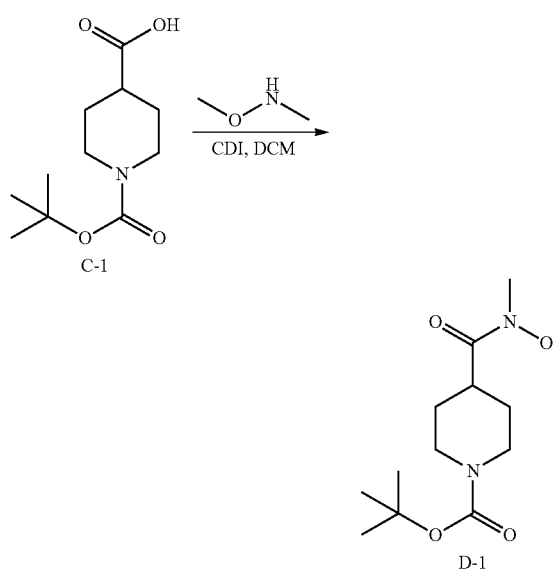

To a stirred solution of C-1 (80 g, 0.35 mol) in 1 L of anhydrous CH₂Cl₂ was added CDI (62.24 g, 0.38 mol) under N₂ at 0° C. After the addition, the mixture was stirred at 25° C. for 1 hour, gas formation was observed. Et₃N (42.37 g, 42 mol) was added, the mixture was stirred at 25° C. for 30 min, then O,N-dimethylhydroxylamine hydrochloride (42.54 g, 0.44 mol) was added. After the addition, the mixture was stirred at 25° C. for 15 hrs. The mixture was washed with water, aq. NaHCO₃ and aq. citric acid monohydrate. The organic layer was separated, dried over anhydrous Na₂SO₄ and concentrated to get intermediate D-1 (80 g, 95%) as a white solid.

4. Synthesis of Intermediate F-1:

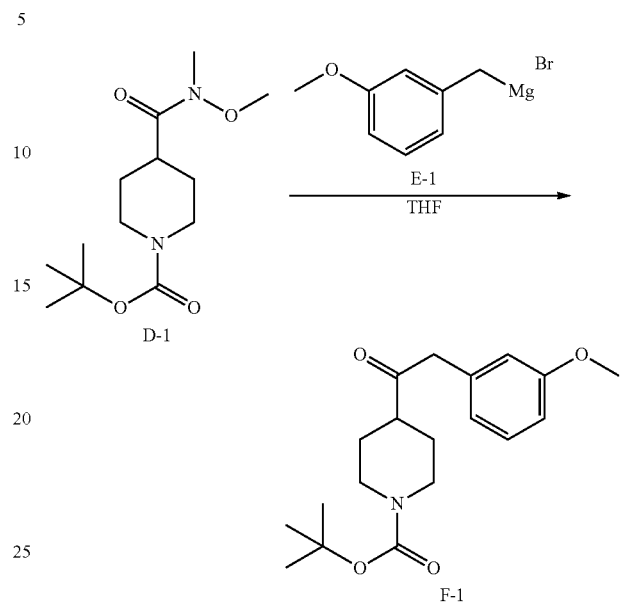

To a stirred solution of D-1 (20 g, 73.44 mmol) in 500 mL of anhydrous THF was added E-1 (350 mL, 88 mmol) under N₂ at 0° C. After the addition, the mixture was stirred at 0° C. for 2 hours and 15° C. for 6 hours. Then the mixture was filtered. The solid was dissolved in NH₄Cl (100 mL) and extracted with EtOAc (200 mL×2). The combined organic layers were washed with brine (200 mL×2), dried over MgSO₄, filtered and concentrated to obtain 16.2 g of intermediate F-1 as white solid.

5. Synthesis of Intermediate G-1:

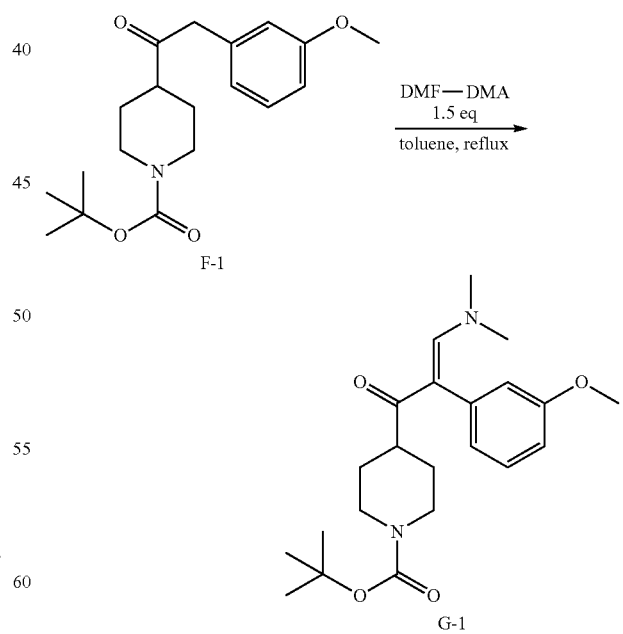

A stirred solution of F-1 (15 g, 45 mmol) and DMF-DMA (9 mL, 67.48 mmol) in 300 mL of anhydrous toluene was stirred at 110° C. under N₂ for 4 h. Then the solvent was evaporated under reduced pressure to obtain 12.15 g of intermediate G-1.

6. Synthesis of Intermediate I-1:

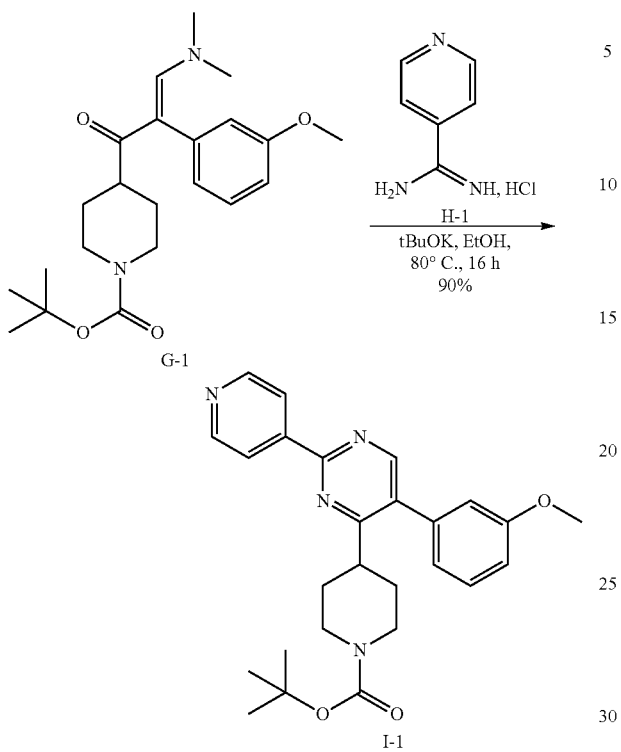

To a stirred solution of G-1 (2.5 g, 6.4 mmol) in ethanol (24 mL) was added, at room temperature isonicotinimidamide hydrochloride H-1 (1.5 g, 9.65 mmol) followed by potassium tert-butoxide (1.44 g, 12.9 mmol).

The reaction mixture was then heated at 80° C. for 16 hours. After 100% consumption of G-1 (monitoring by LCMS), the reaction mixture was allowed to cool to room temperature and concentrated in vacuum. The residue was, then, diluted with dichloromethane (150 mL) and treated with water (150 mL). The aqueous crude mixture was extracted with dichloromethane (2×150 mL). The combined organic layers were dried over sodium sulfate, filtered and concentrated in vacuum. The crude compound was then purified on silica gel using dichloromethane/ethyl acetate: 50/50 to afford the desired intermediate I-1 as a light white solid (2.58 g, 90% yield).

7. Synthesis of Intermediate J-1:

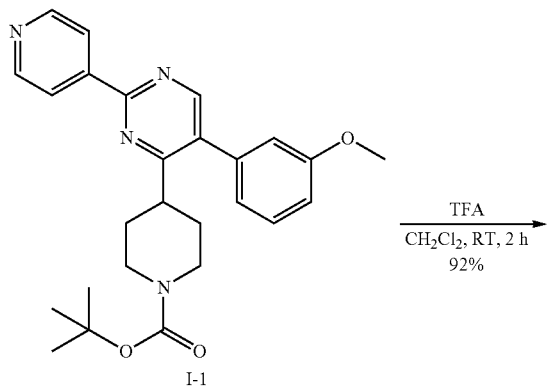

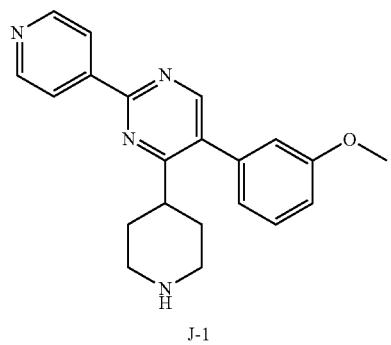

To a solution of I-1 (2.8 g, 6.25 mmol) in dichloromethane (31 mL), trifluoroacetic acid (5.7 mL) was added at room temperature. The reaction mixture was then stirred at room temperature for 3 hours. After complete consumption of I-1 (monitoring by TLC), the reaction mixture was concentrated in vacuum to get a residue that was taken up in dichloromethane (100 mL) and treated with a saturated aqueous solution of potassium carbonate (100 mL). The aqueous crude mixture was extracted with dichloromethane (2×100 mL). The combined organic layers were dried over sodium sulfate, filtered and concentrated in vacuum to afford the desired intermediate J-1 as a beige solid (2 g, 92%) which was used in the next step without any further purification.

General scheme 2:

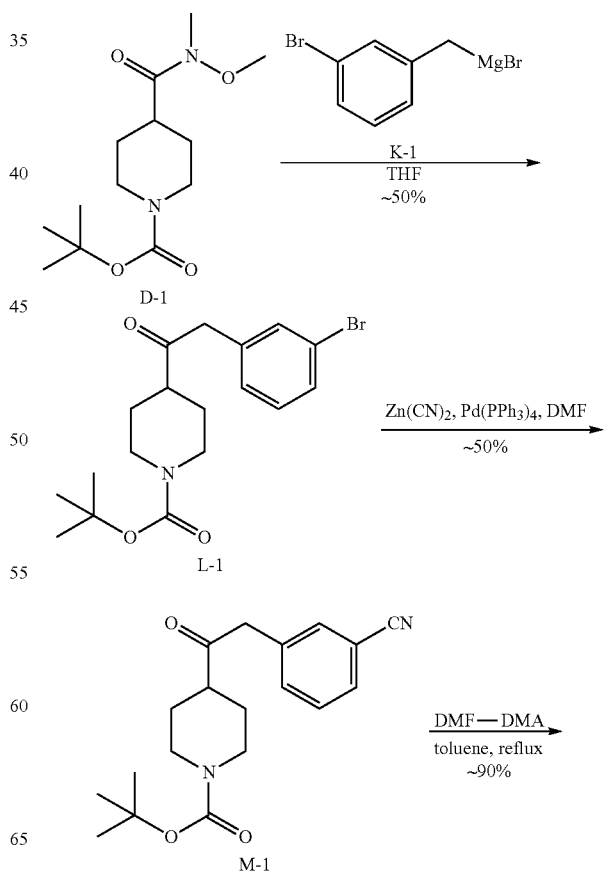

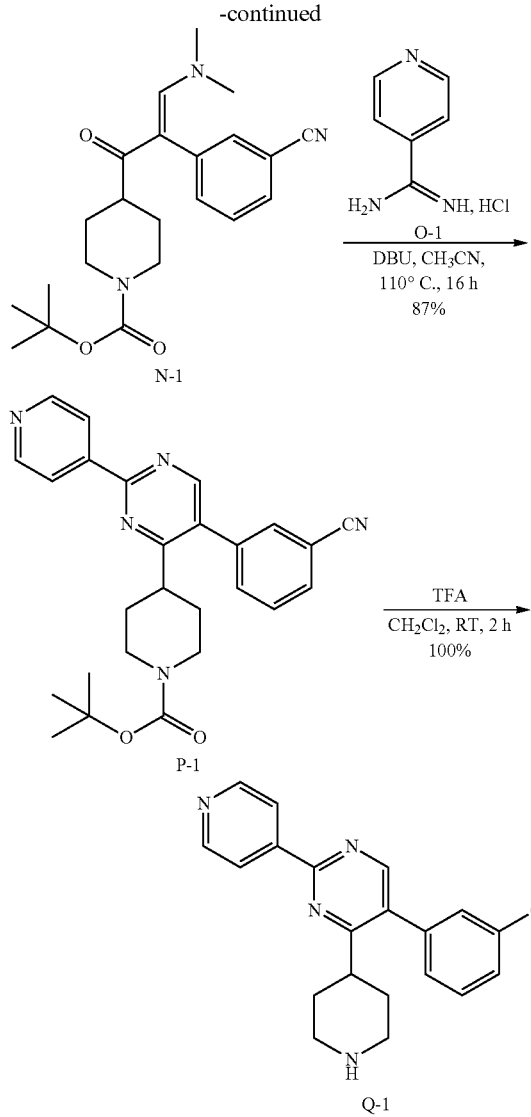

1. Synthesis of Intermediate L-1:

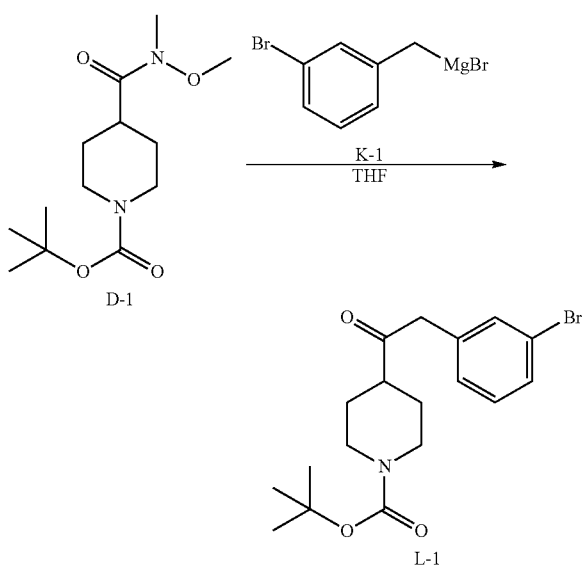

To a stirred solution of D-1 (30 g, 104 mmol) in 500 mL of anhydrous THF was added K-1 (500 mL, 125 mmol) under N₂ at 0° C. The mixture was stirred at 15° C. for 18 h. The reaction mixture was diluted with NH₄Cl (250 mL) and EtOAc (500 mL). The organic layer was washed with brine, dried over MgSO₄, filtered and concentrated. The residue was purified by chromatography on silica gel (Petroleum ether:Ethylacetate=20:1) to obtain 15.12 g of intermediate L-1.

2. Synthesis of Intermediate M-1:

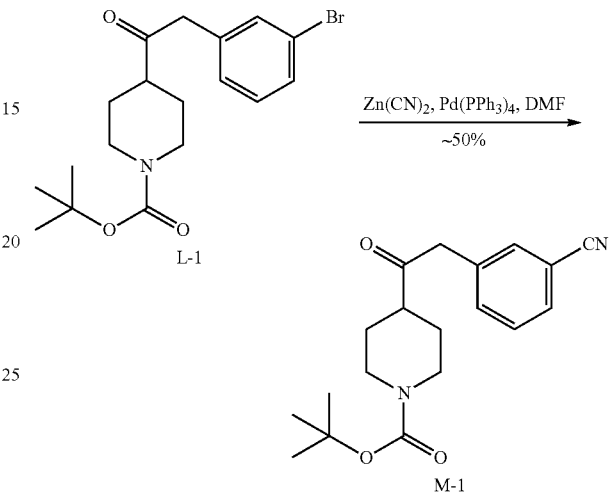

The mixture of L-1 (14.20 g, 37.14 mmol), Zn(CN)₂ (6.54 g, 55.72 mmol) and Pd(PPh₃)₄ (2.15 g, 1.86 mmol) in DMF (140 mL) was stirred at 100° C. for 18 h. A solution of NaHCO₃ (200 mL) was added after the mixture was cooled to the room temperature. The resulting mixture was extracted with EtOAc (200 mL×2). The combined organic layers were washed with NaHCO₃ (100 mL), brine (100 mL), dried over MgSO₄, filtered and concentrated. The residue was purified by chromatography on silica gel (Petroleum ether:Ethylacetate=10:1) to obtain intermediate M-1 (12.04 g) as a white solid.

3. Synthesis of Intermediate N-1:

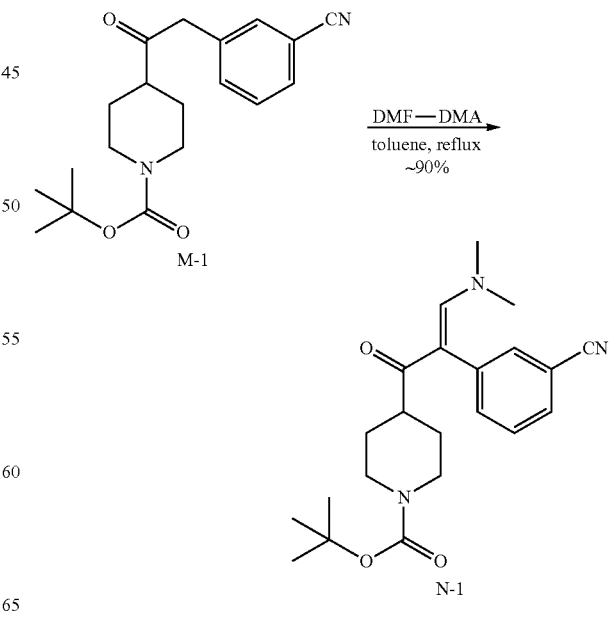

A stirred solution of M-1 (12.00 g, 36.54 mmol) and DMF-DMA (6.53 g, 58.81 mmol) in 300 mL of anhydrous toluene was stirred at 110° C. for 4 h under N₂. Then the solvent was evaporated under reduced pressure. The residue was purified by chromatography on silica gel (Petroleum ether:Ethylacetate=1:1) to obtain intermediate N-1 (10.05 g) as a white solid.

4. Synthesis of Compound P-1:

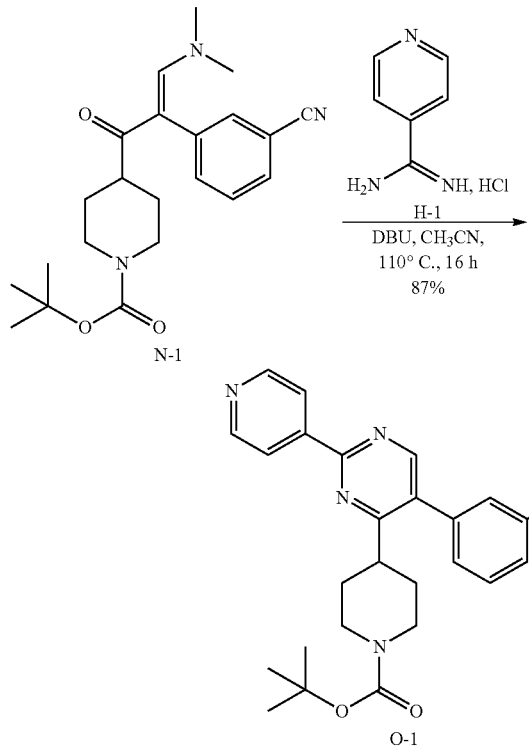

To a stirred solution of N-1 (800 mg, 2.0 mmol) in acetonitrile (8 mL) at room temperature, isonicotinimidamide hydrochloride H-1 (657 mg, 4.1 mmol) was added followed by DBU (0.93 mL, 6.2 mmol). The reaction mixture was then heated in a sealed tube at 110° C. for 16 hours. After complete consumption of N-1 (monitoring by LCMS), the reaction mixture was allowed to cool to room temperature and treated with water (30 mL). The aqueous crude mixture was extracted with dichloromethane (3×30 mL). The combined organic layers were dried over sodium sulfate, filtered and concentrated in vacuum. The crude compound (1.3 g) was then purified on silica gel using dichloromethane/methanol/ammonium hydroxide solution (33% in H₂O): 98/2/0.1 to afford the desired intermediate O-1 as a light yellow solid (800 mg, 87% yield).

5. Synthesis of Intermediate P-1:

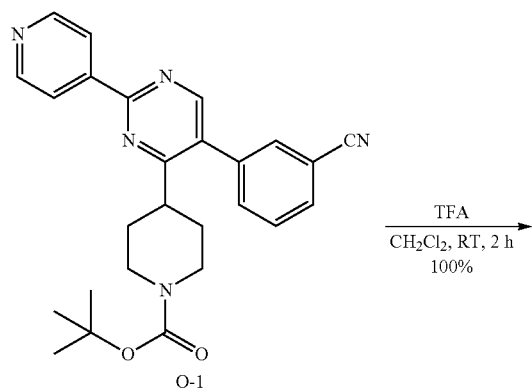

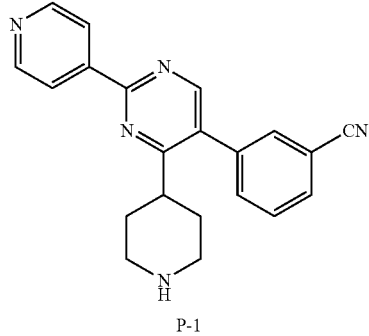

To a solution of O-1 (800 mg, 1.8 mmol) in dichloromethane (10 mL) was added, at room temperature, trifluoroacetic acid (2.15 mL). The reaction mixture was then stirred at room temperature for 2 hours. After complete consumption of O-1 (monitoring by TLC), the reaction mixture was treated with a saturated aqueous solution of sodium carbonate (30 mL). The aqueous crude mixture was extracted with dichloromethane (3×30 mL). The combined organic layers were dried over sodium sulfate, filtered and concentrated in vacuum to afford the desired intermediate P-1 as a light yellow solid (695 mg, quantitative yield) which was used in the next step without any further purification.

General scheme 3:

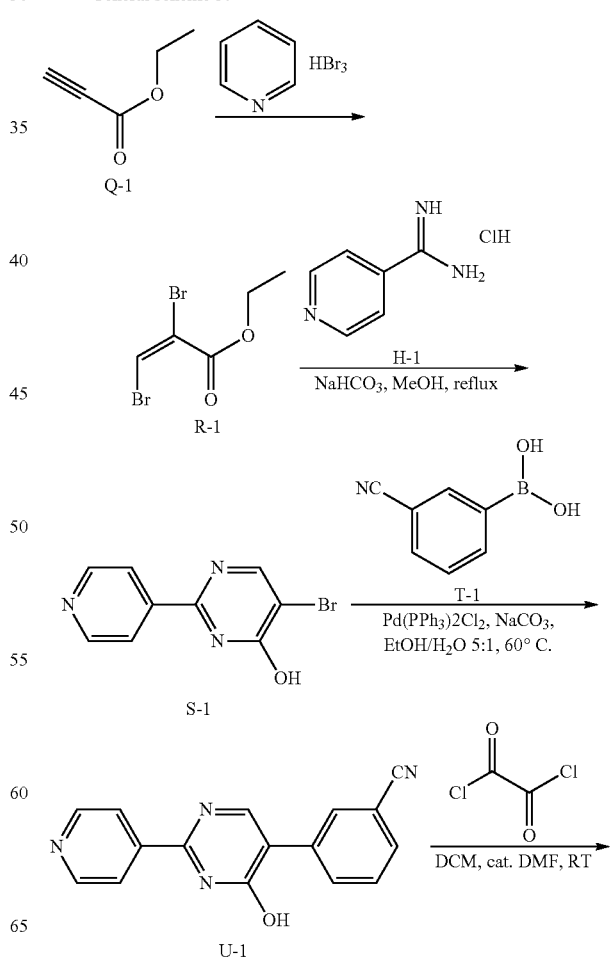

-continued

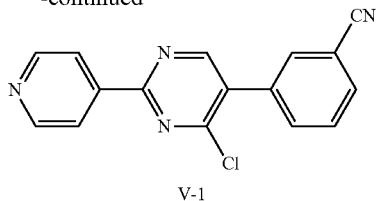
V-1

1. Synthesis of Intermediate R-1:

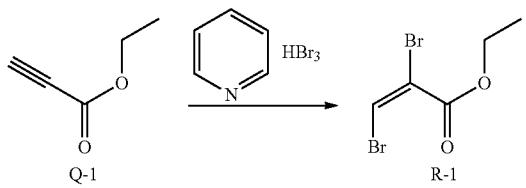

A mixture of Q-1 (150 g, 1.53 mol) and pyridinium tribromide (635 g, 1.99 mol) in CH$_2$Cl$_2$ (2 L) was stirred at 20° C. for 96 hours. Then the reaction mixture was washed with an aqueous solution of Na$_2$S$_2$O$_3$ (2×1 L) and brine (1 L), dried over MgSO$_4$, filtered and concentrated to give intermediate R-1 (380 g, 96%) as yellow liquid.

2. Synthesis of Intermediate S-1:

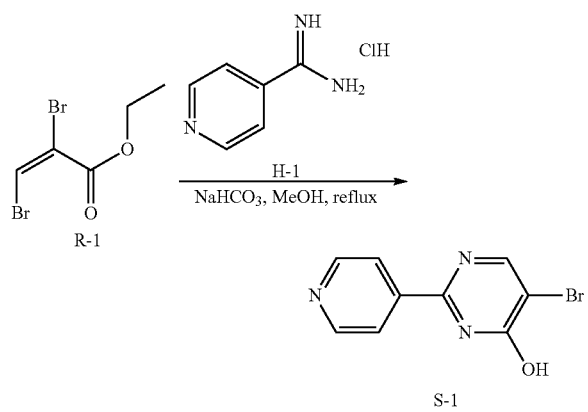

To a mixture of R-1 (170 g, 1.08 mol), H-1 (334.00 g, 1.29 mol) and NaHCO$_3$ (362.45 g, 4.31 mol) in 2.5 L of anhydrous MeOH was stirred at 80° C. for 12 hrs under N$_2$. Then the mixture was cooled and filtered, the filtrate was concentrated. The residue was purified by chromatography on silica gel (CH$_2$Cl$_2$:MeOH=10:1) to obtain intermediate S-1 (170 g) as a brown solid.

3. Synthesis of Intermediate U-1:

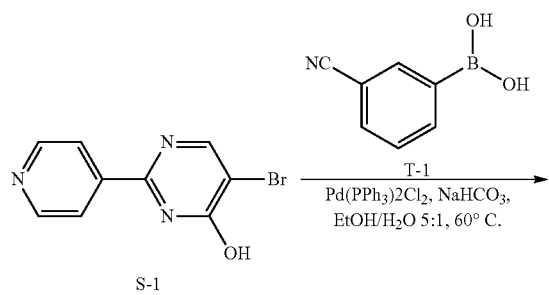

-continued

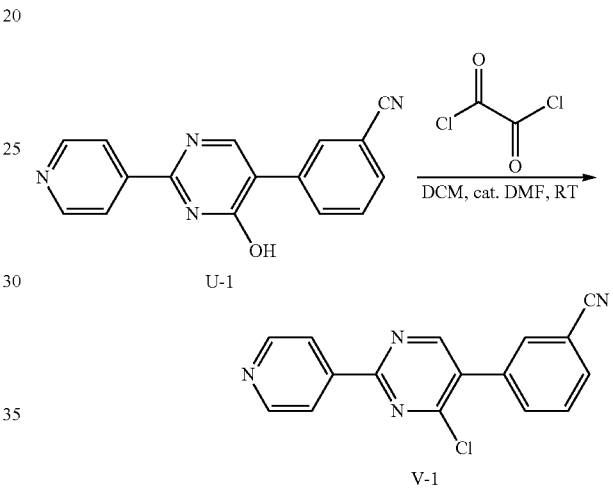
U-1

A stirred mixture of S-1 (150 g, 595.08 mmol) and T-1 (131.16 g, 892.62 mmol) in 1500 mL of EtOH and 300 mL of H$_2$O was added NaHCO$_3$ (189.21 g, 1.79 mol) and Pd(PPh$_3$)$_2$Cl$_2$ (15 g) under N$_2$. The reaction mixture was stirred at 60° C. for 8 hrs under N$_2$. Then the mixture was filtered and the solvent was evaporated under reduced pressure. The residue was washed with EtOAc to give intermediate U-1. The crude compound was used directly in the next step.

4. Synthesis of Intermediate V-1:

A stirred suspension of U-1 (100 g, crude) in 1500 mL of anhydrous CH$_2$Cl$_2$ was added dropwise oxalyl dichloride (462.77 g, 3.65 mol) at 0° C. under N$_2$. Then DMF (53.30 g, 7.29 mol) was added and the reaction mixture was stirred at 15° C. for 4 h under N$_2$. Then the solvent was evaporated under reduced pressure. The residue was dissolved in EtOAc (1 L) and an aqueous of NaHCO$_3$ (1 L). The organic layer was washed with brine, dried over MgSO$_4$ and concentrated. The residue was purified by chromatography on silica gel (CH$_2$Cl$_2$:MeOH=20:1) to obtain the crude product. The crude product was washed with EtOH to give 9.4 g of intermediate V-1 as a brown solid, and was used directly in the next step.

Synthesis of Final Compound 6:

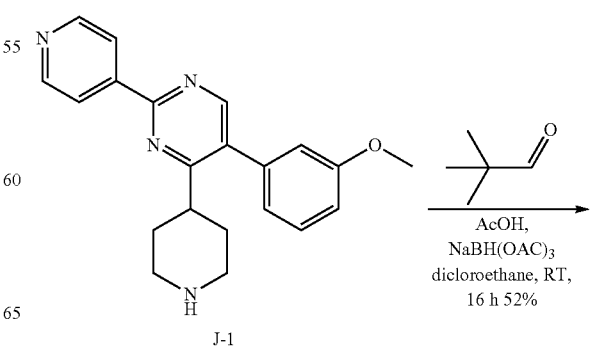

-continued

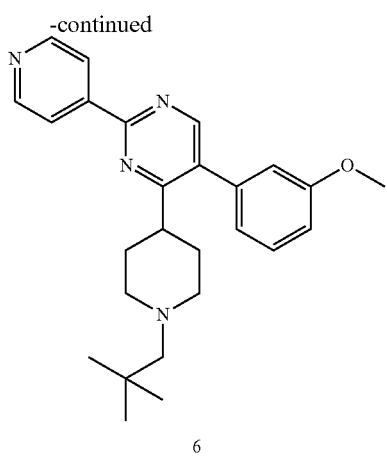

6

To a solution of J-1 (250 mg, 0.722 mmol) in dichloroethane (10 mL), acetic acid (0.124 mL, 2.17 mmol) and 2,2-dimethylpropanal (0.157 mL, 1.45 mmol) were added. The reaction mixture was then stirred at room temperature for 2 hours. Sodium triacetoxyborohydride (428 mg, 2 mmol) was then added and the mixture was stirred at room temperature for 3 h. In order to complete the reaction, 2,2-dimethylpropanal (0.157 mL, 1.45 mmol) and acetic acid (0.124 mL, 2.17 mmol) were added and the mixture was stirred at room temperature for 1 h before adding sodium triacetoxyborohydride (428 mg, 2 mmol). Reaction mixture was stirred at room temperature for 12 hours and then diluted with dichloromethane and treated with a saturated solution of sodium bicarbonate. The aqueous layer was extracted with dichloromethane. The combined organic layers were dried over sodium sulfate, filtered and concentrated in vacuum. The crude compound was then purified on silica gel using dichloromethane/methanol/ammonium hydroxide solution (33% in $H_2O$): 98/2/0.1 to afford the desired compound 6 as a white solid (156 mg, 52% yield).

Synthesis of Final Compound 9:

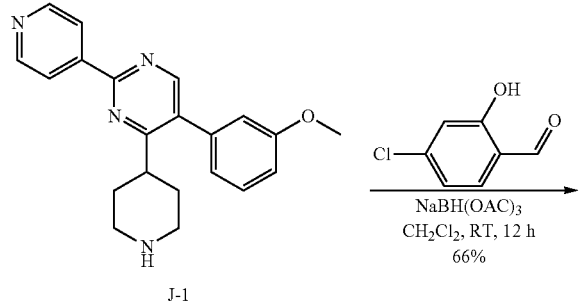

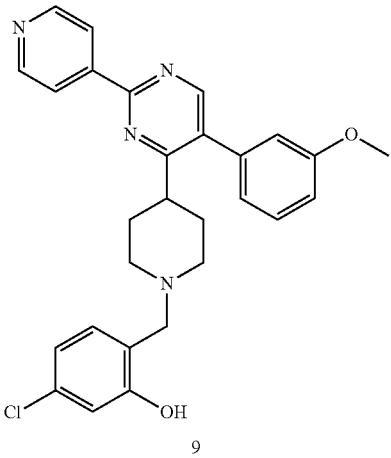

9

To a solution of J-1 (0.15 g, 0.433 mmol) and 4-chloro-2-hydroxybenzaldehyde (0.068 g, 0.433 mmol) in dichloromethane (4 mL) under $N_2$-atmosphere was added sodium triacetoxyborohydride (0.138 g, 0.649 mmol) in one portion. The reaction mixture was stirred at room temperature overnight. The reaction mixture was directly loaded on a preparative TLC and eluted four times with [heptane(1):EtOAc (2)]. The main band was scratched off, and eluted from the $SiO_2$ with [EtOAc(9):MeOH(1)]. The elute was evaporated until dryness to yield 0.139 g of compound 9 (66%).

Synthesis of Final Compound 12:

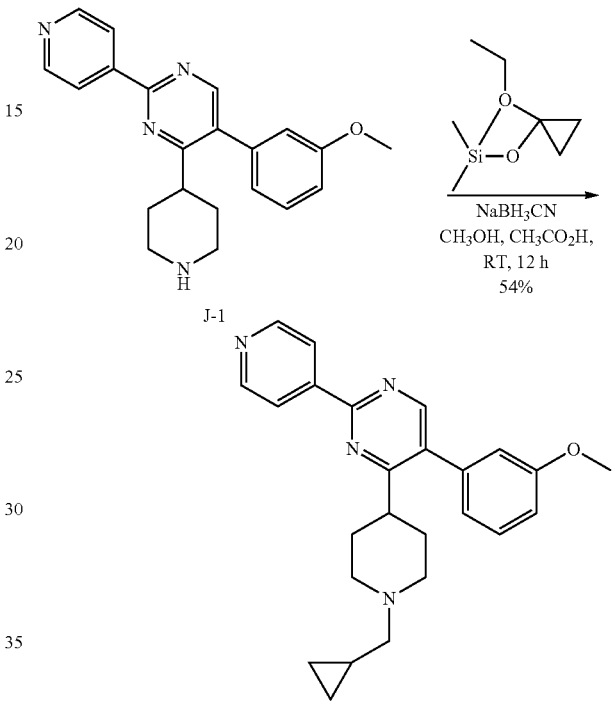

12

To a solution of J-1 (0.1 g, 0.289 mmol) in methanol (extra dry) (3 mL) and acetic acid (0.1 mL) under $N_2$-atmosphere was added (1-ethoxycyclopropoxy)trimethylsilane (0.061 mL, 0.303 mmol) in one portion. The reaction mixture was stirred at room temperature for 0.5 h, then sodium cyanoborohydride (0.027 g, 0.433 mmol) was added and the reaction mixture was heated to reflux overnight, then allowed to cool to room temperature and stirred 24 h. The reaction mixture was directly loaded on a preparative TLC and eluted with [$CH_2Cl_2$ (95):MeOH (5)]. The main band was scratched off, and eluted from the $SiO_2$ with [EtOAc (9):MeOH (1)]. The elutes were evaporated until dryness to yield 0.089 g of final compound 12 (54%).

Synthesis of Final Compound 20:

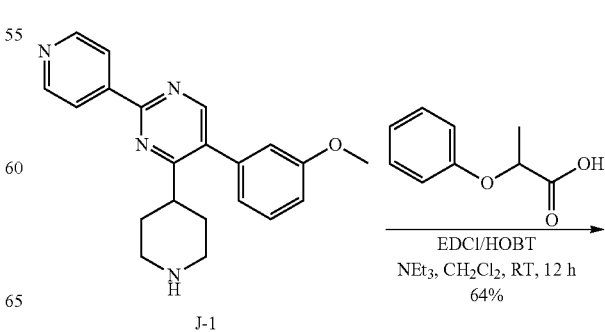

-continued

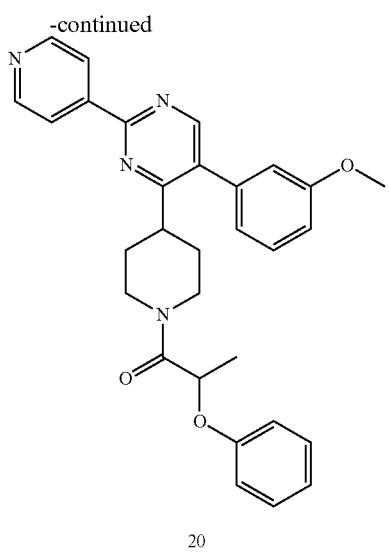

20

A mixture of J-1 (100 mg, 0.289 mmol), 2-phenoxypropionic acid (62.4 mg, 0.375 mmol), EDCI (83 mg, 0.433 mmol), HOBT (58.5 mg, 0.433 mmol) and NEt$_3$ (61 µL, 0.433 mmol) in CH$_2$Cl$_2$ (5 mL) was stirred at RT overnight. Water was added and the layers were decanted. The organic layer was washed with water, dried over MgSO$_4$, filtered and the solvent was evaporated. The crude compound was purified by chromatography over silica gel (15-40 µm, 30 g) with CH$_2$Cl$_2$/MeOH/NH$_4$OH 97.5/2.5/0.1. The solvent was evaporated to give final compound 20 (64%).

Synthesis of Final Compound 21:

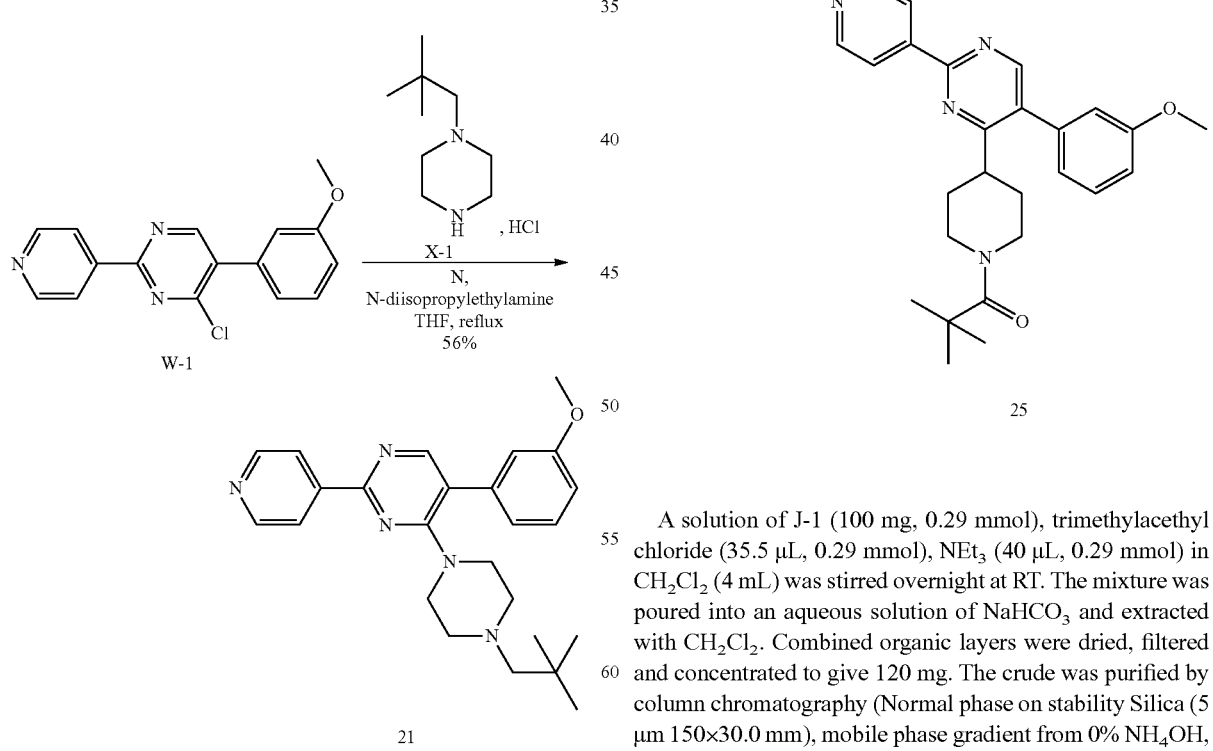

Intermediate W-1 was synthesized according to the procedure described for intermediate V-1, using (3-methoxyphenyl)boronic acid instead of T-1. A solution of W-1 (99 mg, 0.333 mmol), X-1 (77 mg, 0.399 mmol) and N,N-diisopropylethylamine (0.142 mL, 0.831 mmol) in THF (20 mL) was stirred at reflux overnight. In order to complete the reaction, X-1 (236 mg, 1.22 mmol) and N,N-diisopropylethylamine (0.63 mL, 3.7 mmol) were added portion wise over 2 days and the reaction mixture was stirred at reflux. Reaction mixture was allowed to come to RT and solvents were removed in vacuum. Residual brown oil (approx. 0.5 g) was dissolved in MeOH/CH$_2$Cl$_2$ and solids were filtered off. Preparative TLC (Heptane/Diethylether, 4:1 [3x], 9:1 [3x]) afforded 80 mg of a colorless oil. Material was dissolved in DIPE and heptane was added. Removal of solvents in vacuum afforded compound 21 as a colorless solid (70 mg, 56%).

Synthesis of Final Compound 25:

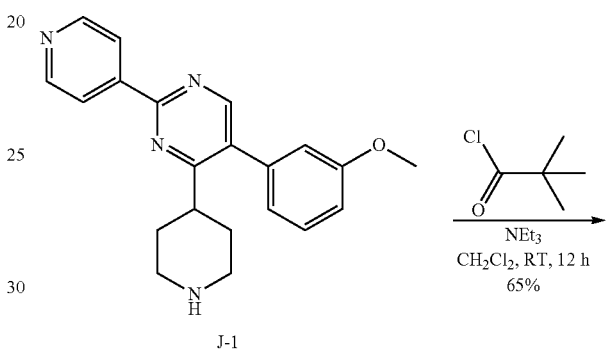

A solution of J-1 (100 mg, 0.29 mmol), trimethylacetyl chloride (35.5 µL, 0.29 mmol), NEt$_3$ (40 µL, 0.29 mmol) in CH$_2$Cl$_2$ (4 mL) was stirred overnight at RT. The mixture was poured into an aqueous solution of NaHCO$_3$ and extracted with CH$_2$Cl$_2$. Combined organic layers were dried, filtered and concentrated to give 120 mg. The crude was purified by column chromatography (Normal phase on stability Silica (5 µm 150×30.0 mm), mobile phase gradient from 0% NH$_4$OH, 100% DCM, 0% MeOH to 0.6% NH$_4$OH, 94% DCM, 6% MeOH). The solid was crystallized in diisopropylether and dried under vacuum pressure at 70° C. to give compound 25 (81 mg, 65%).

Synthesis of Final Compound 26:

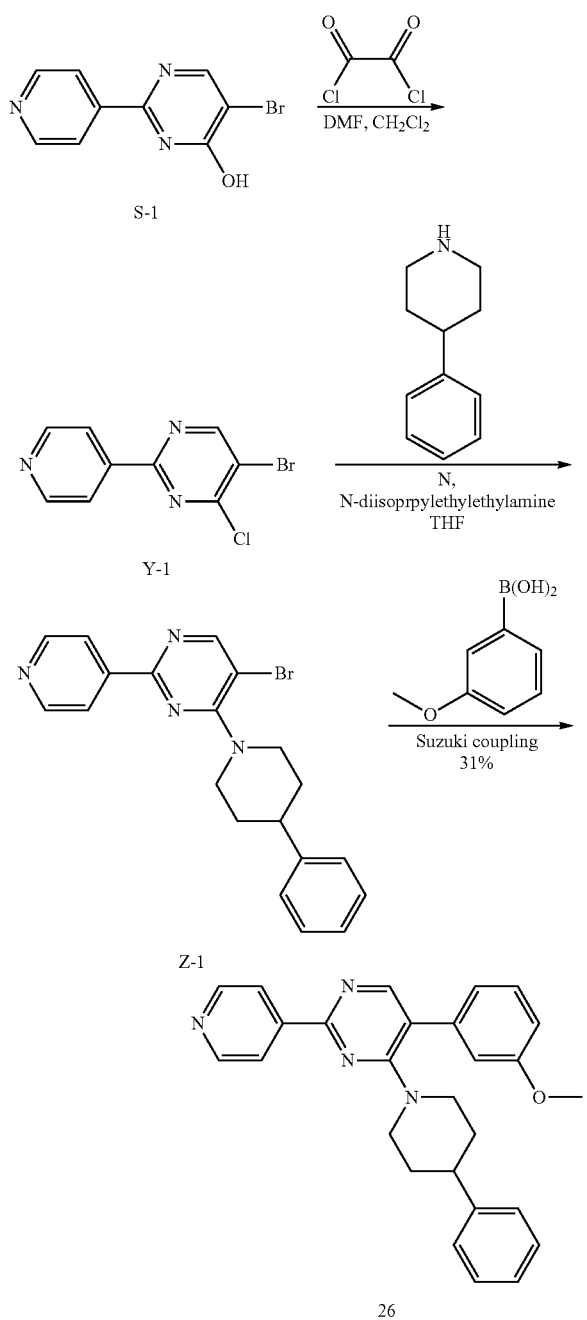

organic extracts were dried with Na$_2$SO$_4$ and solvents were removed under vacuum. The crude was purified by flash chromatography (CH$_2$Cl$_2$, 2% MeOH) to afford intermediate Z-1 as a yellow oil (66 mg, 46%).

A suspension of Z-1 (0.066 g, 0.167 mmol), 2-methoxyphenylboronic acid (0.038 g, 0.25 mmol) and sodium carbonate (0.060 g, 0.566 mmol) in DME (8 mL)/H$_2$O (2 mL) was flushed with argon for 5 min. Trans-BIS(Triphenylphosphine)palladium(II) chloride (6 mg, 8.6 µmol) was added and the suspension was flushed with argon for 5 min. Reaction mixture (suspension) was stirred at 60° C. under argon for 2 h. H$_2$O and EtOAc were added. Solids were filtered off. Layers were separated. Aqueous layer was extracted with EtOAc. Combined organic layers were washed with brine and dried with Na$_2$SO$_4$. Solvents were removed under vacuum. The material was dissolved in CH$_2$Cl$_2$. Water was added and the mixture was stirred vigorously overnight. Layers were separated. Aqueous layer was extracted with CH$_2$Cl$_2$. Combined organic extracts were dried with Na$_2$SO$_4$. Solvents were removed under vacuum. Material was coevaporated with CH$_2$Cl$_2$. Et$_2$O was added to the yellow oil. The material solidified. The suspension was stirred in Et$_2$O overnight. The solid was filtered off, washed with Et$_2$O and H$_2$O and dried to give final compound 26 (31%).

Synthesis of Final Compound 49:

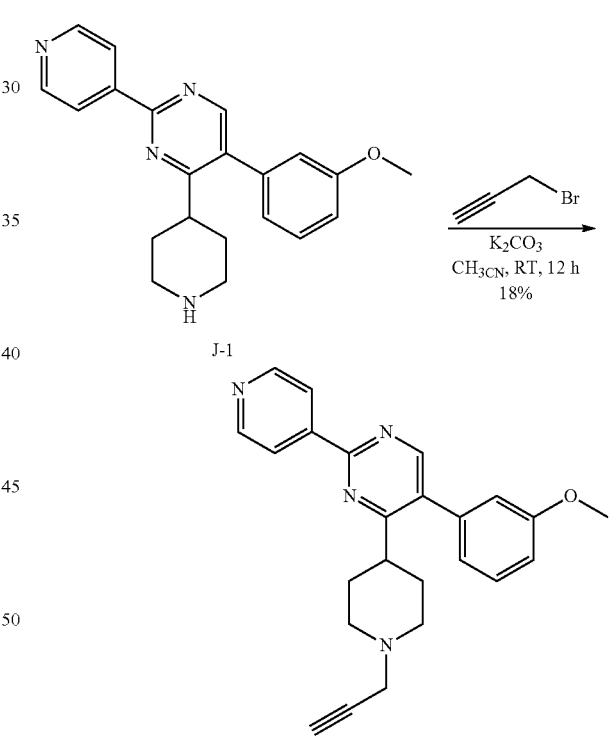

Under nitrogen, oxalyl chloride (0.22 mL, 2.55 mmoles) was added to a suspension of S-1 in CH$_2$Cl$_2$ (50 mL). DMF (0.02 mL) was added drop wise (exothermic) and the reaction mixture was stirred at RT for 3 h. Solvents were removed under vacuum. The crude material Y-1 was used directly in the next step.

4-phenyl piperidine (0.089 g, 0.549 mmoles) was added to a suspension of Y-1 (0.099 g, 0.366 mmol) in THF (8 mL). Upon addition, solids dissolved and color turned from brown-yellow to purple. N,N-diisopropylethylamine (0.188 mL, 1.098 mmol) was added and reaction mixture was stirred at reflux overnight. Water and EtOAc were added. Aqueous layer was extracted with EtOAc. Combined J-1 (100 mg, 0.289 mmol), K$_2$CO$_3$ (80 mg, 0.57 mmol), propargyl bromide (solution 80% WT in toluene, 39 µL, 0.35 mmol) in CH$_3$CN (4 mL) were stirred at RT overnight. H$_2$O and CH$_2$Cl$_2$ were added, organic phase was decanted, dried off over MgSO$_4$ powder, filtered and solvent was evaporated. The crude compound was purified by column chromatography over silica-gel column (15-40 µm, 30 g) in CH$_2$Cl$_2$/MeOH/NH$_4$OH 97/3/0.5 to give 20 mg of compound 49 after crystallization in CH$_3$CN/Diisopropylether (18%).

Synthesis of Final Compound 55:

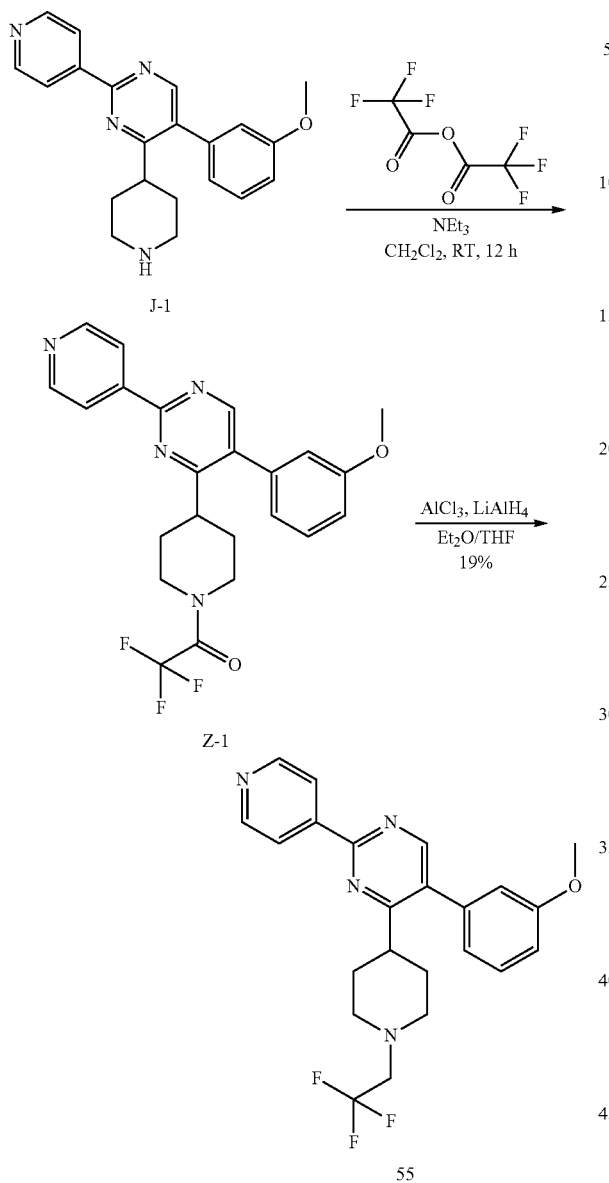

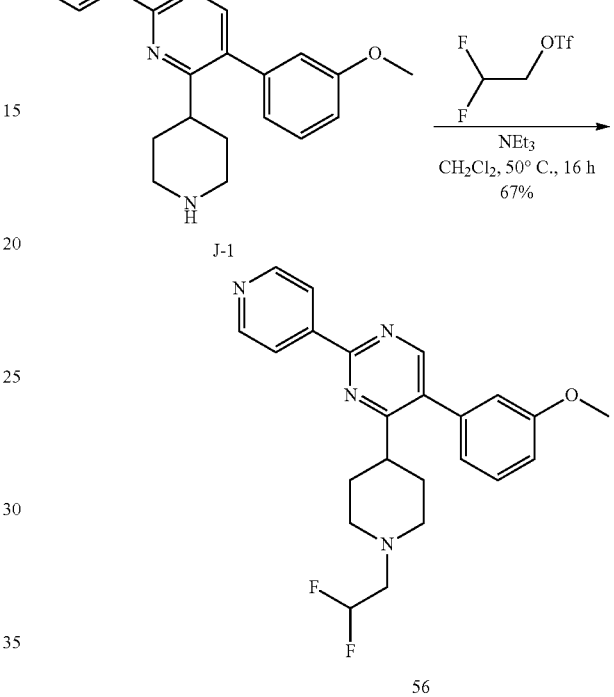

J-1 (200 mg, 0.58 mmol), trifluoroacetic anhydride (177 µL, 1.27 mmol), NEt₃ (642 µL, 4.62 mmol) in CH₂Cl₂ (4 mL) were stirred at RT for 12 h. The mixture was poured into an aqueous solution of NaHCO₃ and extracted with CH₂Cl₂. Combined organic layers were dried, filtered and concentrated to give 248 mg of intermediate Z-1. The crude compound was used directly in the next step.

Under a N₂ flow, at −70° C., Et₂O (5 mL) was added to AlCl₃ (97 mg, 0.73 mmol) then the mixture was stirred at 0° C. for 10 min. LiAlH₄ (1.12 mL, 2.24 mmol) was added drop wise at 0° C. and the mixture was stirred at 0° C. for 10 min. Z-1 (248 mg, 0.56 mmol) in THF (5 mL) was added drop wise and the mixture was stirred at 0° C. for 1 h. The reaction was quenched with ice and EtOAc was added. The layers were decanted. The organic layer was washed with water, dried over MgSO₄, filtered and the solvent was evaporated. The crude purified by column chromatography over silica gel (15-40 µm, 30 g) in CH₂Cl₂/MeOH/ NH₄OH 98/2/0.1. The compound was then was purified by achiral Super critical fluid chromatography on 2-ETHYL-PYRIDINE 6 µm 150×21.2 mm (mobile phase 92% CO₂, 8% MeOH) to give compound 55 (45 mg, 19%).

Synthesis of Final Compound 56:

To a solution of J-1 (250 mg, 0.72 mmol) in dichloromethane (3.6 mL) was added, at room temperature, 2,2-difluoroethyl triflate (230 mg, 1.08 mmol) followed by triethylamine (0.36 mL, 2.16 mmol, 3 eq). The reaction mixture was then stirred at 50° C. for 16 hours and treated with water (5 mL). The aqueous crude mixture was extracted with dichloromethane (3×10 mL). The combined organic layers were dried over sodium sulfate, filtered and concentrated in vacuum (300 mg). The crude compound was then purified on silica gel using ethyl acetate (100%) to afford the desired compound 56 as a white solid (200 mg, 67% yield).

Synthesis of Final Compound 57:

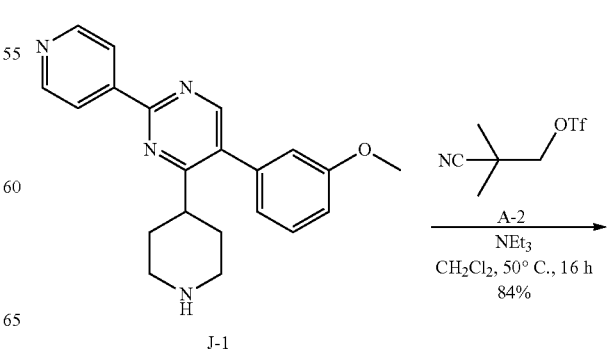

-continued

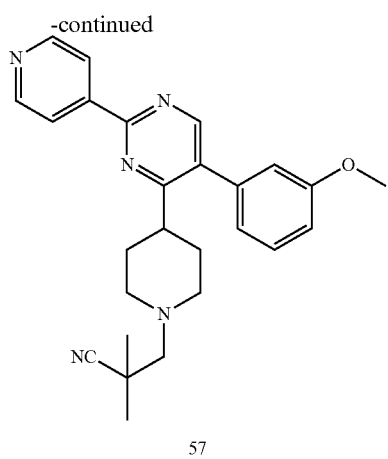

57

To a solution of J-1 (250 mg, 0.72 mmol) in dichloromethane (3.6 mL) was added, at room temperature, A-2 (247 mg, 1.08 mmol) followed by triethylamine (0.36 mL, 2.16 mmol). The reaction mixture was then stirred at 50° C. for 16 hours and treated with water (5 mL). The aqueous crude mixture was extracted with dichloromethane (3×10 mL). The combined organic layers were dried over sodium sulfate, filtered and concentrated in vacuum (650 mg). The crude compound was then purified on silica gel using ethyl acetate/dichloromethane: 70/30 to afford the desired compound 57 as a white solid (260 mg, 84% yield).

Synthesis of Final Compound 58:

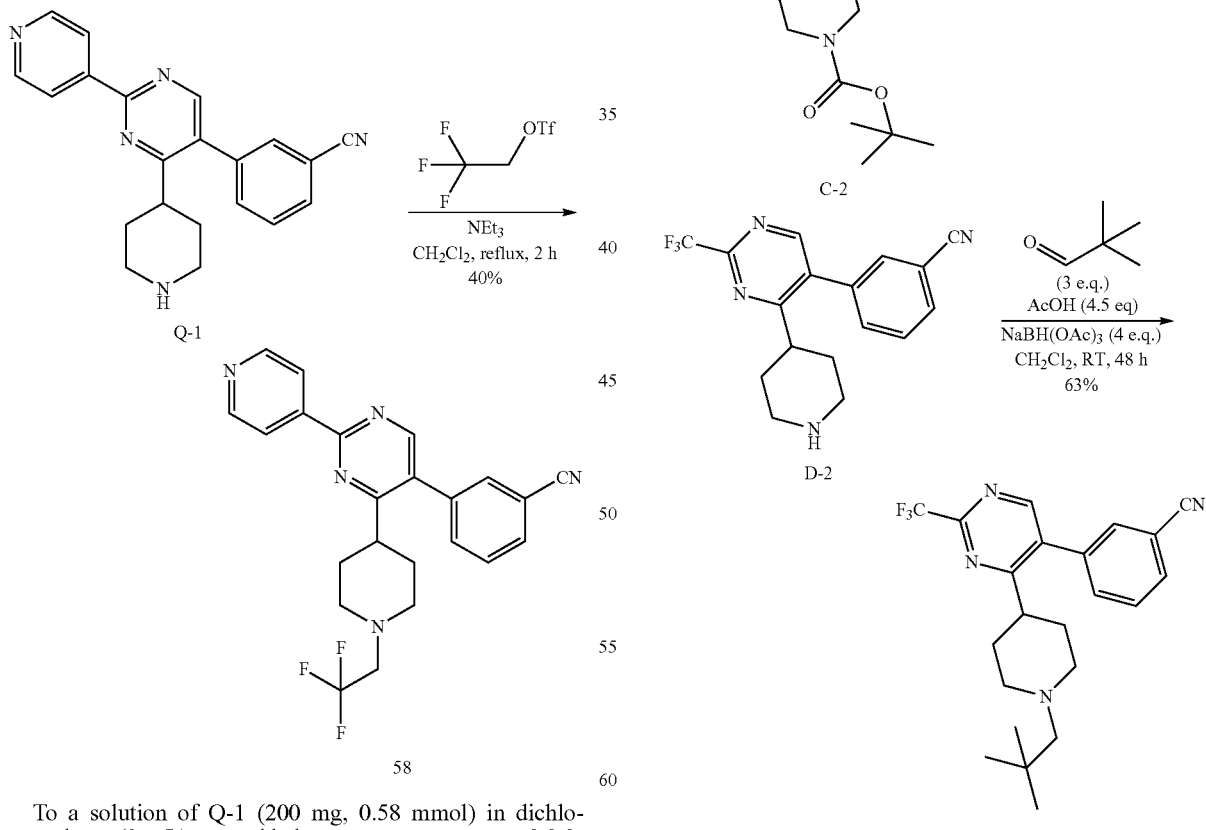

To a solution of Q-1 (200 mg, 0.58 mmol) in dichloromethane (3 mL) was added, at room temperature, 2,2,2-trifluoroethyl triflate (0.13 mL, 0.88 mmol) followed by triethylamine (0.24 mL, 1.76 mmol). The reaction mixture was then stirred at reflux for 2 hours. After 80% consumption of Q-1 (monitoring by LCMS), the reaction mixture was treated with water (5 mL). The aqueous crude mixture was extracted with dichloromethane (3×10 mL). The combined organic layers were dried over sodium sulfate, filtered and concentrated in vacuum (185 mg). The crude compound was then purified on silica gel using ethyl acetate/petroleum ether 50/50 to afford the desired compound 58 as a white solid (100 mg, 40% yield).

Synthesis of Final Compound 64:

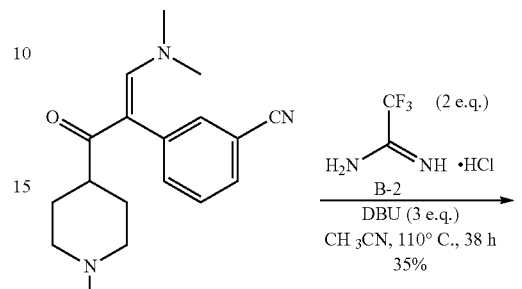

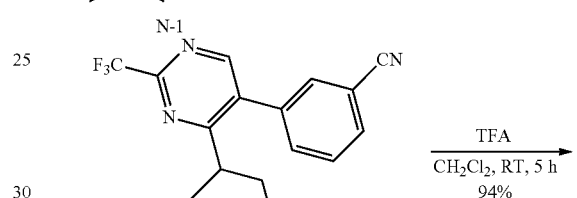

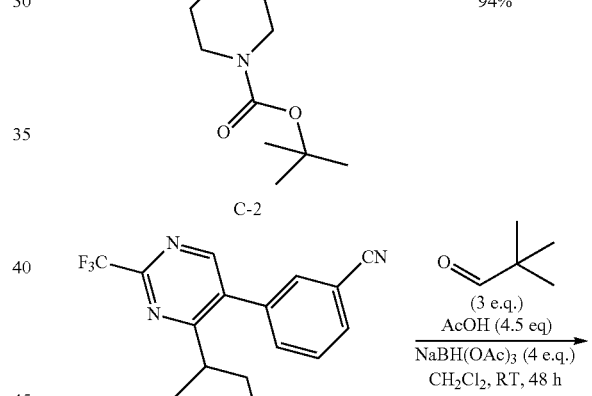

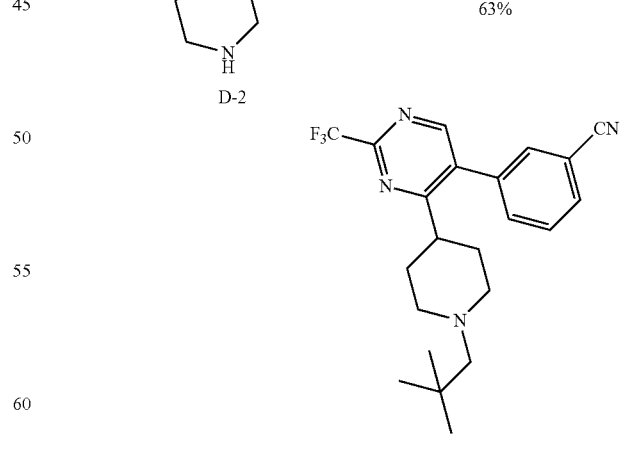

To a stirred solution of N-1 (800 mg, 2.0 mmol) in acetonitrile (8 mL) was added, at room temperature 2,2,2-trifluoroacetimidamide hydrochloride B-2 (620 mg, 4.1 mmol) followed by DBU (0.93 mL, 6.2 mmol). The reaction mixture was then heated in a sealed tube at 110° C. for 38 hours. After 54% consumption of N-1 (monitoring by LCMS), the reaction mixture was allowed to cool to room temperature, diluted with dichloromethane (30 mL) and treated with water (30 mL). The aqueous crude mixture was extracted with dichloromethane (3×30 mL). The combined organic layers were dried over sodium sulfate, filtered and concentrated in vacuum. The crude compound was then purified on silica gel using petroleum ether/ethyl acetate 70/30 to afford the desired intermediate C-2 as a light yellow solid (315 mg, 35% yield).

To a solution of C-2 (465 mg, 1.08 mmol) in dichloromethane (5 mL), trifluoroacetic acid (1 mL) was added at room temperature. The reaction mixture was then stirred at room temperature for 5 hours. After complete consumption of C-2 (monitoring by TLC), the reaction mixture was concentrated in vacuum to get a residue that was taken up in dichloromethane (30 mL) and treated with a saturated aqueous solution of potassium carbonate (30 mL). The aqueous crude mixture was extracted with dichloromethane (3×30 mL). The combined organic layers were dried over sodium sulfate, filtered and concentrated in vacuum to afford the desired intermediate D-2 as a light yellow solid (340 mg, 94% yield) which was used in the next step without any further purification.

To a solution of D-2 (340 mg, 1.02 mmol) in dichloroethane (13 mL), acetic acid (0.19 mL, 4.59 mmol) was added, at room temperature, followed by 2,2-dimethylpropanal (0.33 mL, 3.07 mmol). The reaction mixture was then stirred at room temperature for 5 hours before adding sodium triacetoxyborohydride (867 mg, 4.08 mmol). Reaction mixture was stirred at room temperature for 48 hours and then diluted with dichloromethane (30 mL) and treated with a saturated solution of sodium bicarbonate (30 mL). The aqueous layer was extracted with dichloromethane (3×40 mL). The combined organic layers were dried over sodium sulfate, filtered and concentrated in vacuum (400 mg). The crude compound was then purified on silica gel using dichloromethane/methanol/ammonium hydroxide solution (33% in H$_2$O): 99/1/0.1 to afford the desired compound 64 as a white solid (260 mg, 63% yield).

Synthesis of Final Compound 70:

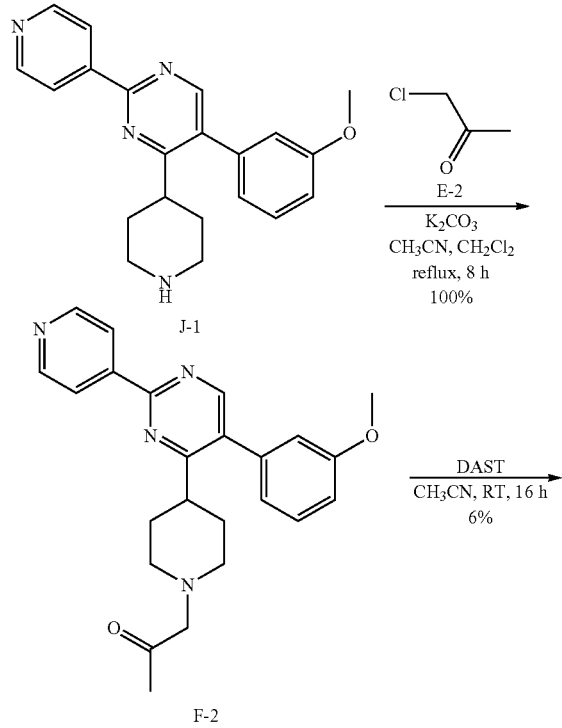

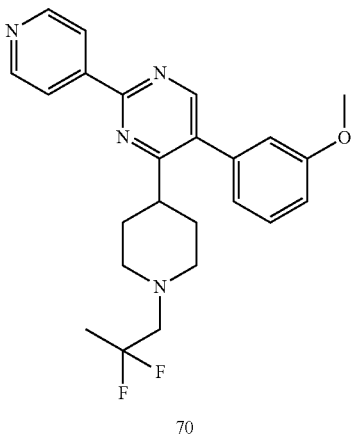

To a stirred solution of J-1 (800 mg, 2.3 mmol) in acetonitrile (9.2 mL) and dichloromethane (4.8 mL) was added, at room temperature, chloroacetone E-2 (0.27 mL, 3.45 mmol) followed by potassium carbonate (0.64 g, 4.6 mmol). The reaction mixture was then heated at reflux for 8 hours. The reaction mixture was allowed to cool to room temperature diluted with dichloromethane (30 mL) and treated with water (30 mL). The aqueous crude mixture was extracted with dichloromethane (2×30 mL). The combined organic layers were dried over sodium sulfate, filtered and concentrated in vacuum to afford the desired intermediate F-2 as a red oil (930 mg, 100% yield) which was used in the next step without any further purification.

To a solution of F-2 (930 mg, 2.3 mmol) in dichloromethane (115 mL), diethyl amino sulfur trifluoride (DAST) (0.57 mL, 6.9 mmol) was added drop wise, at −78° C. The reaction mixture was then stirred at room temperature for 16 hours. The reaction mixture was diluted with dichloromethane (50 mL) and treated with a saturated aqueous solution of sodium carbonate (50 mL), at 0° C. The aqueous crude mixture was extracted with dichloromethane (2×50 mL). The combined organic layers were dried over sodium sulfate, filtered and concentrated in vacuum. The crude compound was first purified on silica gel using dichloromethane/methanol/ammonium hydroxide solution (33% in H$_2$O): 99/1/0.1, then another purification was done using dichloro-methane/ethyl acetate: 80/20. The residue was finally triturated with pentane to afford the desired compound 70 as a brown gummy solid (60 mg, 6%).

Synthesis of Final Compound 89:

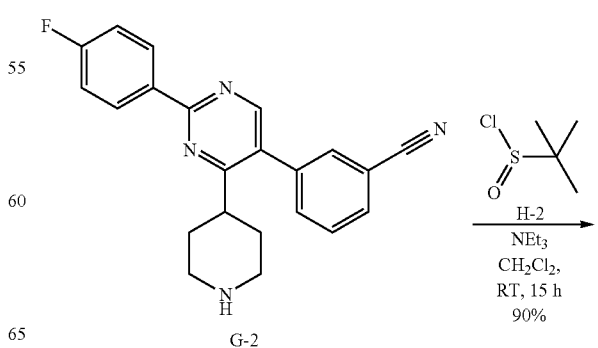

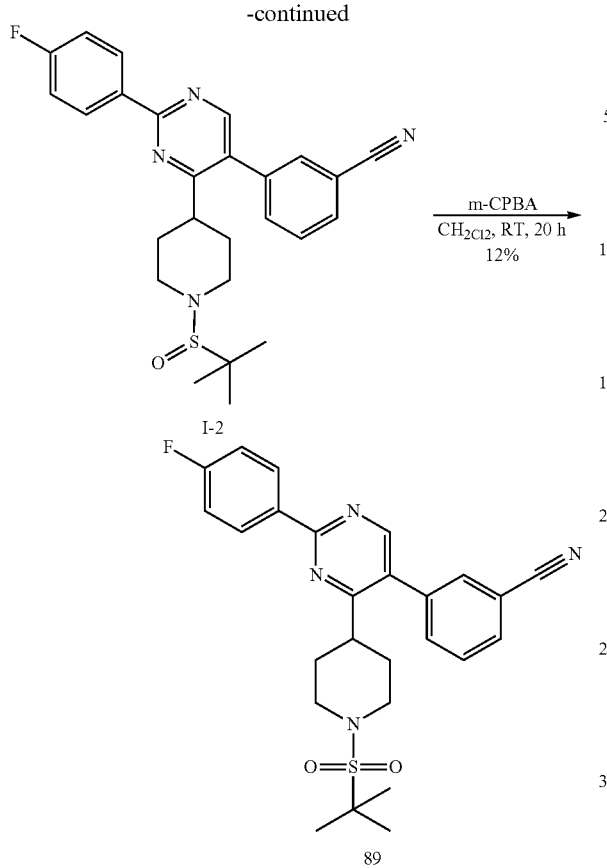

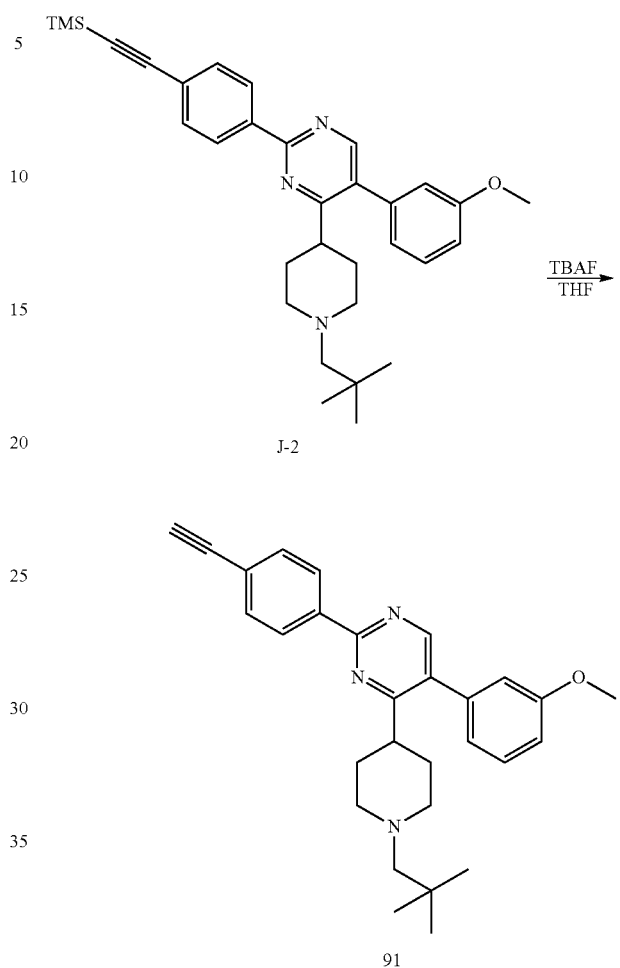

To a mixture of intermediate G-2 (0.15 g, 0.38 mmol) in dichloromethane (20 mL) was added tri-ethylamine (0.12 g, 1.14 mmol) followed by compound 1-2 (0.053 g, 0.38 mmol) at 0° C. The reaction mixture was stirred at 25° C. under $N_2$ for 15 hours. The mixture was diluted with dichloromethane and washed with saturated aqueous sodium bicarbonate. The aqueous layer is back extracted with dichloromethane. The combined organic layers were washed with brine, dried and evaporated to give intermediate I-2 (0.16 g, 90%).

To a solution of intermediate I-2 (0.16 g, 0.35 mmol) in dichloromethane (15 mL) was added m-CPBA (0.066 g, 0.38 mmol) portion wise at 0° C. The mixture was stirred at 15° C. for 20 hours. The solid was precipitated out and filtered through a pad of celite and washed with dichloromethane. The filtrate was purified by high-performance liquid chromatography to give compound 89 (16 mg, 12%).

Synthesis of Final Compound 91:

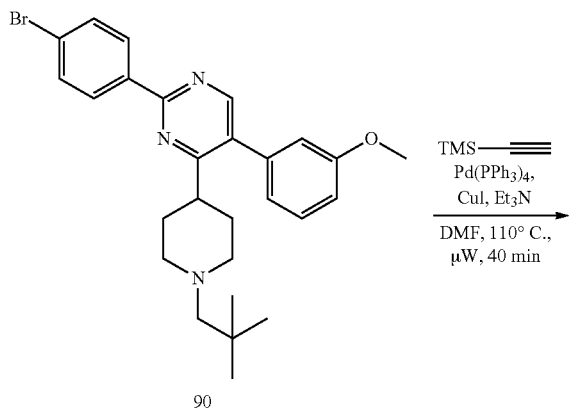

Triethylsilyl acetylene (38 mg, 0.27 mmol) was added to a solution of compound 90 (0.12 g, 0.18 mmol), Pd(PPh$_3$)$_4$ (21 mg, 0.018 mmol), tri-ethylamine (0.22 g, 2.16 mmol) and Copper(I) iodide (3 mg, 0.011 mmol) in DMF (3 mL) at room temperature under $N_2$ in a microwave vessel. The vessel was capped and irradiated at 110° C. for 40 minutes. The reaction mixture was concentrated under vacuum and the residue was diluted with ethyl acetate (30 mL) and water (10 mL). The organic layer was separated, dried over Na$_2$SO$_4$ and the solvent was removed under reduced pressure. The crude product was dried under vacuum and used directly in the next step. 0.15 g of crude intermediate J-2 was obtained.

Intermediate J2 (crude, 0.18 mmol) in dry THF (35 mL) was added to a solution of tetra-butylammonium fluoride (1 M in THF, 7.5 mL). The mixture was stirred at room temperature for 2 hours. The reaction mixture was concentrated and the crude product was directly purified by basic preparative high-performance liquid chromatography (column: C18, eluent: CH$_3$CN/H$_2$O 97/3, 0.05% NH$_3$.H$_2$O). The desired fraction was collected and the solvent was removed under reduced pressure. The product was dried under vacuum to give compound 91 (10 mg, 13%).

| # | STRUCTURE | Exact Mass | Mass Found [M + H] | LCMS Ret Time, Method | Synthesis method | MP (° C.) |
|---|---|---|---|---|---|---|
| 1 | 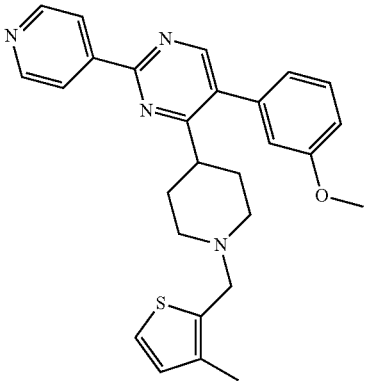 [SMILES: COc1cccc(-c2cnc(-c3ccncc3)nc2C2CCN(Cc3sccc3C)CC2)c1] | 456.20 | 457 | 1.53 B5501 | Intermediate J1 Final compound 9 | |
| 2 | 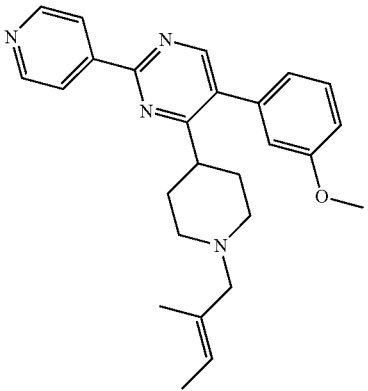 [SMILES: C/C=C(\C)CN1CCC(c2nc(-c3ccncc3)ncc2-c2cccc(OC)c2)CC1] | 414.24 | 415 | 1.46 B5501 | Intermediate J1 Final compound 9 | |
| 3 | 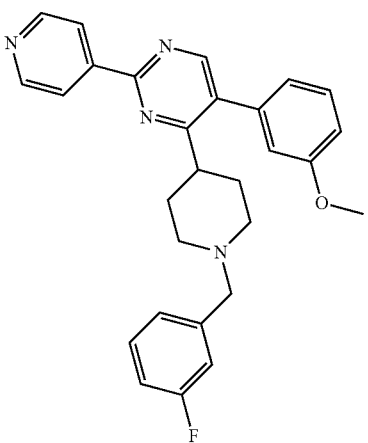 [SMILES: COc1cccc(-c2cnc(-c3ccncc3)nc2C2CCN(Cc3cccc(F)c3)CC2)c1] | 454.22 | 455 | 4.23 MERC22 | Intermediate J1 Final compound 9 | 111-114 |

-continued
| # | STRUCTURE | Exact Mass | Mass Found [M + H] | LCMS Ret Time, Method | Synthesis method | MP (° C.) |
|---|---|---|---|---|---|---|
| 4 | 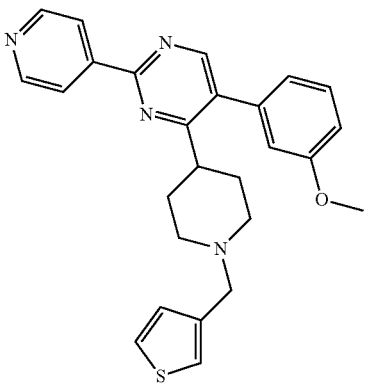 [SMILES: COc1cccc(-c2cnc(-c3ccncc3)nc2C2CCN(Cc3ccsc3)CC2)c1] | 442.18 | 443 | 4.3 V3007V3001 | Intermediate J1 Final compound 6 | 135 (K) |
| 5 | 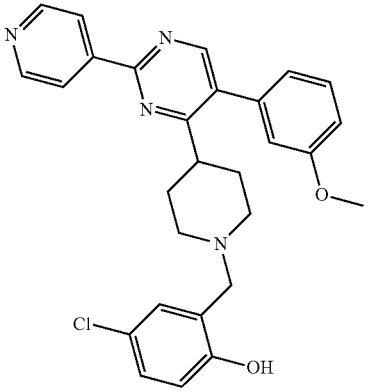 [SMILES: COc1cccc(-c2cnc(-c3ccncc3)nc2C2CCN(Cc3cc(Cl)ccc3O)CC2)c1] | 486.18 | 487 | 4.23 MERC22 | Intermediate J1 Final compound 9 | 227-228 |
| 6 | 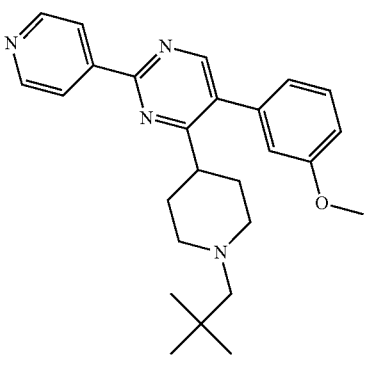 [SMILES: COc1cccc(-c2cnc(-c3ccncc3)nc2C2CCN(CC(C)(C)C)CC2)c1] | 416.26 | 417 | 5.45 V3007V3001 | Intermediate J1 Final compound 6 | 118 (K) |
| 7 | 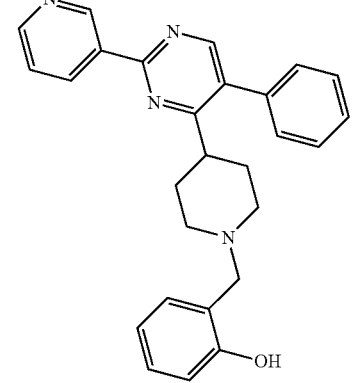 | 422.21 | 423 | 1.43 B5501 | Intermediate J1 Final compound 9 | |

| # | STRUCTURE | Exact Mass | Mass Found [M + H] | LCMS Ret Time, Method | Synthesis method | MP (° C.) |
|---|---|---|---|---|---|---|
| 8 | 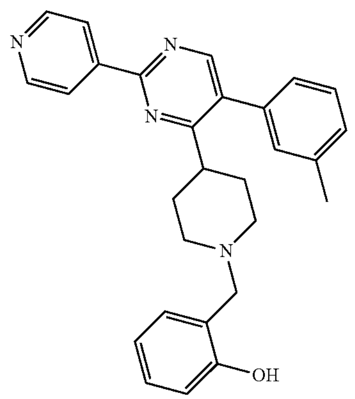 [SMILES: Cc1cccc(-c2cnc(-c3ccncc3)nc2C2CCN(Cc3ccccc3O)CC2)c1] | 436.23 | 437 | 4.47 MERC20 | Intermediate J1 Final compound 9 | 149-151 |
| 9 | 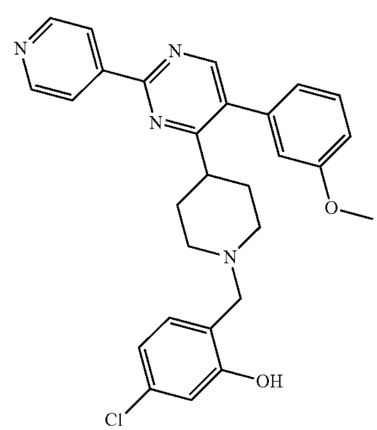 [SMILES: COc1cccc(-c2cnc(-c3ccncc3)nc2C2CCN(Cc3ccc(Cl)cc3O)CC2)c1] | 486.18 | 487 | 4.29 MERC22 | Intermediate J1 Final compound 9 | 119-123 |
| 10 | 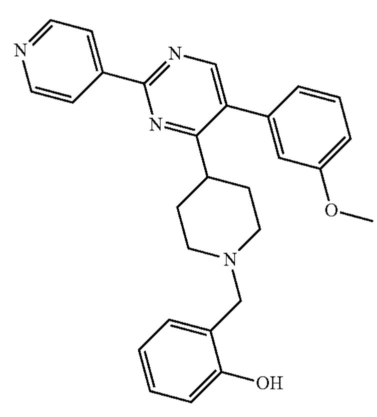 [SMILES: COc1cccc(-c2cnc(-c3ccncc3)nc2C2CCN(Cc3ccccc3O)CC2)c1] | 452.22 | 453 | 4.17 MERC22 | Intermediate J1 Final compound 9 | 142-146 |

| # | STRUCTURE | Exact Mass | Mass Found [M + H] | LCMS Ret Time, Method | Synthesis method | MP (° C.) |
|---|---|---|---|---|---|---|
| 11 | 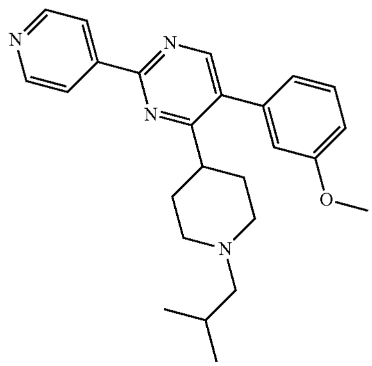 [SMILES: COc1cccc(-c2cnc(-c3ccncc3)nc2C2CCN(CC(C)C)CC2)c1] | 402.24 | 403 | 4.3 MERC22 | Intermediate J1 Final compound 6 | 105-106 |
| 12 | 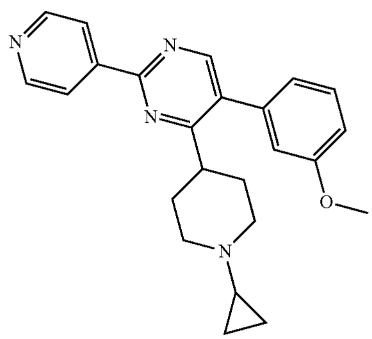 [SMILES: COc1cccc(-c2cnc(-c3ccncc3)nc2C2CCN(C3CC3)CC2)c1] | 386.21 | 387 | 4.06 MERC22 | Intermediate J1 Final compound 12 | 153-156 |
| 13 | 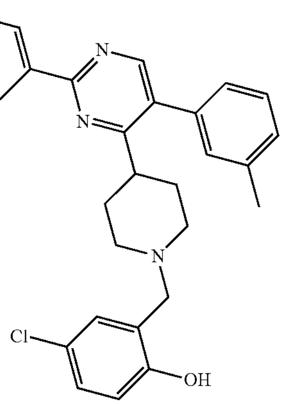 | 470.19 | 469 (M − H) | 4.42 MERC22 | Intermediate J1 Final compound 9 | 180-181 |
| 14 | 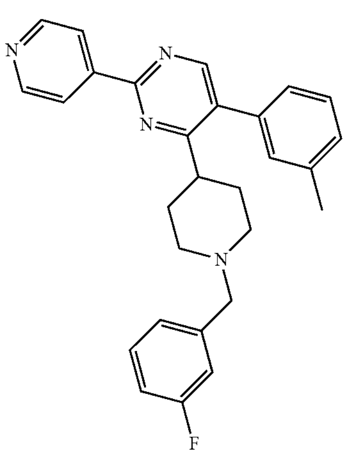 [SMILES: Cc1cccc(-c2cnc(-c3ccncc3)nc2C2CCN(Cc3cccc(F)c3)CC2)c1] | 438.22 | 439 | 4.38 MERC22 | Intermediate J1 Final compound 9 | 195-196 |

-continued

| # | STRUCTURE | Exact Mass | Mass Found [M + H] | LCMS Ret Time, Method | Synthesis method | MP (° C.) |
|---|---|---|---|---|---|---|
| 15 | 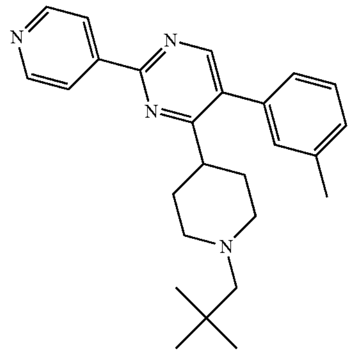 [SMILES: Cc1cccc(-c2cnc(-c3ccncc3)nc2C2CCN(CC(C)(C)C)CC2)c1] | 400.26 | 401 | 4.62 MERC22 | Intermediate J1 Final compound 6 | 123-127 |
| 16 | 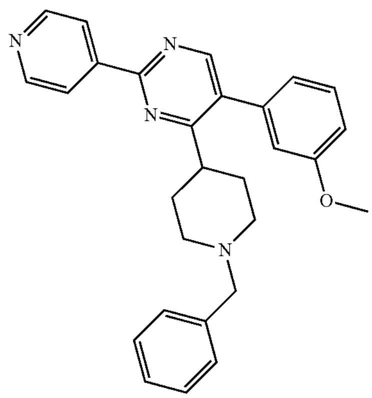 [SMILES: COc1cccc(-c2cnc(-c3ccncc3)nc2C2CCN(Cc3ccccc3)CC2)c1] | 436.23 | 437 | 4.63 V3007V3001 | Intermediate J1 Final compound 9 | 174 (K) |
| 17 | 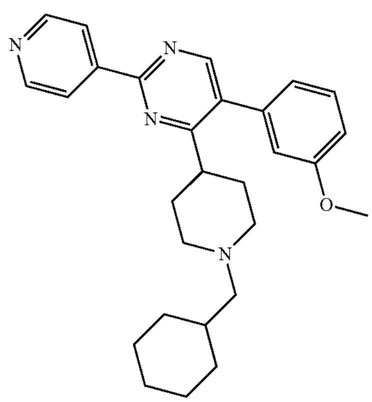 [SMILES: COc1cccc(-c2cnc(-c3ccncc3)nc2C2CCN(CC3CCCCC3)CC2)c1] | 442.27 | 443 | 4.86 V3007V3001 | Intermediate J1 Final compound 6 | 130 (K) |
| 18 | 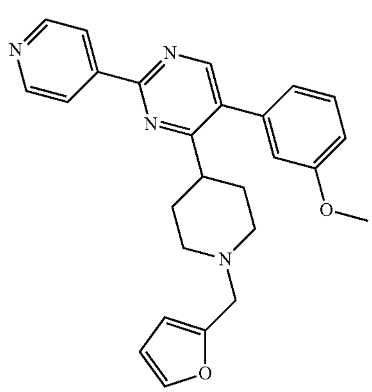 | 426.21 | 427 | 4.23 V3007V3001 | Intermediate J1 Final compound 6 | 120 (K) |

| # | STRUCTURE | Exact Mass | Mass Found [M + H] | LCMS Ret Time, Method | Synthesis method | MP (° C.) |
|---|-----------|-----------|--------------------|-----------------------|------------------|-----------|
| 19 | 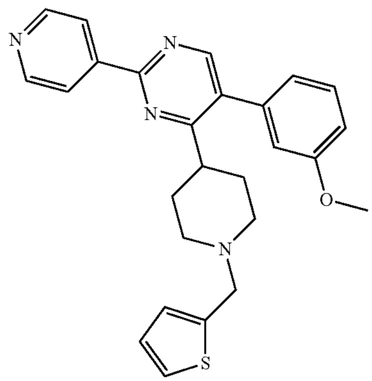 | 442.18 | 443 | 4.65 V3007V3001 | Intermediate J1 Final compound 6 | 130 (K) |
| 20 | 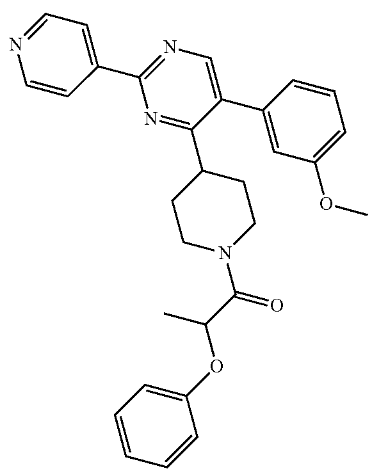 [SMILES: COc1cccc(-c2cnc(-c3ccncc3)nc2C2CCN(C(=O)C(C)Oc3ccccc3)CC2)c1] | 494.23 | 495 | 4.1 V3007V3001 | Intermediate J1 Final compound 20 | |
| 21 | 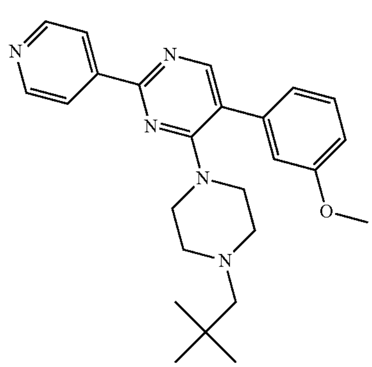 [SMILES: COc1cccc(-c2cnc(-c3ccncc3)nc2N2CCN(CC(C)(C)C)CC2)c1] | 417.25 | 418 | 4.63 MERC22 | Intermediate XI Final compound 21 | 117-120 |

-continued
| # | STRUCTURE | Exact Mass | Mass Found [M + H] | LCMS Ret Time, Method | Synthesis method | MP (° C.) |
|---|-----------|------------|--------------------|-----------------------|------------------|-----------|
| 22 | 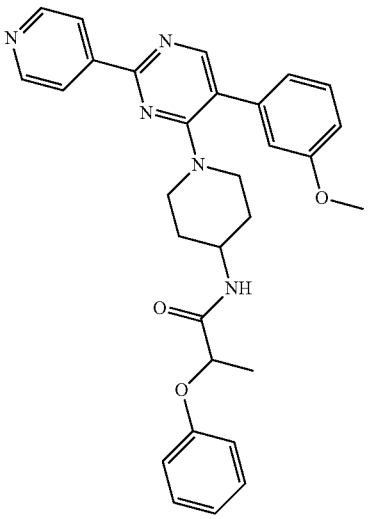 [SMILES: COc1cccc(-c2cnc(-c3ccncc3)nc2N2CCC(NC(=O)C(C)Oc3ccccc3)CC2)c1] | 509.24 | 510 | 3.19 MERC26 | Intermediate XI Final compound 21 | 106-108 |
| 23 | 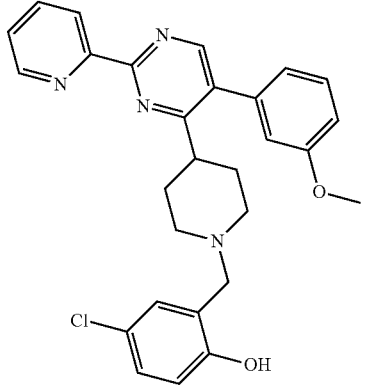 [SMILES: COc1cccc(-c2cnc(-c3ccccn3)nc2C2CCN(Cc3cc(Cl)ccc3O)CC2)c1] | 486.18 | 487 | 4.16 MERC27 | Intermediate J1 Final compound 9 | 165-166 |
| 24 | 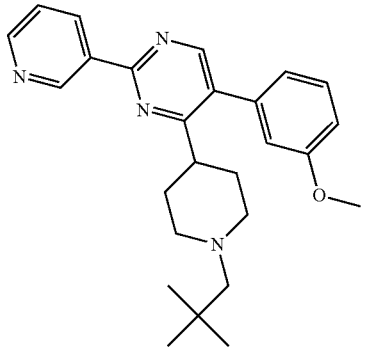 [SMILES: COc1cccc(-c2cnc(-c3cccnc3)nc2C2CCN(CC(C)(C)C)CC2)c1] | 416.26 | 417 | 4.89 MERC27 | Intermediate J1 Final compound 6 | 222-224 |

| # | STRUCTURE | Exact Mass | Mass Found [M + H] | LCMS Ret Time, Method | Synthesis method | MP (° C.) |
|---|---|---|---|---|---|---|
| 25 | 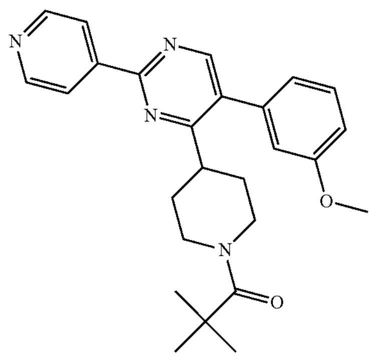 [SMILES: COc1cccc(-c2cnc(-c3ccncc3)nc2C2CCN(C(=O)C(C)(C)C)CC2)c1] | 430.24 | 431 | 4.05 V3007V3001 | Intermediate J1 Final compound 25 | 165 (K) |
| 26 | 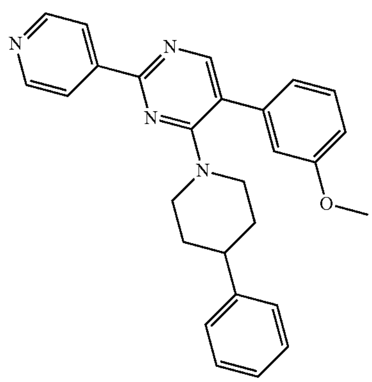 [SMILES: COc1cccc(-c2cnc(-c3ccncc3)nc2N2CCC(c3ccccc3)CC2)c1] | 422.21 | 423 | 4.4 MERC28 | Final compound 26 | 157-159 |
| 27 | 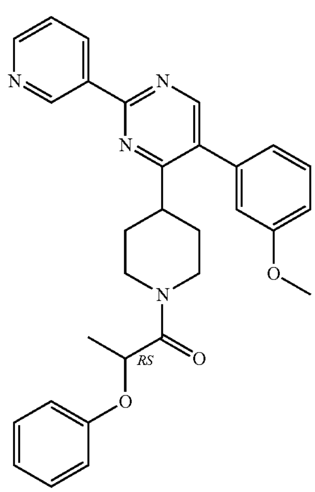 [SMILES: COc1cccc(-c2cnc(-c3cccnc3)nc2C2CCN(C(=O)C(C)Oc3ccccc3)CC2)c1] | 494.23 | 495 | 3.77 MERC28 | Intermediate J1 Final compound 20 | 138-140 |

| # | STRUCTURE | Exact Mass | Mass Found [M + H] | LCMS Ret Time, Method | Synthesis method | MP (° C.) |
|---|---|---|---|---|---|---|
| 28 | 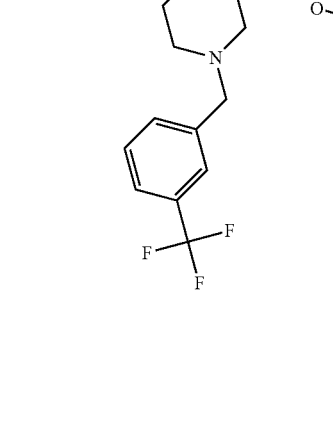 | 504.21 | 505 | 5.08 V3007V3001 | Intermediate J1 Final compound 6 | 156 (K) |
| 29 | 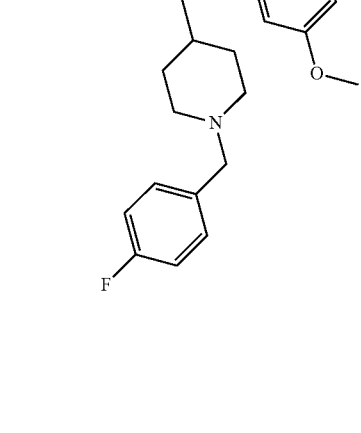 | 454.22 | 455 | 4.67 V3007V3001 | Intermediate J1 Final compound 6 | 152 (K) |
| 30 | 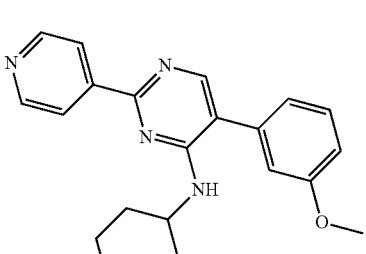 | 431.27 | 432 | 4.86 MERC27 | Final compound 26 | 137-138 |

-continued
| # | STRUCTURE | Exact Mass | Mass Found [M + H] | LCMS Ret Time, Method | Synthesis method | MP (° C.) |
|---|-----------|------------|--------------------|-----------------------|------------------|-----------|
| 31 | 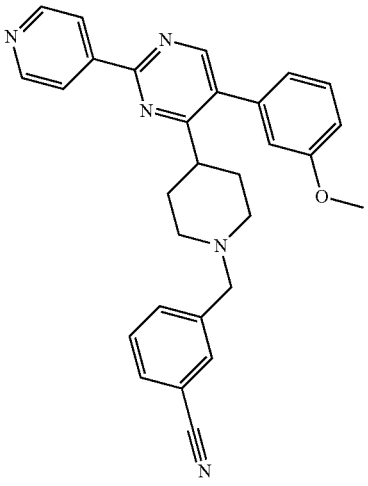 [SMILES: COc1cccc(-c2cnc(-c3ccncc3)nc2C2CCN(Cc3cccc(C#N)c3)CC2)c1] | 461.22 | 462 | 4.5 V3007V3001 | Intermediate J1 Final compound 6 | 140 (K) |
| 32 | 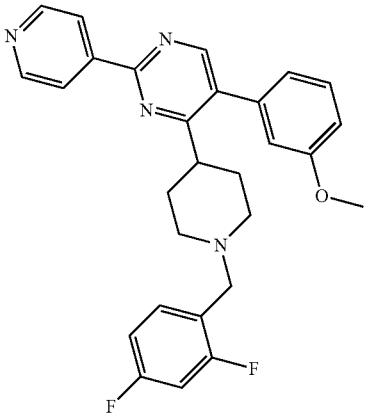 [SMILES: COc1cccc(-c2cnc(-c3ccncc3)nc2C2CCN(Cc3ccc(F)cc3F)CC2)c1] | 472.21 | 473 | 4.82 V3007V3001 | Intermediate J1 Final compound 6 | 138 (K) |
| 33 | 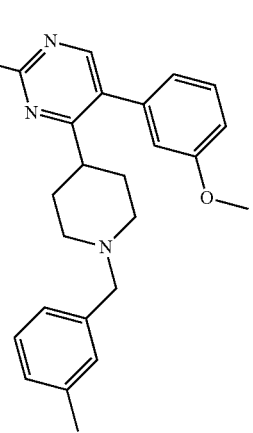 | 450.24 | 451 | 4.86 V3007V3001 | Intermediate J1 Final compound 6 | 160 (K) |

| # | STRUCTURE | Exact Mass | Mass Found [M + H] | LCMS Ret Time, Method | Synthesis method | MP (° C.) |
|---|---|---|---|---|---|---|
| 34 | 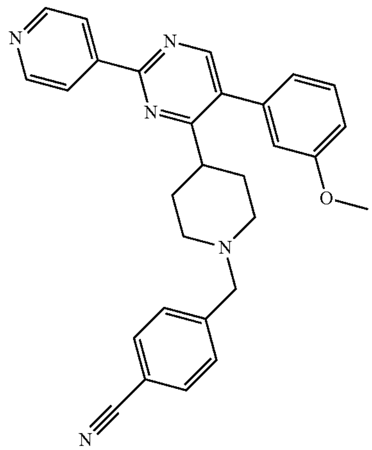 [SMILES: COc1cccc(-c2cnc(-c3ccncc3)nc2C2CCN(Cc3ccc(C#N)cc3)CC2)c1] | 461.22 | 462 | 4.5 V3007V3001 | Intermediate J1 Final compound 6 | 168 (K) |
| 35 | 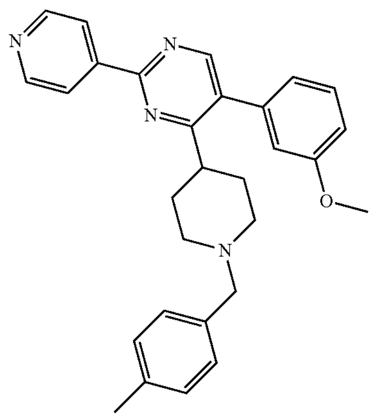 [SMILES: COc1cccc(-c2cnc(-c3ccncc3)nc2C2CCN(Cc3ccc(C)cc3)CC2)c1] | 450.24 | 451 | 4.77 V3007V3001 | Intermediate J1 Final compound 6 | 141 (K) |
| 36 | 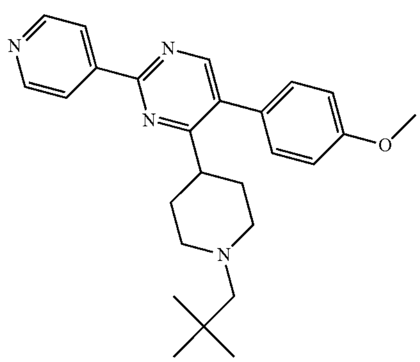 [SMILES: COc1ccc(-c2cnc(-c3ccncc3)nc2C2CCN(CC(C)(C)C)CC2)cc1] | 416.26 | 417 | 4.95 MERC25 | Intermediate J1 Final compound 6 | 154-156 |
| 37 | 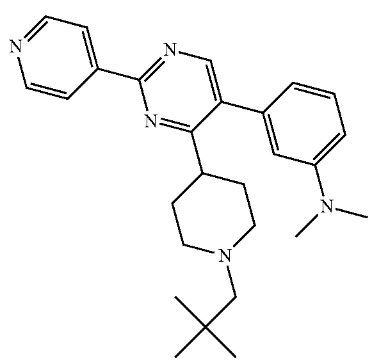 [SMILES: CN(C)c1cccc(-c2cnc(-c3ccncc3)nc2C2CCN(CC(C)(C)C)CC2)c1] | 429.29 | 430 | 5.22 MERC30 | Intermediate J1 Final compound 6 | 140-142 |

-continued

| # | STRUCTURE | Exact Mass | Mass Found [M + H] | LCMS Ret Time, Method | Synthesis method | MP (° C.) |
|---|---|---|---|---|---|---|
| 38 | 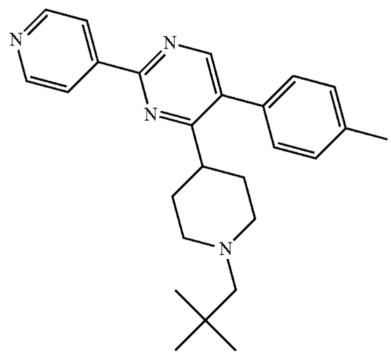 [SMILES: Cc1ccc(-c2cnc(-c3ccncc3)nc2C2CCN(CC(C)(C)C)CC2)cc1] | 400.26 | 401 | 5.6 MERC27 | Intermediate J1 Final compound 6 | 170-171 |
| 39 | 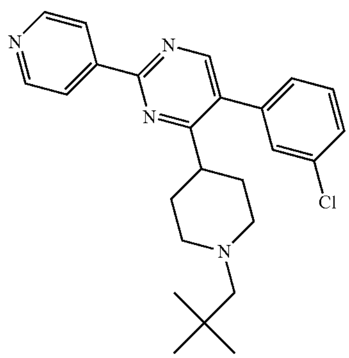 [SMILES: CC(C)(C)CN1CCC(c2nc(-c3ccncc3)ncc2-c2cccc(Cl)c2)CC1] | 420.21 | 421 | 5.48 MERC27 | Intermediate J1 Final compound 6 | 119-121 |
| 40 | 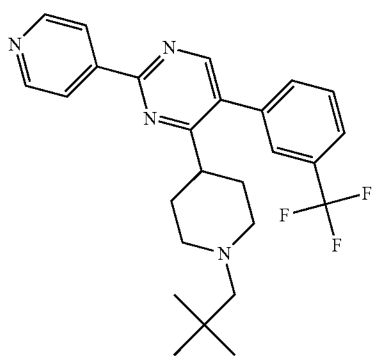 [SMILES: CC(C)(C)CN1CCC(c2nc(-c3ccncc3)ncc2-c2cccc(C(F)(F)F)c2)CC1] | 454.23 | 455 | 5.32 MERC27 | Intermediate J1 Final compound 6 | 112-114 |
| 41 | 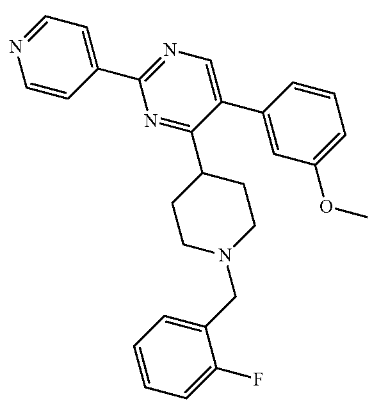 [SMILES: COc1cccc(-c2cnc(-c3ccncc3)nc2C2CCN(Cc3ccccc3F)CC2)c1] | 454.22 | 455 | 4.74 V3007V3001 | Intermediate J1 Final compound 6 | 139 (K) |

-continued

| # | STRUCTURE | Exact Mass | Mass Found [M + H] | LCMS Ret Time, Method | Synthesis method | MP (° C.) |
|---|---|---|---|---|---|---|
| 42 | 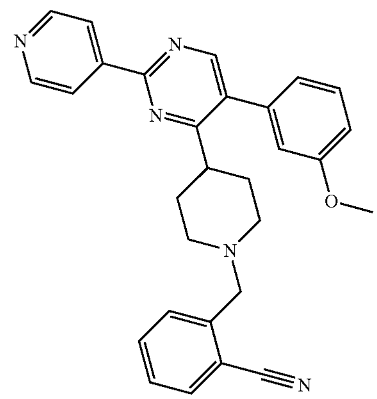 [SMILES: COc1cccc(-c2cnc(-c3ccncc3)nc2C2CCN(Cc3ccccc3C#N)CC2)c1] | 461.22 | 462 | 4.57 V3007V3001 | Intermediate J1 Final compound 6 | 158 (K) |
| 43 | 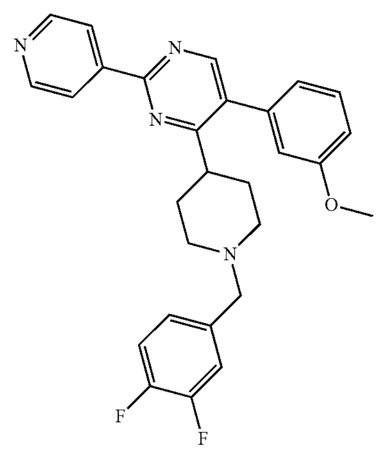 [SMILES: COc1cccc(-c2cnc(-c3ccncc3)nc2C2CCN(Cc3ccc(F)c(F)c3)CC2)c1] | 472.21 | 473 | 4.87 V3007V3001 | Intermediate J1 Final compound 6 | 158 (K) |
| 44 | 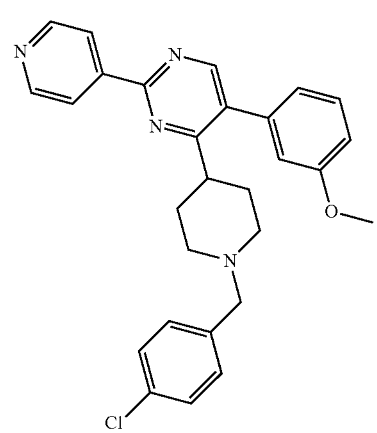 [SMILES: COc1cccc(-c2cnc(-c3ccncc3)nc2C2CCN(Cc3ccc(Cl)cc3)CC2)c1] | 470.19 | 471 | 5.09 V3007V3001 | Intermediate J1 Final compound 6 | 131 (K) |

| # | STRUCTURE | Exact Mass | Mass Found [M + H] | LCMS Ret Time, Method | Synthesis method | MP (° C.) |
|---|---|---|---|---|---|---|
| 45 | 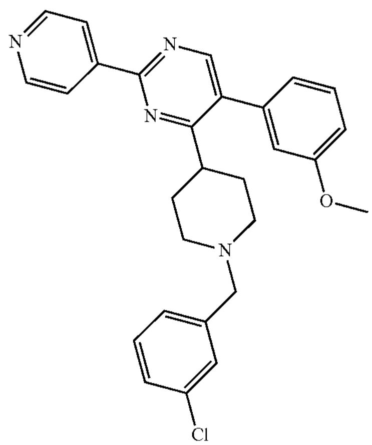 [SMILES: COc1cccc(-c2cnc(-c3ccncc3)nc2C2CCN(Cc3cccc(Cl)c3)CC2)c1] | 470.19 | 471 | 5.15 V3007V3001 | Intermediate J1 Final compound 6 | 133 (K) |
| 46 | 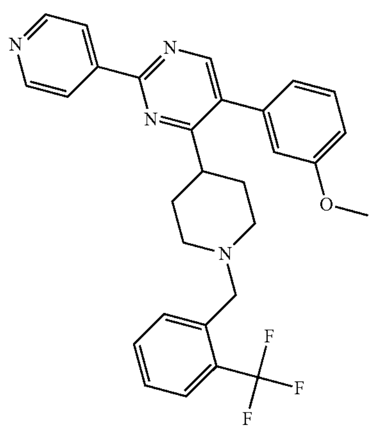 [SMILES: COc1cccc(-c2cnc(-c3ccncc3)nc2C2CCN(Cc3ccccc3C(F)(F)F)CC2)c1] | 504.21 | 505 | 5.38 V3007V3001 | Intermediate J1 Final compound 6 | 144 (K) |
| 47 | 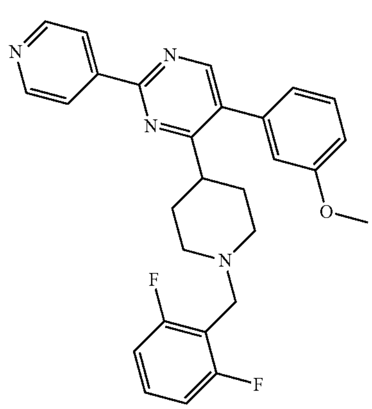 [SMILES: COc1cccc(-c2cnc(-c3ccncc3)nc2C2CCN(Cc3c(F)cccc3F)CC2)c1] | 472.21 | 473 | 4.99 V3007V3001 | Intermediate J1 Final compound 6 | 184 (K) |

| # | STRUCTURE | Exact Mass | Mass Found [M + H] | LCMS Ret Time, Method | Synthesis method | MP (° C.) |
|---|---|---|---|---|---|---|
| 48 | 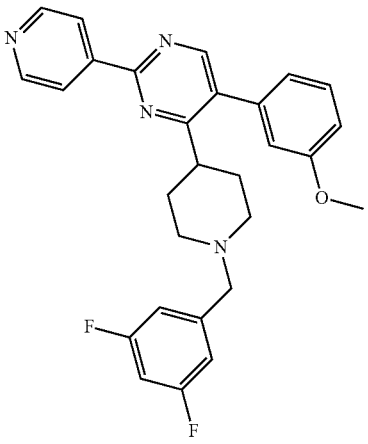 [SMILES: COc1cccc(-c2cnc(-c3ccncc3)nc2C2CCN(Cc3cc(F)cc(F)c3)CC2)c1] | 472.21 | 473 | 4.99 V3007V3001 | Intermediate J1 Final compound 6 | 181 (K) |
| 49 | 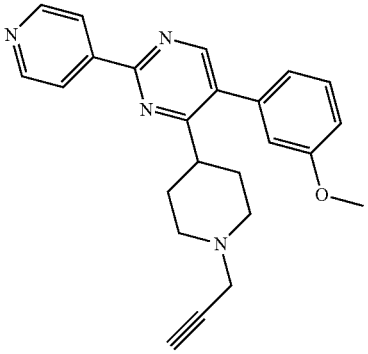 [SMILES: C#CCN1CCC(c2nc(-c3ccncc3)ncc2-c2cccc(OC)c2)CC1] | 384.20 | 385 | 3.92 V3007V3001 | Intermediate J1 Final compound 49 | 160 (K) |
| 50 | 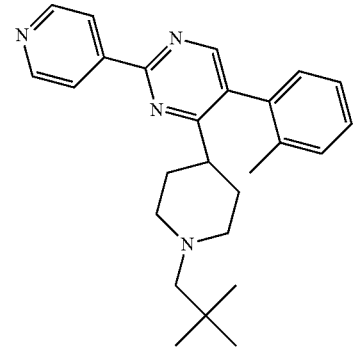 [SMILES: Cc1ccccc1-c1cnc(-c2ccncc2)nc1C1CCN(CC(C)(C)C)CC1] | 400.26 | 401 | 5.91 V3007V3001 | Intermediate J1 Final compound 6 | 208 (K) |
| 51 | 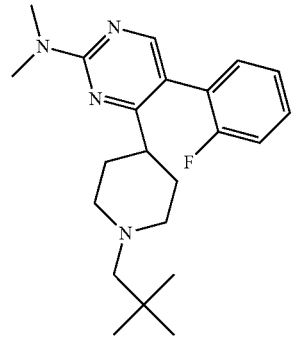 [SMILES: CN(C)c1ncc(-c2ccccc2F)c(C2CCN(CC(C)(C)C)CC2)n1] | 370.25 | 371 | 6.08 B5301 | — | |

-continued
| # | STRUCTURE | Exact Mass | Mass Found [M + H] | LCMS Ret Time, Method | Synthesis method | MP (° C.) |
|---|---|---|---|---|---|---|
| 52 | 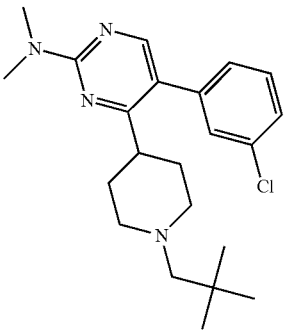 [SMILES: CN(C)c1ncc(-c2cccc(Cl)c2)c(C2CCN(CC(C)(C)C)CC2)n1] | 386.22 | 387 | 6.65 B5301 | — | |
| 53 | 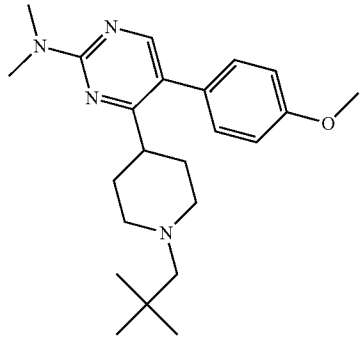 | 382.27 | 383 | 5.85 B5301 | — | |
| 54 | 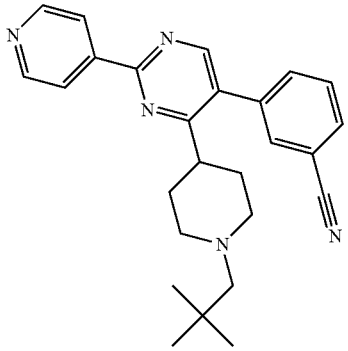 [SMILES: CC(C)(C)CN1CCC(c2nc(-c3ccncc3)ncc2-c2cccc(C#N)c2)CC1] | 411.24 | 412 | 4.7 V3007V3001 | Intermediate Q1 Final compound 6 | 155 (K) |
| 55 | 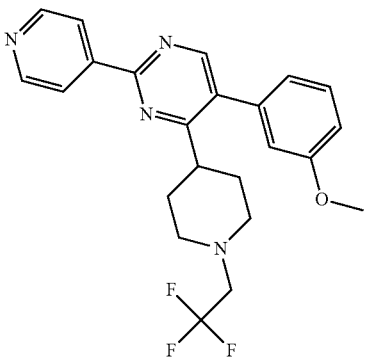 [SMILES: COc1cccc(-c2cnc(-c3ccncc3)nc2C2CCN(CC(F)(F)F)CC2)c1] | 428.18 | 429 | 4.49 V3007V3001 | Intermediate J1 Final compound 55 | |

| # | STRUCTURE | Exact Mass | Mass Found [M + H] | LCMS Ret Time, Method | Synthesis method | MP (° C.) |
|---|---|---|---|---|---|---|
| 56 | 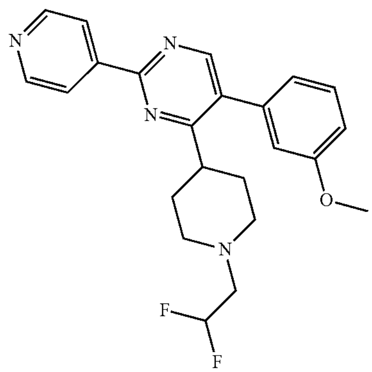 [SMILES: COc1cccc(-c2cnc(-c3ccncc3)nc2C2CCN(CC(F)F)CC2)c1] | 410.19 | 411 | 11.52 NOVA1 | Intermediate J1 Final compound 56 | 123 (B) |
| 57 | 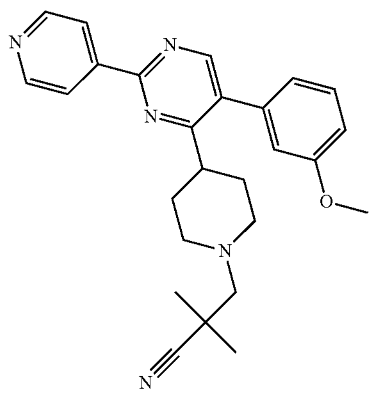 [SMILES: COc1cccc(-c2cnc(-c3ccncc3)nc2C2CCN(CC(C)(C)C#N)CC2)c1] | 427.24 | 428 | 11.77 NOVA1 | Intermediate J1 Final compound 57 | 117 (B) |
| 58 | 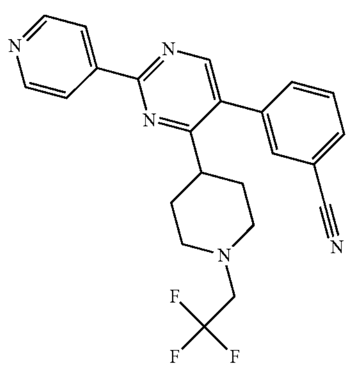 [SMILES: N#Cc1cccc(-c2cnc(-c3ccncc3)nc2C2CCN(CC(F)(F)F)CC2)c1] | 423.17 | 424 | 11.73 NOVA1 | Intermediate Q1 Final compound 58 | 168-172 (B) |
| 59 | 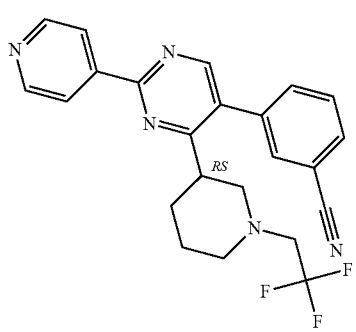 [SMILES: N#Cc1cccc(-c2cnc(-c3ccncc3)nc2C2CCCN(CC(F)(F)F)C2)c1] | 423.17 | 424 | 12.3 NOVA1 | Intermediate Q1 Final compound 58 | 163-164 (B) |

| # | STRUCTURE | Exact Mass | Mass Found [M + H] | LCMS Ret Time, Method | Synthesis method | MP (° C.) |
|---|---|---|---|---|---|---|
| 60 | 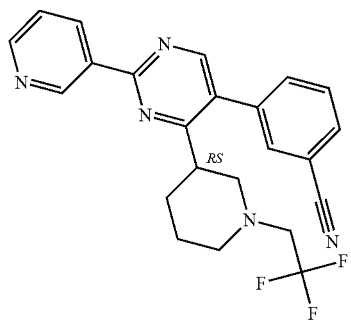 [SMILES: N#Cc1cccc(-c2cnc(-c3cccnc3)nc2C2CCCN(CC(F)(F)F)C2)c1] | 423.17 | 424 | 12.46 NOVA1 | Intermediate Q1 Final compound 58 | 52-92 (B) |
| 61 | 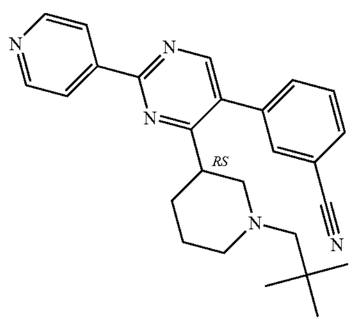 [SMILES: CC(C)(C)CN1CCCC(c2nc(-c3ccncc3)ncc2-c2cccc(C#N)c2)C1] | 411.24 | 412 | 11.74 NOVA1 | Intermediate Q1 Final compound 6 | 65-153 (B) |
| 62 | 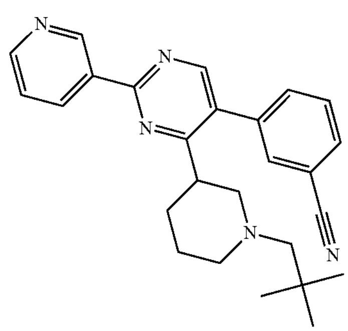 [SMILES: CC(C)(C)CN1CCCC(c2nc(-c3cccnc3)ncc2-c2cccc(C#N)c2)C1] | 411.24 | 412 | 11.98 NOVA1 | Intermediate Q1 Final compound 6 | 57-113 (B) |
| 63 | 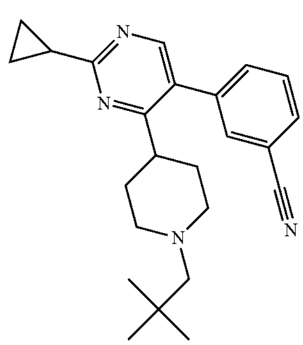 [SMILES: CC(C)(C)CN1CCC(c2nc(C3CC3)ncc2-c2cccc(C#N)c2)CC1] | 374.25 | 375 | 13.38 NOVA1 | Final compound 64 | 125-126 (B) |

-continued

| # | STRUCTURE | Exact Mass | Mass Found [M + H] | LCMS Ret Time, Method | Synthesis method | MP (° C.) |
|---|---|---|---|---|---|---|
| 64 | 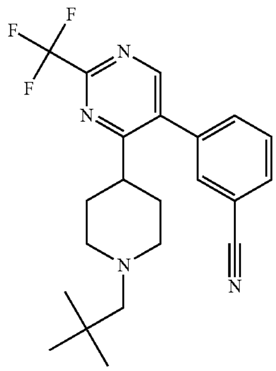 [SMILES: CC(C)(C)CN1CCC(c2nc(C(F)(F)F)ncc2-c2cccc(C#N)c2)CC1] | 402.20 | 403 | 13.63 NOVA1 | Final compound 64 | 114-116 (B) |
| 65 | 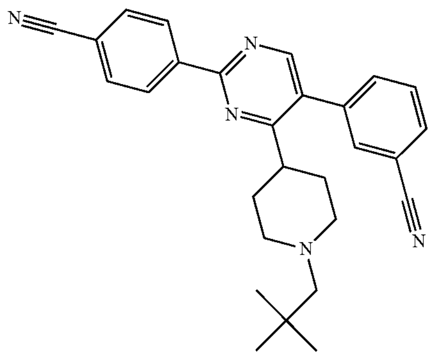 [SMILES: CC(C)(C)CN1CCC(c2nc(-c3ccc(C#N)cc3)ncc2-c2cccc(C#N)c2)CC1] | 435.24 | 436 | 14.25 NOVA1 | Intermediate Q1 Final compound 6 | 247-249 (B) |
| 66 | 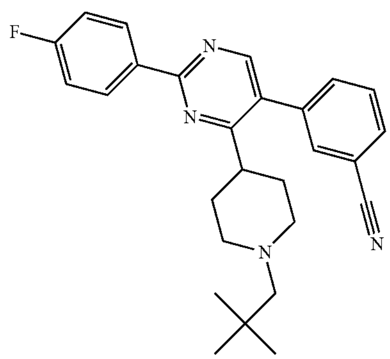 [SMILES: CC(C)(C)CN1CCC(c2nc(-c3ccc(F)cc3)ncc2-c2cccc(C#N)c2)CC1] | 428.24 | 429 | 14.62 NOVA1 | Intermediate Q1 Final compound 6 | 154-158 (B) |
| 67 | 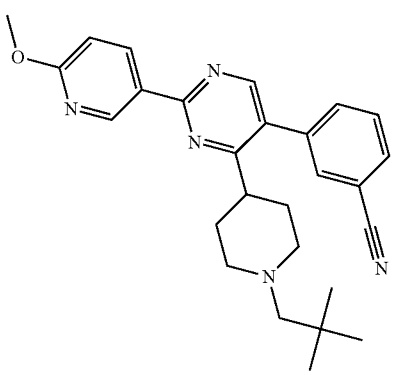 [SMILES: COc1ccc(-c2ncc(-c3cccc(C#N)c3)c(C3CCN(CC(C)(C)C)CC3)n2)cn1] | 441.25 | 442 | 14.14 NOVA1 | Intermediate Q1 Final compound 6 | 144-145 (B) |

-continued

| # | STRUCTURE | Exact Mass | Mass Found [M + H] | LCMS Ret Time, Method | Synthesis method | MP (° C.) |
|---|---|---|---|---|---|---|
| 68 | 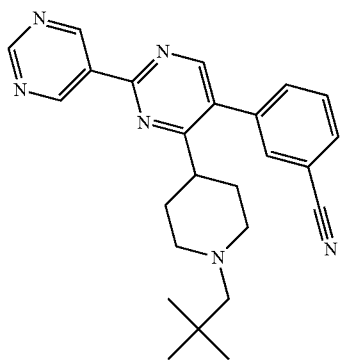 [SMILES: CC(C)(C)CN1CCC(c2nc(-c3cncnc3)ncc2-c2cccc(C#N)c2)CC1] | 412.24 | 413 | 13.13 NOVA1 | Intermediate Q1 Final compound 6 | 163-170 (B) |
| 69 | 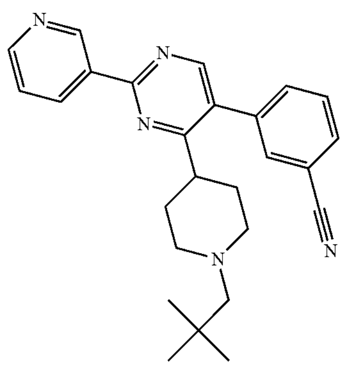 [SMILES: CC(C)(C)CN1CCC(c2nc(-c3cccnc3)ncc2-c2cccc(C#N)c2)CC1] | 411.24 | 412 | 11.88 NOVA1 | Intermediate Q1 Final compound 6 | 148-150 (B) |
| 70 | 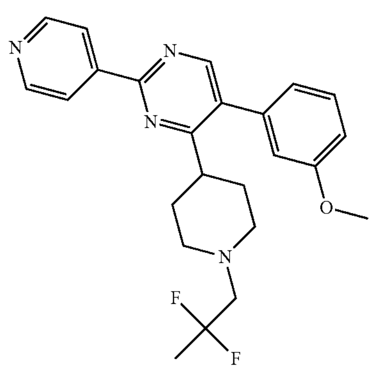 [SMILES: COc1cccc(-c2cnc(-c3ccncc3)nc2C2CCN(CC(C)(F)F)CC2)c1] | 424.21 | 425 | 11.7 NOVA1 | Intermediate J1 Final compound 70 | |
| 71 | 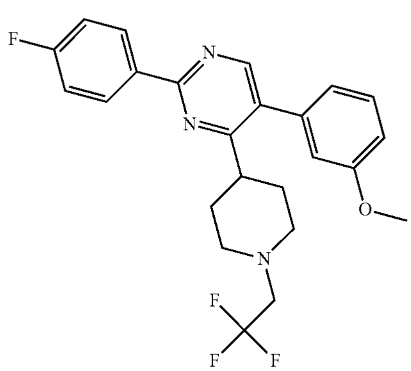 [SMILES: COc1cccc(-c2cnc(-c3ccc(F)cc3)nc2C2CCN(CC(F)(F)F)CC2)c1] | 445.18 | 446 | 4.95 WUXI2 | Intermediate J1 Final compound 58 | |

| # | STRUCTURE | Exact Mass | Mass Found [M + H] | LCMS Ret Time, Method | Synthesis method | MP (° C.) |
|---|---|---|---|---|---|---|
| 72 | 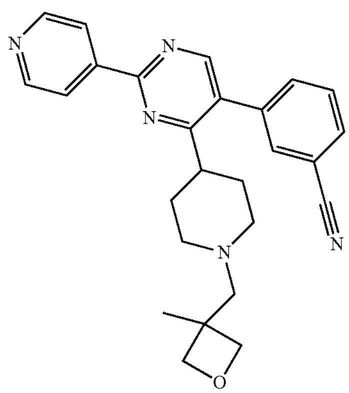 [SMILES: CC1(CN2CCC(c3nc(-c4ccncc4)ncc3-c3cccc(C#N)c3)CC2)COC1] | 425.22 | 426 | 3.7 WUXI1 | Intermediate Q1 Final compound 6 | |
| 73 | 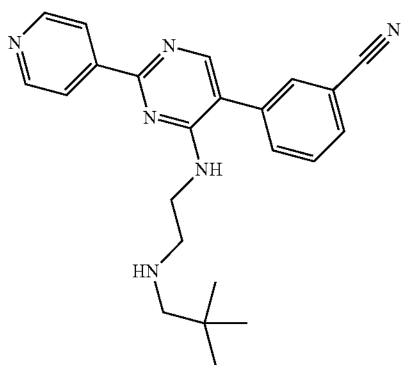 [SMILES: CC(C)(C)CNCCNc1nc(-c2ccncc2)ncc1-c1cccc(C#N)c1] | 386.22 | 387 | 2.85 WUXI2 | Intermediate XI Final compound 21 | |
| 74 | 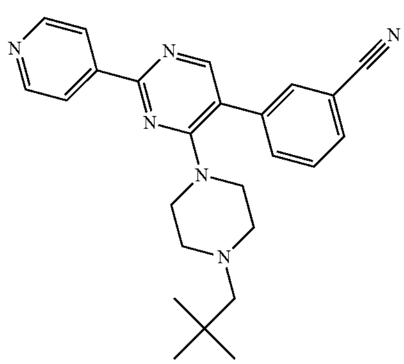 [SMILES: CC(C)(C)CN1CCN(c2nc(-c3ccncc3)ncc2-c2cccc(C#N)c2)CC1] | 412.24 | 413 | 2.7 WUXI2 | Intermediate X1 Final compound 21 | 155-164 (WRS-2A) |
| 75 | 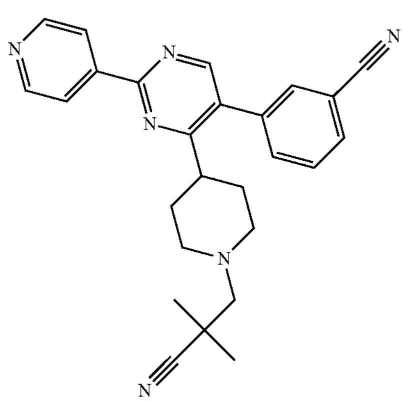 [SMILES: CC(C)(C#N)CN1CCC(c2nc(-c3ccncc3)ncc2-c2cccc(C#N)c2)CC1] | 422.22 | 423 | 3.82 WUXI1 | Intermediate Q1 Final compound 57 | 79-87 (WRS-2A) |

-continued

| # | STRUCTURE | Exact Mass | Mass Found [M + H] | LCMS Ret Time, Method | Synthesis method | MP (° C.) |
|---|---|---|---|---|---|---|
| 76 | 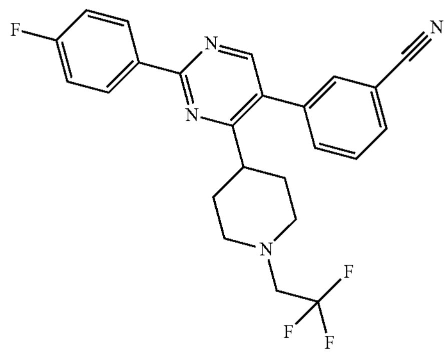 [SMILES: N#Cc1cccc(-c2cnc(-c3ccc(F)cc3)nc2C2CCN(CC(F)(F)F)CC2)c1] | 440.16 | 441 | 4.64 WUXI2 | Intermediate Q1 Final compound 58 | 157-158 (WRS-2A) |
| 77 | 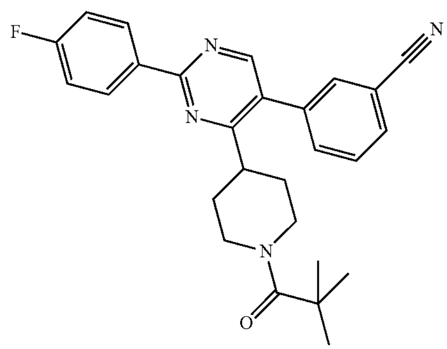 [SMILES: CC(C)(C)C(=O)N1CCC(c2nc(-c3ccc(F)cc3)ncc2-c2cccc(C#N)c2)CC1] | 442.22 | 443 | 6.72 WUXI1 | Intermediate Q1 Final compound 25 | 75-80 (WRS-2A) |
| 78 | 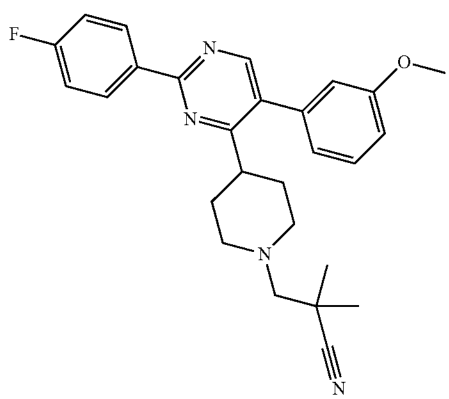 [SMILES: COc1cccc(-c2cnc(-c3ccc(F)cc3)nc2C2CCN(CC(C)(C)C#N)CC2)c1] | 444.23 | 445 | 4.04 WUXI2 | Intermediate J1 Final compound 57 | 119 (WRS-2A) |
| 79 | 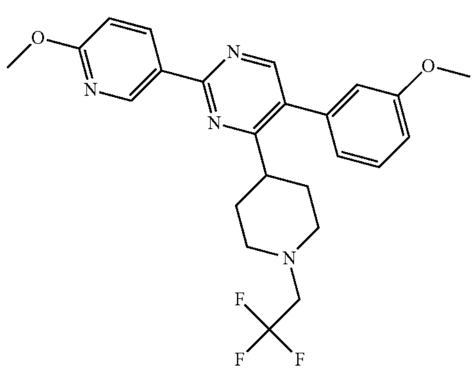 | 458.19 | 459 | 4.5 WUXI2 | Intermediate J1 Final compound 58 | |

-continued

| # | STRUCTURE | Exact Mass | Mass Found [M + H] | LCMS Ret Time, Method | Synthesis method | MP (° C.) |
|---|---|---|---|---|---|---|
| 80 | 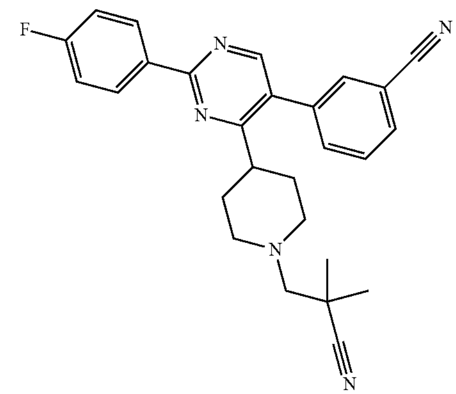 [SMILES: CC(C)(C#N)CN1CCC(c2nc(-c3ccc(F)cc3)ncc2-c2cccc(C#N)c2)CC1] | 439.22 | 440 | 3.91 WUXI2 | Intermediate Q1 Final compound 57 | 171 (WRS-2A) |
| 81 | 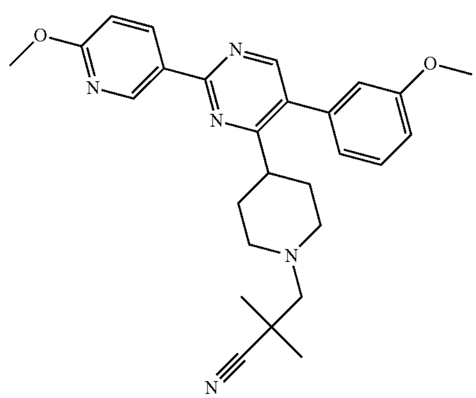 | 457.25 | 458 | 3.47 WUXI14 | Intermediate J1 Final compound 57 | |
| 82 | 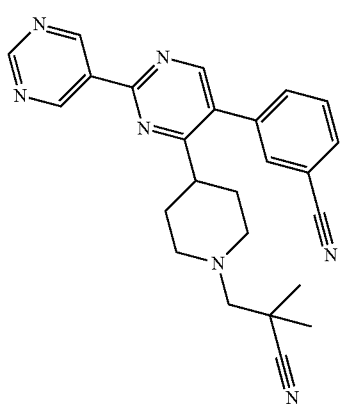 [SMILES: CC(C)(C#N)CN1CCC(c2nc(-c3cncnc3)ncc2-c2cccc(C#N)c2)CC1] | 423.22 | 424 | 4.23 WUXI1 | Intermediate Q1 Final compound 57 | 182 (WRS-2A) |
| 83 | 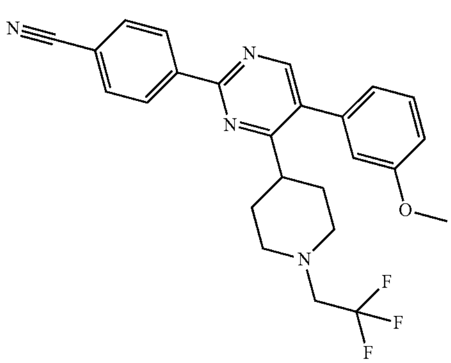 [SMILES: COc1cccc(-c2cnc(-c3ccc(C#N)cc3)nc2C2CCN(CC(F)(F)F)CC2)c1] | 452.18 | 453 | 4.69 WUXI2 | Intermediate J1 Final compound 58 | 180-182 (WRS-2A) |

-continued

| # | STRUCTURE | Exact Mass | Mass Found [M + H] | LCMS Ret Time, Method | Synthesis method | MP (° C.) |
|---|---|---|---|---|---|---|
| 84 | 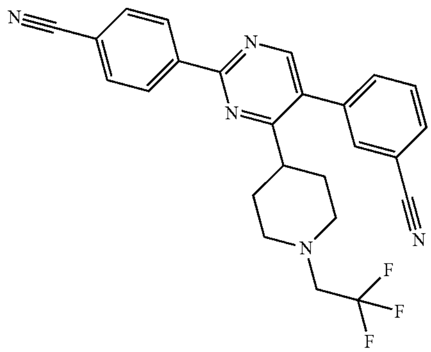 [SMILES: N#Cc1ccc(-c2ncc(-c3cccc(C#N)c3)c(C3CCN(CC(F)(F)F)CC3)n2)cc1] | 447.17 | 448 | 4.45 WUXI2 | Intermediate Q1 Final compound 58 | 249-251 (WRS-2A) |
| 85 | 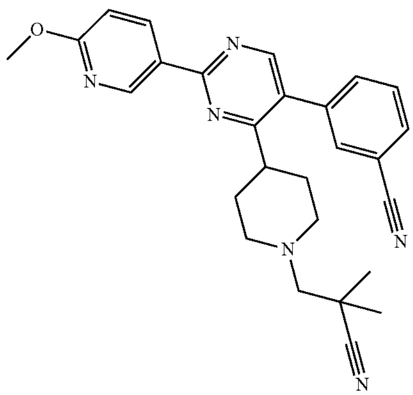 [SMILES: COc1ccc(-c2ncc(-c3cccc(C#N)c3)c(C3CCN(CC(C)(C)C#N)CC3)n2)cn1] | 452.23 | 453 | 4.85 WUXI1 | Intermediate Q1 Final compound 57 | 165 (WRS-2A) |
| 86 | 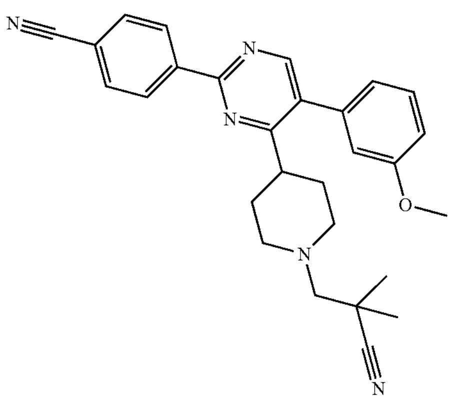 [SMILES: COc1cccc(-c2cnc(-c3ccc(C#N)cc3)nc2C2CCN(CC(C)(C)C#N)CC2)c1] | 451.24 | 452 | 3.94 WUXI2 | Intermediate J1 Final compound 57 | 207 (WRS-2A) |
| 87 | 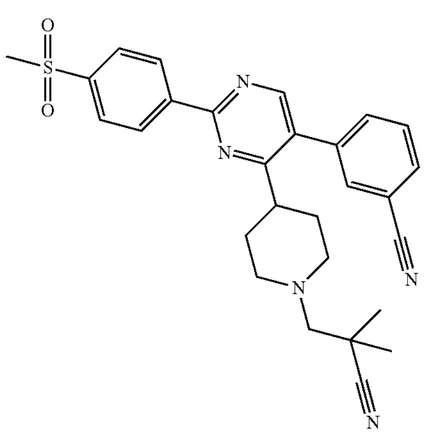 [SMILES: CC(C)(C#N)CN1CCC(c2nc(-c3ccc(S(C)(=O)=O)cc3)ncc2-c2cccc(C#N)c2)CC1] | 499.20 | 500 | 4.62 WUXI1 | Intermediate Q1 Final compound 57 | 101-122 (WRS-2A) |

-continued

| # | STRUCTURE | Exact Mass | Mass Found [M + H] | LCMS Ret Time, Method | Synthesis method | MP (° C.) |
|---|---|---|---|---|---|---|
| 88 | 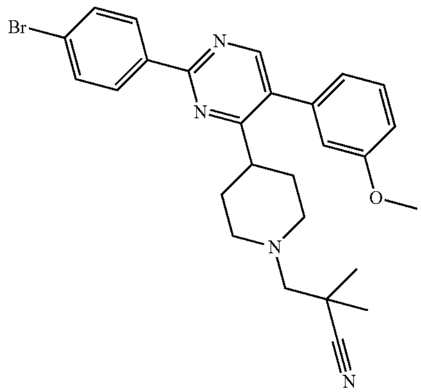 [SMILES: COc1cccc(-c2cnc(-c3ccc(Br)cc3)nc2C2CCN(CC(C)(C)C#N)CC2)c1] | 504.15 | 505 | 4.25 WUXI2 | Intermediate J1 Final compound 57 | |
| 89 | 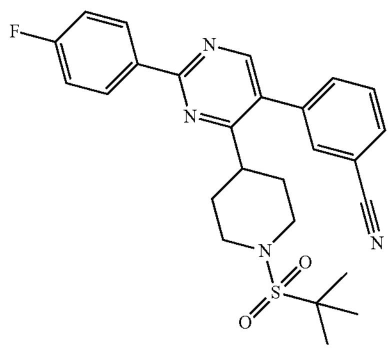 [SMILES: CC(C)(C)S(=O)(=O)N1CCC(c2nc(-c3ccc(F)cc3)ncc2-c2cccc(C#N)c2)CC1] | 478.18 | 479 | 5.1 WUXI2 | Intermediate Q1 Final compound 89 | |
| 90 | 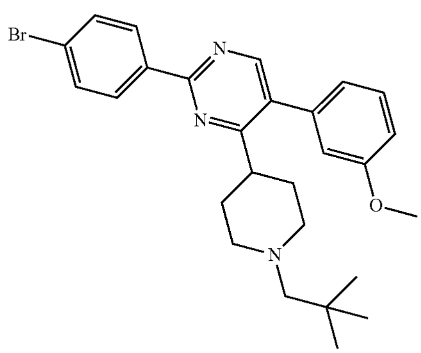 [SMILES: COc1cccc(-c2cnc(-c3ccc(Br)cc3)nc2C2CCN(CC(C)(C)C)CC2)c1] | 493.17 | 494 | 3.27 WUXI3 | Intermediate J1 Final compound 6 | |
| 91 | 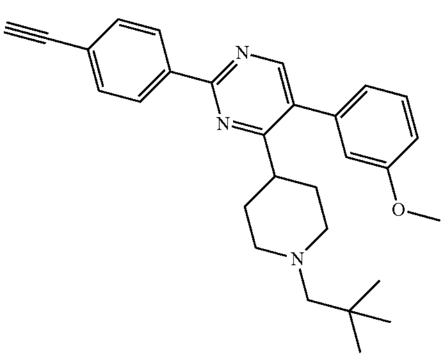 [SMILES: C#Cc1ccc(-c2ncc(-c3cccc(OC)c3)c(C3CCN(CC(C)(C)C)CC3)n2)cc1] | 439.26 | 440 | 4.41 WUXI2 | Final compound 91 | |

| # | STRUCTURE | Exact Mass | Mass Found [M + H] | LCMS Ret Time, Method | Synthesis method | MP (° C.) |
|---|---|---|---|---|---|---|
| 92 | 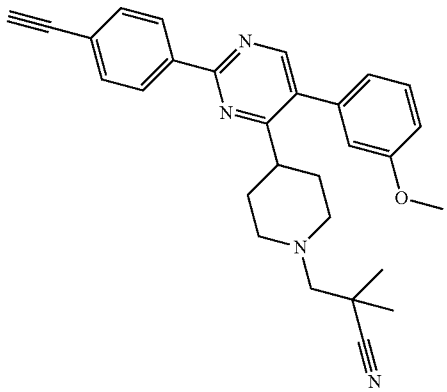 [SMILES: C#Cc1ccc(-c2ncc(-c3cccc(OC)c3)c(C3CCN(CC(C)(C)C#N)CC3)n2)cc1] | 450.24 | 451 | 4.27 WUXI2 | Final compound 91 | |
| 93 | 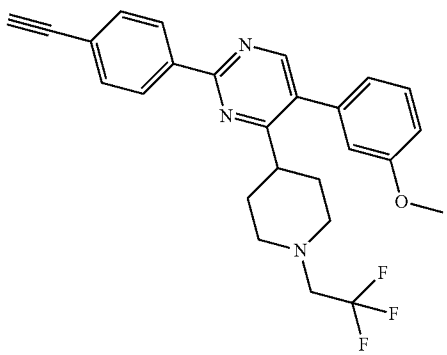 [SMILES: C#Cc1ccc(-c2ncc(-c3cccc(OC)c3)c(C3CCN(CC(F)(F)F)CC3)n2)cc1] | 451.19 | 452 | 5.18 WUXI2 | Final compound 91 | |

Analytical Methods.

All Compounds were Characterized by LC-MS. The Following LC-MS Methods were Used:

General Procedure NOVA (for Methods NOVAx)

The HPLC measurement was performed using an HPLC 1100/1200 (Agilent) system comprising a quaternary pump with degasser, an autosampler, a diode-array detector (DAD) and a column as specified in the respective methods below, the column is held at a room temperature. The MS detector (MS-Agilent simple quadripole) was configured with an electrospray-APCI ionization source. Nitrogen was used as the nebulizer gas. Data acquisition was performed with a Chemstation data system.

Method NOVA1:

In addition to the general procedure NOVA: Reversed phase HPLC was carried out on a Nucleosil C18 column (3 μm, 3×150 mm) with a flow rate of 0.42 ml/min. Two mobile phases (mobile phase A: Water TFA 0.1%; mobile phase B: 100% acetonitrile) were employed to run a gradient condition from 98% A for 3 minutes, to 100% B in 12 minutes, 100% B for 5 minutes, then back to 98% A in 2 minutes, and reequilibrated with 98% A for 6 minutes. An injection volume of 2 μl was used. The capillary voltage was 2 kV, the corona discharge was held at 1 μA and the source temperature was maintained at 250° C. A variable voltage was used for the fragmentor. Mass spectra were acquired in electrospray ionization and APCI in positive mode, by scanning from 100 to 1100 amu.

Method NOVA2:

In addition to the general procedure NOVA: Reversed phase HPLC was carried out on a Agilent Eclipse C18 column (5 μm, 4.6×150 mm) with a flow rate of 1 ml/min. Two mobile phases (mobile phase A: Water TFA 0.1%; mobile phase B: 100% acetonitrile) were employed to run a gradient condition from 98% A for 3 minutes, to 100% B in 12 minutes, 100% B for 5 minutes, then back to 98% A in 2 minutes, and reequilibrated with 98% A for 6 minutes. An injection volume of 2 μl was used. The capillary voltage was 2 kV, the corona discharge was held at 1 μA and the source temperature was maintained at 250° C. A variable voltage was used for the fragmentor. Mass spectra were acquired in electrospray ionization and APCI in positive mode, by scanning from 80 to 1000 amu.

Method NOVA3:

In addition to the general procedure NOVA: Reversed phase HPLC was carried out on a Phenomenex Gemini C18 column (3 μm, 3×30 mm) with a flow rate of 0.7 ml/min. Two mobile phases (mobile phase A: Water TFA 0.1%; mobile phase B: 100% acetonitrile) were employed to run a gradient condition from 98% A to 100% B in 2 minutes, 100% B for 0.5 minutes, then back to 98% A in 0.1 minutes, and reequilibrated with 98% A for 2.4 minutes. An injection volume of 2 μl was used. The capillary voltage was 2 kV, the corona discharge was held at 1 μA and the source temperature was maintained at 250° C. A variable voltage was used for the fragmentor. Mass spectra were acquired in electrospray ionization and APCI in positive mode, by scanning from 80 to 1000 amu.

General Procedure B (for Methods Bxxxx)

The HPLC measurement was performed using an HPLC Alliance 2695 (Waters) system comprising a quaternary pump with degasser, an autosampler, a diode-array detector (DAD), a CLND detector (Antek) and a column as specified in the respective methods below, the column is held at 40° C. The MS detector (ZQ-Waters simple quadripole) was configured with an electrospray ionization source. Nitrogen was used as the nebulizer gas. Data acquisition was performed with a Masslynx-Openlynx data system.

Method B5301:

In addition to the general procedure B: Reversed phase HPLC was carried out on a X-terra MS C18 column (3.5 µm, 4.6×100 mm) with a flow rate of 1.5 ml/min. Two mobile phases (mobile phase A: Water with 0.1% formic acid: 95/Methanol: 5%; mobile phase B: 100% Methanol) were employed to run a gradient condition from 100% A to 5% A/95% B in 12 minutes, and back to 100% A in 1 minutes. An injection volume of 10 µl was used. The cone voltage was 30V for both positive and negative ionization. Mass spectra were acquired in electrospray ionization and APCI in positive mode, by scanning from 100 to 1500 amu.

Method B5501:

In addition to the general procedure B: Reversed phase HPLC was carried out on a BEH C18 column (1.7 µm, 2.1×50 mm) with a flow rate of 0.7 ml/min. Two mobile phases (mobile phase A: Methanol, B: Ammonium acetate 10 mM in water: 90%/Acetonitrile: 10%) were employed to run a gradient condition from 5% A/95% B to 95% A/5% B in 1.3 minutes held for 0.2 minutes, and back to 5% A/95% B in 0.2 minutes, held for 0.3 minutes. An injection volume of 0.75 ml was used. The cone voltage was 30V for both positive and negative ionization. Mass spectra were acquired in electrospray ionization, by scanning from 160 to 1000 amu.

General Procedure VDR2 (for Methods V300xV30xx)

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

Method V3007V3001

In addition to the general procedure VDR2: Reversed phase UPLC was carried out on a Waters Acquity BEH (bridged ethylsiloxane/silica hybrid) C18 column (1.7 µm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 ml was used. Cone voltage was 20 V for positive and negative ionization mode. Mass spectra were acquired by scanning from 100 to 1000 in 0.2 seconds using an interscan delay of 0.1 seconds.

General Procedure Wuxi (for Methods WUXIx)

The HPLC measurement was performed using an HPLC 1100/1200 (Agilent) system comprising a quaternary pump with degasser, an autosampler, a diode-array detector (DAD) and a column as specified in the respective methods below, the column is held at 50° C. The MS detector (Agilent G1946C or 6110) was configured with an Electrospray or an APCI ionization source. Nitrogen was used as the nebulizer gas. Data acquisition was performed with a Agilent Chemstation data system.

Method WUXI1:

In addition to the general procedure WUXI: Reversed phase HPLC was carried out on a YMC-PACK ODS-AQ C18 column (5 µm, 2×50 mm) with a flow rate of 0.8 ml/min. Two mobile phases (mobile phase A: Water with 0.1% trifluoro-acetic acid; mobile phase B: acetonitrile with 0.05% trifluoro-acetic acid) were employed to run a gradient condition starting from 100% A held for 1 minutes, to 40% A/60% B in 4 minutes, held for 2.5 min, then back to 100% A in 0.5 minutes. An injection volume of 2 µl was used. The capillary voltage was 2.5 kV for positive ionization mode and 3 kV for negative ionization mode, the corona discharge was held at 4 µA if APCI and the source temperature was maintained at 200° C. Fragmentation voltage was 70V. Mass spectra were acquired in electrospray ionization or APCI in positive mode, by scanning from 100 to 1000 amu.

Method WUXI2:

In addition to the general procedure WUXI: Reversed phase HPLC was carried out on a YMC-PACK ODS-AQ C18 column (5 µm, 2×50 mm) with a flow rate of 0.8 ml/min. Two mobile phases (mobile phase A: Water with 0.1% trifluoro-acetic acid; mobile phase B: acetonitrile with 0.05% trifluoro-acetic acid) were employed to run a gradient condition starting from 90% A/10% B held for 0.8 minutes, to 20% A/80% B in 3.7 minutes, held for 3 min, then back to initial conditions in 0.5 minutes. The capillary voltage was 2.5 kV for positive ionization mode and 3 kV for negative ionization mode, the corona discharge was held at 4 µA if APCI and the source temperature was maintained at 200° C. Fragmentation voltage was 70V. Mass spectra were acquired in electrospray ionization or APCI in positive mode, by scanning from 100 to 1000 amu.

Method WUXI3:

In addition to the general procedure WUXI: Reversed phase HPLC was carried out on a YMC-PACK ODS-AQ C18 column (5 µm, 2×50 mm) with a flow rate of 0.8 ml/min. Two mobile phases (mobile phase A: Water with 0.1% trifluoro-acetic acid; mobile phase B: acetonitrile with 0.05% trifluoro-acetic acid) were employed to run a gradient condition starting from 70% A/30% B held for 0.8 minutes, to 10% A/90% B in 3.2 minutes, held for 3.5 min, then back to initial conditions in 0.5 minutes. The capillary voltage was 2.5 kV for positive ionization mode and 3 kV for negative ionization mode, the corona discharge was held at 4 µA if APCI and the source temperature was maintained at 200° C. Fragmentation voltage was 70V. Mass spectra were acquired in electrospray ionization or APCI in positive mode, by scanning from 100 to 1000 amu.

Method WUXI4:

In addition to the general procedure WUXI: Reversed phase HPLC was carried out on a Agilent TC-C18 column (5 µm, 2.1×50 mm) with a flow rate of 0.8 ml/min. Two mobile phases (mobile phase A: Water with 0.1% trifluoro-acetic acid; mobile phase B: acetonitrile with 0.05% trifluoro-acetic acid) were employed to run a gradient condition starting from 90% A/10% B held for 0.8 minutes, to 20% A/80% B in 3.7 minutes, held for 3 min, then back to initial conditions in 2 minutes. The capillary voltage was 2.5 kV for positive ionization mode and 3 kV for negative ionization mode, the corona discharge was held at 4 µA if APCI and the source temperature was maintained at 200° C. Fragmentation voltage was 70V. Mass spectra were acquired in electrospray ionization or APCI in positive mode, by scanning from 100 to 1000 amu.

General Procedure Mercachem (for Methods MERCx)

The HPLC measurement was performed using an HPLC 1100-SL or 1200-SL (Agilent) system comprising a quaternary pump with degasser, an autosampler, a diode-array detector (DAD) and a column as specified in the respective methods below. The MS detector (Agilent MSD-SL) was configured with an Electrospray ionization source. Data acquisition was performed with a Agilent Chemstation data system.

Method MERC20:

In addition to the general procedure MERC: Reversed phase HPLC was carried out on a Waters X-Bridge C18 column (3.5 μm, 2.1×50 mm) held at 25° C. with a flow rate of 0.8 ml/min. Two mobile phases (mobile phase A: Acetonitrile with 10 mM ammonia; mobile phase B: Water with 10 mM ammonia) were employed to run a gradient condition starting from 2% A to 98% A/2% B in 3.5 minutes, held for 2.5 min. Mass spectra were acquired in electrospray ionization in positive & negative mode, by scanning from 220 to 800 amu.

Method MERC22:

In addition to the general procedure MERC: Reversed phase HPLC was carried out on a Waters X-Bridge C18 column (3.5 μm, 2.1×50 mm) held at 25° C. with a flow rate of 0.8 ml/min. Two mobile phases (mobile phase A: 95% Methanol/5% 10 mM ammonium bicarbonate in Water; mobile phase B: 10 mM ammonium bicarbonate in Water) were employed to run a gradient condition starting from 10% A to 98% A/2% B in 2.5 minutes, held for 3.5 min. Mass spectra were acquired in electrospray ionization in positive & negative mode, by scanning from 220 to 800 amu.

Method MERC25:

In addition to the general procedure MERC: Reversed phase HPLC was carried out on a Gemini C18 column (3 μm, 2.1×50 mm) held at 25° C. with a flow rate of 0.8 ml/min. Two mobile phases (mobile phase A: 95% Acetonitrile/5% 10 mM ammonium bicarbonate in Water; mobile phase B: 10 mM ammonium bicarbonate in Water) were employed to run a gradient condition starting from 2% A to 98% A/2% B in 3.5 minutes, held for 2.5 min. Mass spectra were acquired in electrospray ionization in positive & negative mode, by scanning from 100 to 800 amu.

Method MERC26:

In addition to the general procedure MERC: Reversed phase HPLC was carried out on a Waters X-Bridge C18 column (3.5 μm, 2.1×50 mm) held at 25° C. with a flow rate of 0.8 ml/min. Two mobile phases (mobile phase A: 0.1% formic acid in Acetonitrile; mobile phase B: 0.1% formic acid in Water) were employed to run a gradient condition starting from 2% A to 98% A/2% B in 3.5 minutes, held for 2.5 min. Mass spectra were acquired in electrospray ionization in positive & negative mode, by scanning from 100 to 800 amu.

Method MERC27:

In addition to the general procedure MERC: Reversed phase HPLC was carried out on a Waters X-Bridge C18 column (3.5 μm, 2.1×50 mm) held at 25° C. with a flow rate of 0.8 ml/min. Two mobile phases (mobile phase A: 95% Acetonitrile/5% 10 mM ammonium bicarbonate in Water; mobile phase B: 10 mM ammonium bicarbonate in Water) were employed to run a gradient condition starting from 2% A to 98% A/2% B in 3.5 minutes, held for 4.5 min. Mass spectra were acquired in electrospray ionization in positive & negative mode, by scanning from 100 to 800 amu.

Method MERC28:

In addition to the general procedure MERC: Reversed phase HPLC was carried out on a Waters X-Bridge C18 column (3.5 μm, 2.1×50 mm) held at 25° C. with a flow rate of 0.8 ml/min. Two mobile phases (mobile phase A: 95% Acetonitrile/5% 10 mM ammonium bicarbonate in Water; mobile phase B: 10 mM ammonium bicarbonate in Water) were employed to run a gradient condition starting from 2% A to 98% A/2% B in 3.5 minutes, held for 2.5 min. Mass spectra were acquired in electrospray ionization in positive & negative mode, by scanning from 100 to 800 amu.

Method MERC30:

In addition to the general procedure MERC: Reversed phase HPLC was carried out on a Gemini C18 column (3 μm, 2.1×50 mm) held at 25° C. with a flow rate of 0.8 ml/min. Two mobile phases (mobile phase A: 95% Acetonitrile/5% 10 mM ammonium bicarbonate in Water; mobile phase B: 10 mM ammonium bicarbonate in Water) were employed to run a gradient condition starting from 2% A to 98% A/2% B in 3.5 minutes, held for 4.5 min. Mass spectra were acquired in electrospray ionization in positive & negative mode, by scanning from 100 to 800 amu.

$H^1$ NMR Analysis of Final Compounds:

Compound 6

$^1$H NMR (500 MHz, DMSO-$d_6$) d 8.81 (d, J=5.67 Hz, 2H), 8.77 (s, 1H), 8.31 (d, J=5.67 Hz, 2H), 7.46 (t, J=7.88 Hz, 1H), 7.07 (d, J=7.88 Hz, 1H), 6.98-7.04 (m, 2H), 3.81 (s, 3H), 2.79-2.89 (m, 3H), 1.96-2.15 (m, 6H), 1.66 (d, J=11.98 Hz, 2H), 0.86 (s, 9H)

Compound 55

$^1$H NMR (500 MHz, DMSO-$d_6$) δ 8.74-8.85 (m, 3H), 8.33 (d, J=4.73 Hz, 2H), 7.46 (t, J=7.88 Hz, 1H), 6.97-7.11 (m, 3H), 3.82 (s, 3H), 3.16 (q, J=9.98 Hz, 2H), 2.99 (d, J=11.03 Hz, 2H), 2.90 (t, J=11.03 Hz, 1H), 2.27 (t, J=11.66 Hz, 2H), 2.02 (q, J=11.66 Hz, 2H), 1.72 (d, J=11.66 Hz, 2H)

Compound 58

$^1$H NMR (400 MHz, CHLOROFORM-d) δ 8.86 (d, J=5.31 Hz, 2H), 8.67 (s, 1H), 8.44 (d, J=5.31 Hz, 2H), 7.86 (d, J=7.83 Hz, 1H), 7.67-7.76 (m, 2H), 7.64 (d, J=7.83 Hz, 1H), 3.02-3.17 (m, 4H), 2.80 (s, 1H), 2.37-2.47 (m, 2H), 2.22-2.37 (m, 2H), 1.75 (d, J=13.39 Hz, 2H)

Compound 70

$^1$H NMR (400 MHz, CHLOROFORM-d) δ 8.85 (d, J=6.06 Hz, 2H), 8.69 (s, 1H), 8.41-8.46 (m, 2H), 7.48 (t, J=8.08 Hz, 1H), 7.07 (dd, J=2.02, 8.08 Hz, 1H), 6.96 (d, J=7.33 Hz, 1H), 6.90 (s, 1H), 3.93 (s, 3H), 3.03-3.14 (m, 2H), 2.90-3.01 (m, 1H), 2.73 (t, J=13.64 Hz, 2H), 2.18-2.32 (m, 4H), 1.74 (s, 2H), 1.62 (br. s., 3H)

Compound 67

$^1$H NMR (400 MHz, CHLOROFORM-d) δ 9.31 (d, J=2.27 Hz, 1H), 8.60 (dd, J=2.27, 8.59 Hz, 1H), 8.43 (s, 1H), 7.69 (d, J=7.58 Hz, 1H), 7.53-7.60 (m, 2H), 7.45-7.52 (m, 1H), 6.80 (d, J=8.59 Hz, 1H), 3.97 (s, 3H), 2.80 (d, J=6.82 Hz, 2H), 2.57 (br. s., 1H), 2.01-2.16 (m, 4H), 1.96 (s, 2H), 1.49-1.58 (m, 2H), 0.81 (s, 9H)

Compound 57

$^1$H NMR (400 MHz, DMSO-$d_6$) δ 8.76-8.85 (m, 3H), 8.29-8.37 (m, 2H), 7.42-7.52 (m, 1H), 6.97-7.12 (m, 3H), 3.83 (s, 3H), 3.02 (d, J=11.12 Hz, 2H), 2.89 (t, J=11.10 Hz, 1H), 2.44 (s, 2H), 2.14-2.27 (m, 2H), 1.94-2.12 (m, 2H), 1.72 (d, J=12.63 Hz, 2H), 1.29 (s, 6H)

Compound 66

$^1$H NMR (400 MHz, CHLOROFORM-d) δ 8.62 (dd, J=5.81, 8.84 Hz, 2H), 8.57 (s, 1H), 7.82 (d, J=7.58 Hz, 1H), 7.66-7.73 (m, 2H), 7.61 (s, 1H), 7.25 (t, J=8.84 Hz, 2H), 2.94 (d, J=7.58 Hz, 2H), 2.60-2.78 (m, 1H), 2.13-2.31 (m, 4H), 2.09 (s, 2H), 1.64 (d, J=8.34 Hz, 2H), 0.95 (s, 9H)

Compound 65

¹H NMR (400 MHz, CHLOROFORM-d) δ 8.73 (d, J=8.34 Hz, 2H), 8.63 (s, 1H), 7.80-7.90 (m, 3H), 7.66-7.74 (m, 2H), 7.60-7.65 (m, 1H), 2.94 (d, J=6.57 Hz, 2H), 2.65-2.79 (m, 1H), 2.14-2.30 (m, 4H), 2.09 (s, 2H), 1.65 (d, J=4.80 Hz, 2H), 0.95 (s, 9H)

Compound 71

¹H NMR (400 MHz, CHLOROFORM-d) δ 8.49-8.61 (m, 3H), 7.41 (t, J=8.03 Hz, 1H), 7.17 (t, J=8.03 Hz, 2H), 7.00 (dd, J=2.01, 8.03 Hz, 1H), 6.90 (d, J=8.03 Hz, 1H), 6.81-6.86 (m, 1H), 3.87 (s, 3H), 2.84-3.11 (m, 5H), 2.16-2.42 (m, 4H), 1.70 (d, J=13.05 Hz, 2H)

Compound 39

¹H NMR (400 MHz, DMSO-d₆) δ 8.73-8.90 (m, 3H), 8.32 (d, J=6.06 Hz, 2H), 7.53-7.68 (m, 3H), 7.40-7.50 (m, 1H), 2.84 (d, J=11.12 Hz, 2H), 2.68-2.79 (m, 1H), 1.92-2.17 (m, 6H), 1.66 (d, J=12.13 Hz, 2H), 0.86 (s, 9H)

Compound 21

¹H NMR (400 MHz, DMSO-d₆) δ 8.69-8.79 (m, 2H), 8.36 (s, 1H), 8.19-8.28 (m, 2H), 7.34-7.48 (m, 1H), 7.04-7.15 (m, 2H), 6.97 (dd, J=1.77, 8.34 Hz, 1H), 3.81 (s, 3H), 3.36-3.40 (m, 3H), 2.46 (t, J=4.55 Hz, 3H), 2.04 (s, 2H), 1.23 (br. s., 2H), 0.83 (s, 9H)

Compound 40

¹H NMR (400 MHz, DMSO-d₆) δ 8.75-8.96 (m, 3H), 8.33 (d, J=6.06 Hz, 2H), 7.89 (br. s., 2H), 7.72-7.85 (m, 2H), 2.84 (d, J=9.35 Hz, 2H), 2.63-2.77 (m, 1H), 1.93-2.17 (m, 6H), 1.56-1.78 (m, 2H), 0.85 (s, 9H)

The following six compounds/examples were also prepared in accordance with the procedures described herein:

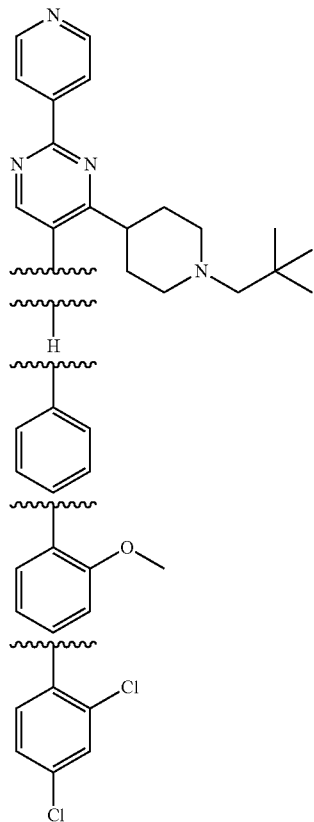

-continued

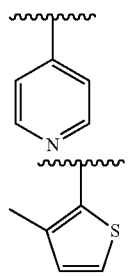

BIOLOGICAL EXAMPLES

In Vitro Method for Testing Compounds for Antibacterial Activity Against Various Bacterial Strains Preparation of Bacterial Suspensions for Susceptibility Testing The following bacteria were used: *Staphylococcus aureus* ATCC 29213, methicillin-resistant *Staphylococcus aureus* (MRSA) ATCC 700788 and *Escherichia coli* ATCC 35218. The bacteria used in this study were grown overnight in flasks containing 100 ml Mueller-Hinton broth (Difco cat. nr. 0757-17) in sterile de-ionized water, with shaking, at 37° C. Stocks were store at −70° C. until use.

Bacteria were incubated on a tryptic soy agar plate containing 5% sheep blood (Becton Dickinson cat. nr. 254053) for 18-24 hours at 35° C. in aerobic conditions (first passage). For the second passage, fresh Mueller-Hinton broth is inoculated with 5-10 colonies and grown overnight at 35° C. until turbidity (reaching log-phase) in aerobic conditions is reached. The bacterial suspension is then adjusted to 0.5 McFarland density and further diluted 1:100 in Mueller Hinton broth medium. This is used as inoculum.

Antibacterial Susceptibility Testing: IC90 Determination

MIC assays were performed by the broth microdilution method in a 96-well format (flat-bottom microtitre plates) with a final volume of 0.1 ml Mueller Hinton broth containing two-fold serial dilutions of compounds and inoculated with 5×10⁵ CFU/ml of bacteria (standard inoculum size according to CLSI guidelines). Inhibitors are typically varied over the range of 63 to 0.49 µM. The final DMSO concentration in the assay was 1.25% (maximum tolerable DMSO concentration=6%). In the assays where the effect of human serum on the activity of the compounds against *S. aureus* was tested, human serum was added at a final concentration of 10%. The plates were incubated at 35° C. for 16-20 hours. At the end of incubation the bacterial growth was quantified fluorometrically. For this, resazurin was added to all wells and the plates were re-incubated. The incubation time is dependent on the type of bacteria. A change in color from blue to pink indicated the growth of bacteria. The fluorescence was read in computer-controlled fluorometer (Fluoroskan Ascent FL, Labsystems) at an excitation wavelength 540 nm and an emission wavelength of 590 nm. The % growth inhibition achieved by the compounds was calculated according to standard methods. The IC90 (expressed in µg/ml) was defined as the 90% inhibitory concentration for bacterial growth. A panel of reference compounds were simultaneously tested for QC approval.

Cytotoxicity Assays

Cytotoxicity of the compounds was evaluated using the MTT assay. Human HelaM cells grown in 96-well plates were exposed to serial dilutions of the tested compounds (final volume of 0.2 ml) and incubated for 72 hours at 37° C. and 5% CO2 Inhibitors are typically varied over the range of 25 to 0.8 µM. The final DMSO concentration in the assay is 0.5%. MTT (3-(4,5-Dimethylthiazol-2-yl)-2,5-diphenyltetrazolium bromide, a tetrazole) was added and reduced to purple formazan only in living cells. Solubilization of the formazan crystals was achieved by adding 100 µl 2-propanol. Cell viability was determined by measuring the absorbance of the reduced formazan, giving a purple color, at 540 nm and 690 nm. The absorbance measured at 690 nm was automatically subtracted from the absorbance at 540 nm, to eliminate the effects of non-specific absorption. The percent cytotoxicity achieved by the compounds was calculated according to standard methods. Cytotoxicity is reported as CC50, the concentration that causes a 50% reduction in cell viability.

Protocol for MIC Determination of Compounds on ECO/PAE/STA in Microplates

Add 4-5 colonies of an overnight grown plate to 5 ml Mueller Hinton medium

Incubate for 3-6 hours at 37° C. in shaker incubator (300 rpm)

Measure OD at 600 nm (OD600=1->109 CFU/ml)

Dilute bacteria until 105 CFU/ml in medium

Prepare 2-fold dilutions in microplates in 100 µl Mueller Hinton medium (final conc. from 64 to 0.125 µg/ml)

Add 100 µl of bacteria dilution to each well

Incubate for 18-20 hours at 37° C.

Check the growth against the control visually

MIC is the lowest concentration with no growth (90% inhibition of growth)

Biological Results

Compound of the examples/invention are/were tested in the antibacterial susceptibility and/or the cyctotoxicity assays described above. Compounds of the examples/invention are/were found to exhibit an IC90 value of less than 50 µg/mL (e.g. less than 15 µg/mL), a CC50 value of less than 50 µg/mL (e.g. less than 15 µg/mL) and/or a MIC90 of less than 10 µg/mL (e.g. less than 1 µg/mL), in the respective assays. Certain compounds exhibited an IC90 value of less than 10 µg/mL (e.g. less than 1 µg/mL), or a CC50 value of less than 10 µg/mL (e.g. less than 5 µg/mL) and/or a MIC90 value of less than 0.5 µg/mL, in the respective assays.

Certain compounds may be available from commercially-available sources, e.g. CHEMBRIDGE.

TABLE 1

Compounds of formula (I).

| # | STRUCTURE | IC90 (µg/ml) | CC50 (µg/ml) |
|---|-----------|--------------|--------------|
| 1 | 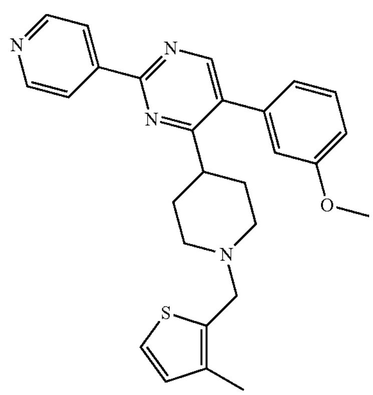 [SMILES: COc1cccc(-c2cnc(-c3ccncc3)nc2C2CCN(Cc3sccc3C)CC2)c1]          |              | 8.5          |
| 2 | 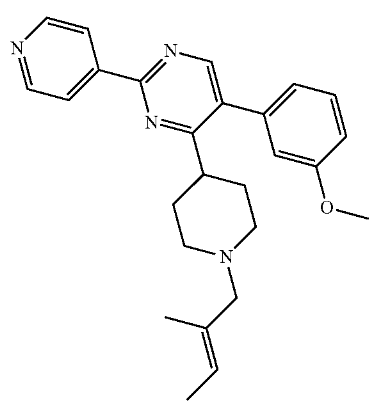 [SMILES: C/C=C(\C)CN1CCC(c2nc(-c3ccncc3)ncc2-c2cccc(OC)c2)CC1]          |              | 13.73        |

TABLE 1-continued

Compounds of formula (I).

| # | STRUCTURE | IC90 (μg/ml) | CC50 (μg/ml) |
|---|---|---|---|
| 3 | 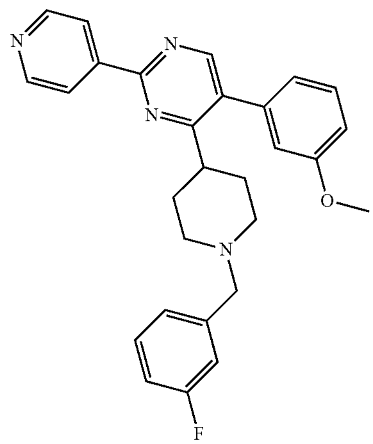 [SMILES: COc1cccc(-c2cnc(-c3ccncc3)nc2C2CCN(Cc3cccc(F)c3)CC2)c1] | 5.59 | >4.5 |
| 4 | 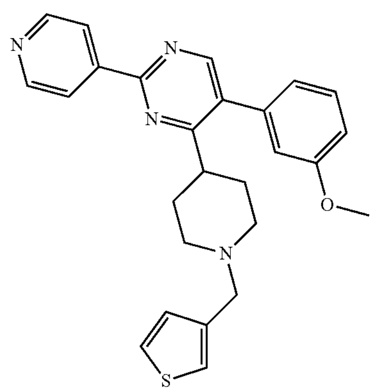 [SMILES: COc1cccc(-c2cnc(-c3ccncc3)nc2C2CCN(Cc3ccsc3)CC2)c1] | 12.91 | >11.1 |
| 5 | 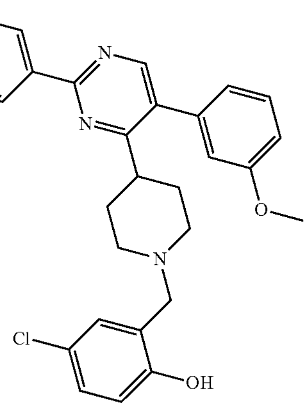 | 2.10 | 6.3 |

TABLE 1-continued

Compounds of formula (I).

| # | STRUCTURE | IC90 (µg/ml) | CC50 (µg/ml) |
|---|---|---|---|
| 6 | 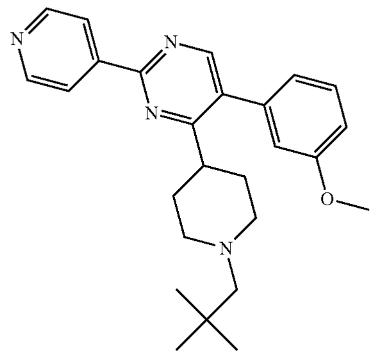 [SMILES: COc1cccc(-c2cnc(-c3ccncc3)nc2C2CCN(CC(C)(C)C)CC2)c1] | 1.05 | >10.5 |
| 7 | 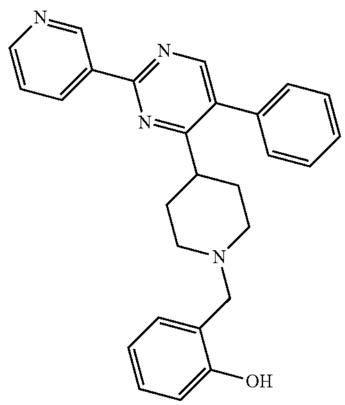 [SMILES: Oc1ccccc1CN1CCC(c2nc(-c3cccnc3)ncc2-c2ccccc2)CC1] | 14.32 | |
| 8 | 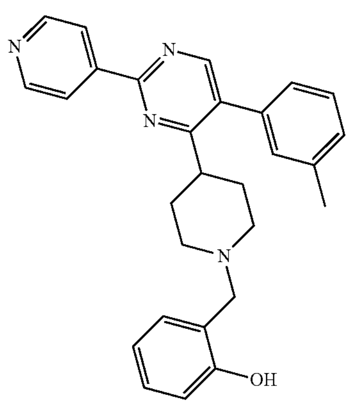 [SMILES: Cc1cccc(-c2cnc(-c3ccncc3)nc2C2CCN(Cc3ccccc3O)CC2)c1] | 5.50 | >4.4 |
| 9 | 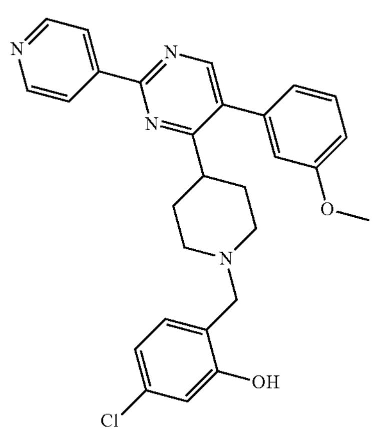 [SMILES: COc1cccc(-c2cnc(-c3ccncc3)nc2C2CCN(Cc3ccc(Cl)cc3O)CC2)c1] | 0.97 | 5.9 |

TABLE 1-continued
Compounds of formula (I).
| # | STRUCTURE | IC90 (µg/ml) | CC50 (µg/ml) |
|---|---|---|---|
| 10 | 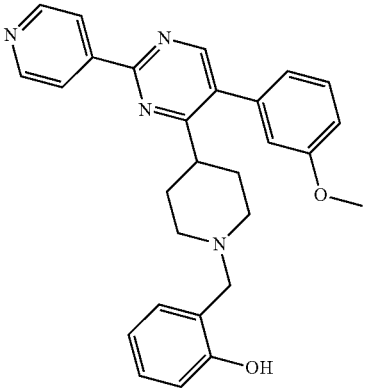 [SMILES: COc1cccc(-c2cnc(-c3ccncc3)nc2C2CCN(Cc3ccccc3O)CC2)c1] | 1.68 | 9.9 |
| 11 | 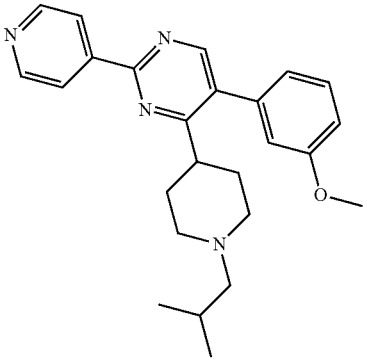 [SMILES: COc1cccc(-c2cnc(-c3ccncc3)nc2C2CCN(CC(C)C)CC2)c1] | 5.49 | >10.1 |
| 12 | 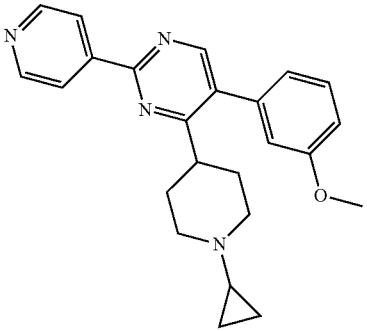 [SMILES: COc1cccc(-c2cnc(-c3ccncc3)nc2C2CCN(C3CC3)CC2)c1] | 5.78 | >9.7 |
| 13 | 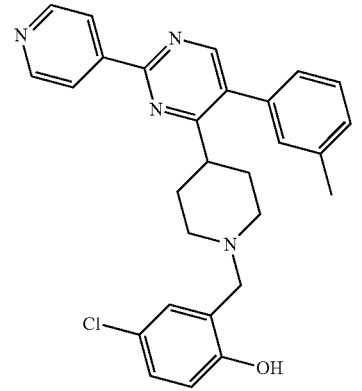 [SMILES: Cc1cccc(-c2cnc(-c3ccncc3)nc2C2CCN(Cc3cc(Cl)ccc3O)CC2)c1] | 1.71 | 5.2 |

TABLE 1-continued

Compounds of formula (I).

| # | STRUCTURE | IC90 (µg/ml) | CC50 (µg/ml) |
|---|---|---|---|
| 14 | 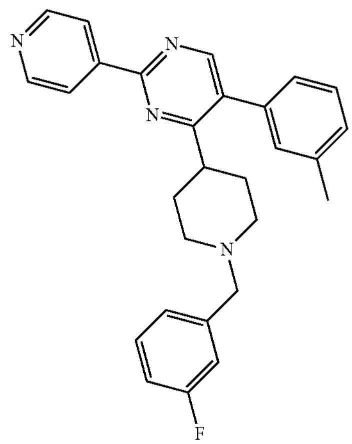 [SMILES: Cc1cccc(-c2cnc(-c3ccncc3)nc2C2CCN(Cc3cccc(F)c3)CC2)c1] | 9.16 | >11.0 |
| 15 | 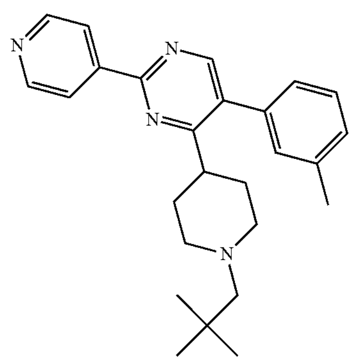 [SMILES: Cc1cccc(-c2cnc(-c3ccncc3)nc2C2CCN(CC(C)(C)C)CC2)c1] | 1.49 | >10.1 |
| 16 | 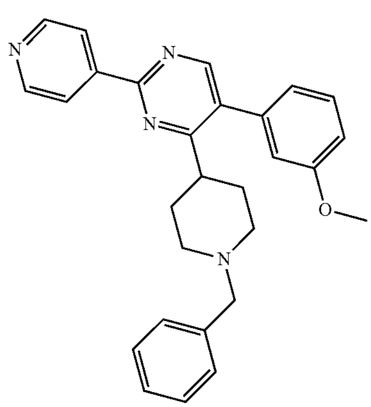 [SMILES: COc1cccc(-c2cnc(-c3ccncc3)nc2C2CCN(Cc3ccccc3)CC2)c1] | 6.92 | >11.0 |

TABLE 1-continued
Compounds of formula (I).
| # | STRUCTURE | IC90 (µg/ml) | CC50 (µg/ml) |
|---|---|---|---|
| 17 | 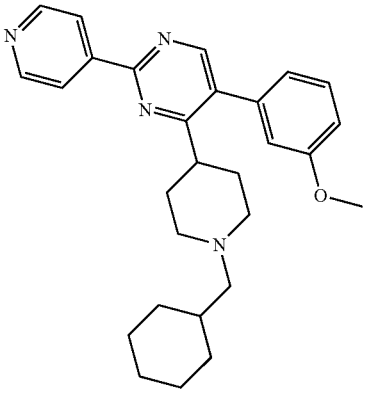 [SMILES: COc1cccc(-c2cnc(-c3ccncc3)nc2C2CCN(CC3CCCCC3)CC2)c1] | 13.37 | >11.1 |
| 18 | 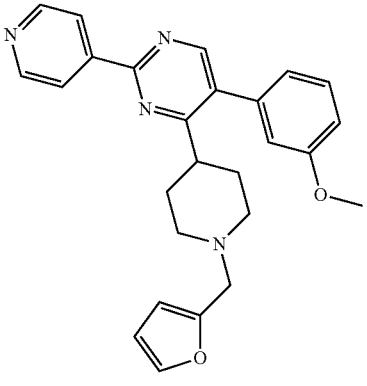 | 13.03 | >10.7 |
| 19 | 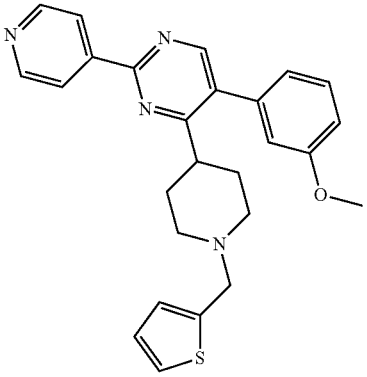 | 5.57 | >11.1 |

TABLE 1-continued
Compounds of formula (I).
| # | STRUCTURE | IC90 (µg/ml) | CC50 (µg/ml) |
|---|---|---|---|
| 20 | 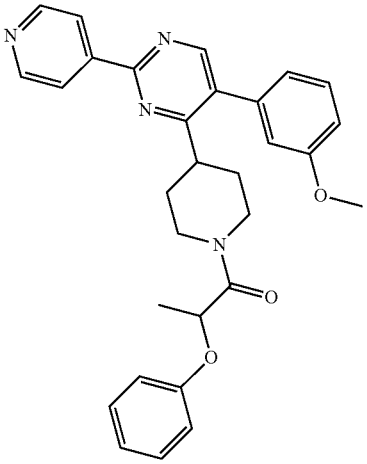 [SMILES: COc1cccc(-c2cnc(-c3ccncc3)nc2C2CCN(C(=O)C(C)Oc3ccccc3)CC2)c1] | 7.15 | 8.1 |
| 21 | 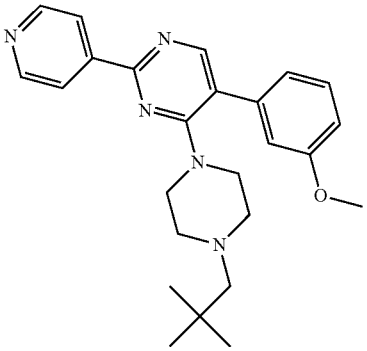 | 0.39 | 5.9 |
| 22 | 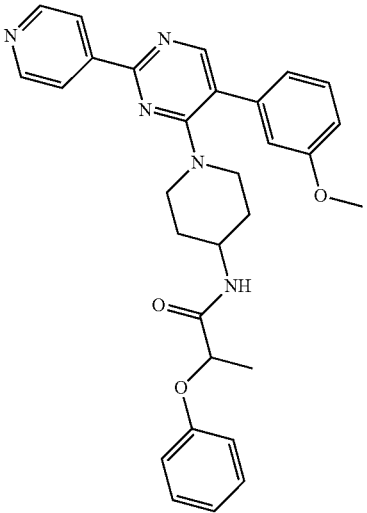 [SMILES: COc1cccc(-c2cnc(-c3ccncc3)nc2N2CCC(NC(=O)C(C)Oc3ccccc3)CC2)c1] | 5.16 | 8.5 |

TABLE 1-continued
Compounds of formula (I).
| # | STRUCTURE | IC90 (μg/ml) | CC50 (μg/ml) |
|---|-----------|--------------|--------------|
| 23 | 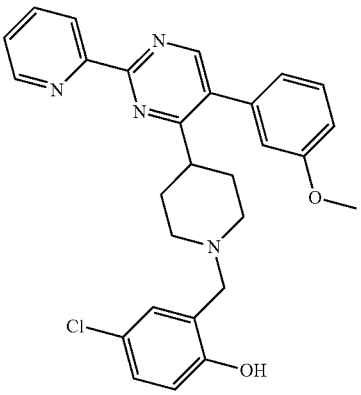 [SMILES: COc1cccc(-c2cnc(-c3ccccn3)nc2C2CCN(Cc3cc(Cl)ccc3O)CC2)c1] | 7.37 | 4.4 |
| 24 | 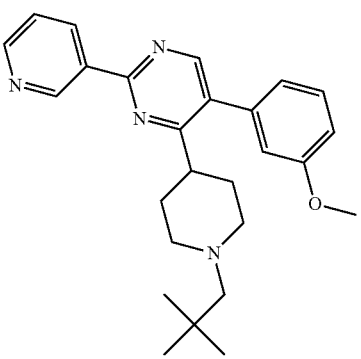 [SMILES: COc1cccc(-c2cnc(-c3cccnc3)nc2C2CCN(CC(C)(C)C)CC2)c1] | 1.68 | >11.4 |
| 25 | 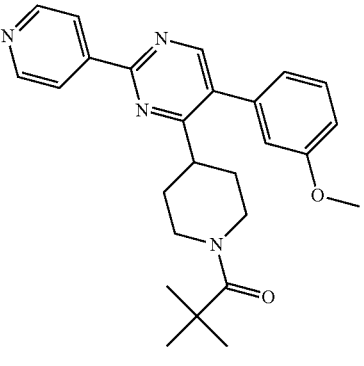 [SMILES: COc1cccc(-c2cnc(-c3ccncc3)nc2C2CCN(C(=O)C(C)(C)C)CC2)c1] | 3.27 | >10.8 |
| 26 | 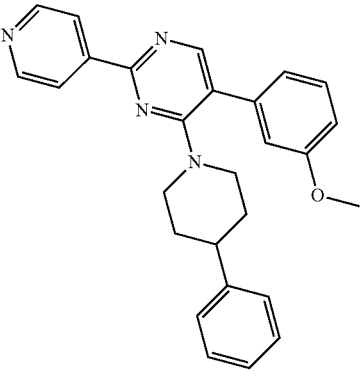 | 7.51 | 5.7 |

TABLE 1-continued

Compounds of formula (I).

| # | STRUCTURE | IC90 (μg/ml) | CC50 (μg/ml) |
|---|---|---|---|
| 27 | 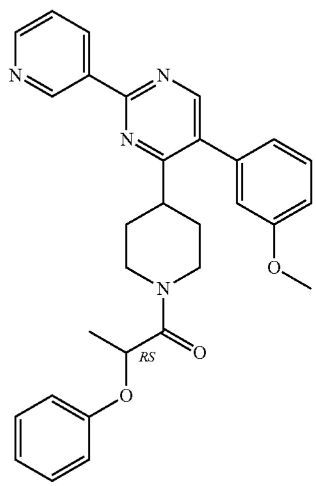 [SMILES: COc1cccc(-c2cnc(-c3cccnc3)nc2C2CCN(C(=O)C(C)Oc3ccccc3)CC2)c1] | 9.10 | 7.1 |
| 28 | 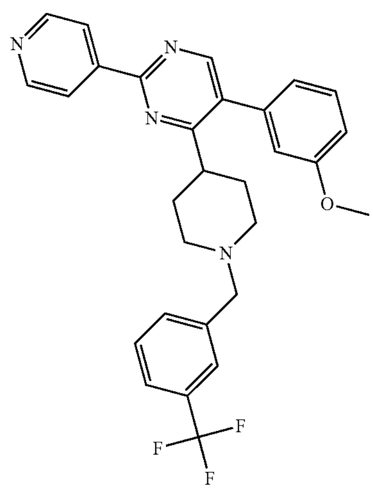 [SMILES: COc1cccc(-c2cnc(-c3ccncc3)nc2C2CCN(Cc3cccc(C(F)(F)F)c3)CC2)c1] | 5.28 | 4.7 |
| 29 | 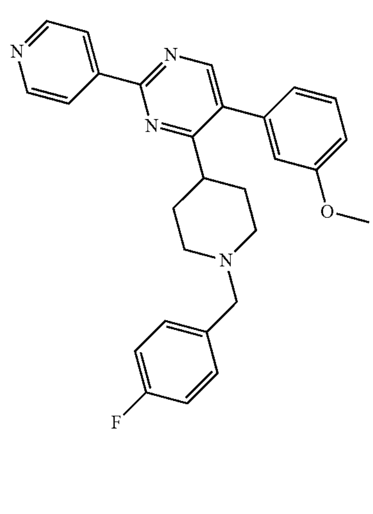 [SMILES: COc1cccc(-c2cnc(-c3ccncc3)nc2C2CCN(Cc3ccc(F)cc3)CC2)c1] | 3.45 | 8.5 |

TABLE 1-continued

Compounds of formula (I).

| # | STRUCTURE | IC90 (µg/ml) | CC50 (µg/ml) |
|---|---|---|---|
| 30 | 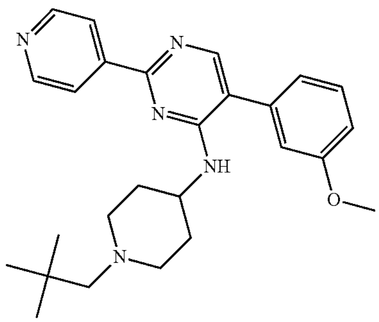 [SMILES: COc1cccc(-c2cnc(-c3ccncc3)nc2NC2CCN(CC(C)(C)C)CC2)c1] | 5.19 | 8.8 |
| 31 | 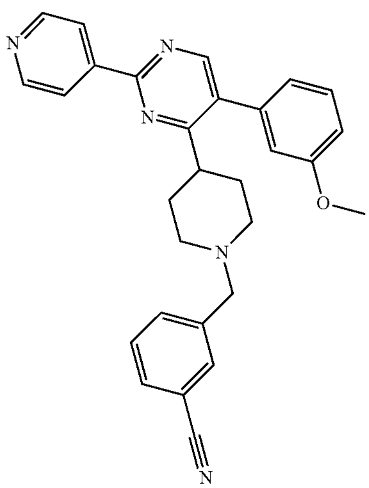 [SMILES: COc1cccc(-c2cnc(-c3ccncc3)nc2C2CCN(Cc3cccc(C#N)c3)CC2)c1] | 7.32 | 4.2 |
| 32 | 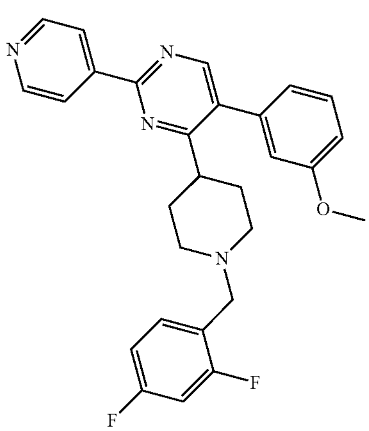 [SMILES: COc1cccc(-c2cnc(-c3ccncc3)nc2C2CCN(Cc3ccc(F)cc3F)CC2)c1] | 3.27 | 5.5 |

TABLE 1-continued

Compounds of formula (I).

| # | STRUCTURE | IC90 (µg/ml) | CC50 (µg/ml) |
|---|-----------|--------------|--------------|
| 33 | 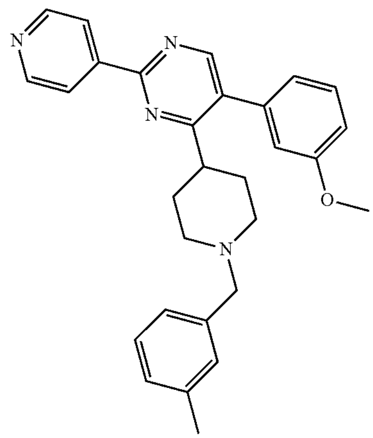 [SMILES: COc1cccc(-c2cnc(-c3ccncc3)nc2C2CCN(Cc3cccc(C)c3)CC2)c1] | 13.15 | 7.6 |
| 34 | 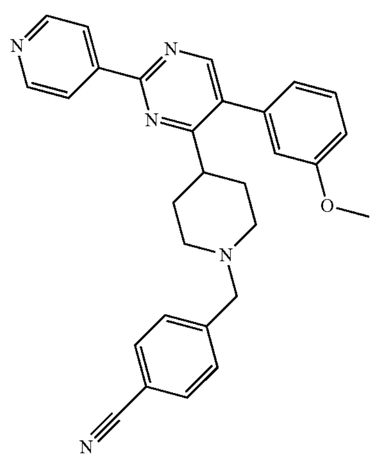 [SMILES: COc1cccc(-c2cnc(-c3ccncc3)nc2C2CCN(Cc3ccc(C#N)cc3)CC2)c1] | 6.99 | 8.7 |
| 35 | 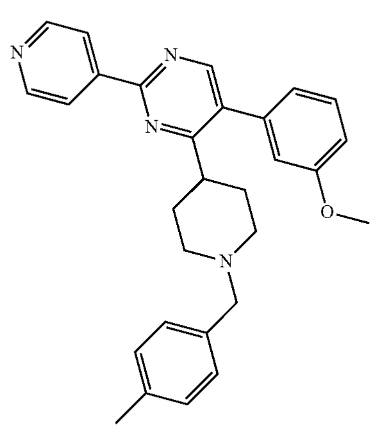 [SMILES: COc1cccc(-c2cnc(-c3ccncc3)nc2C2CCN(Cc3ccc(C)cc3)CC2)c1] | 13.3 | 7.7 |

TABLE 1-continued

Compounds of formula (I).

| # | STRUCTURE | IC90 (µg/ml) | CC50 (µg/ml) |
|---|---|---|---|
| 36 | 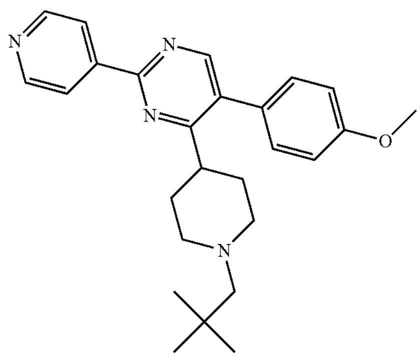 [SMILES: COc1ccc(-c2cnc(-c3ccncc3)nc2C2CCN(CC(C)(C)C)CC2)cc1] | 2.98 | >10.5 |
| 37 | 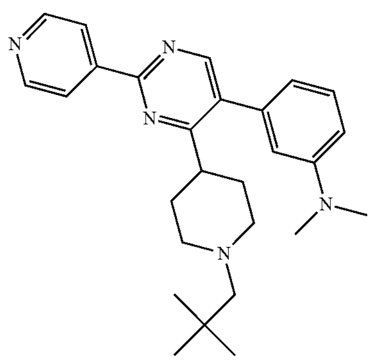 [SMILES: CN(C)c1cccc(-c2cnc(-c3ccncc3)nc2C2CCN(CC(C)(C)C)CC2)c1] | 3.04 | 9.2 |
| 38 | 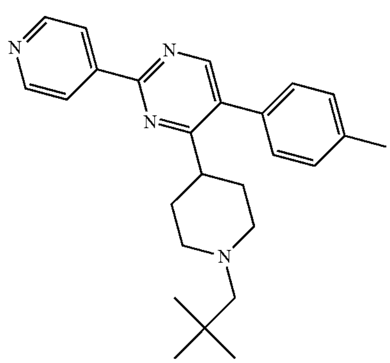 [SMILES: Cc1ccc(-c2cnc(-c3ccncc3)nc2C2CCN(CC(C)(C)C)CC2)cc1] | 5.04 | >4.0 |
| 39 | 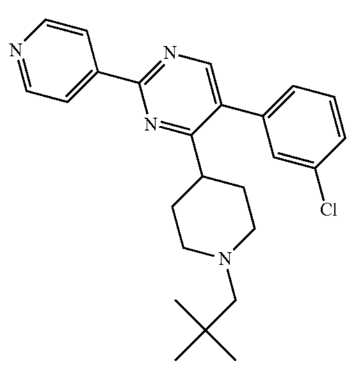 [SMILES: CC(C)(C)CN1CCC(c2nc(-c3ccncc3)ncc2-c2cccc(Cl)c2)CC1] | 0.76 | 7.3 |

TABLE 1-continued
Compounds of formula (I).
| # | STRUCTURE | IC90 (µg/ml) | CC50 (µg/ml) |
|---|---|---|---|
| 40 | 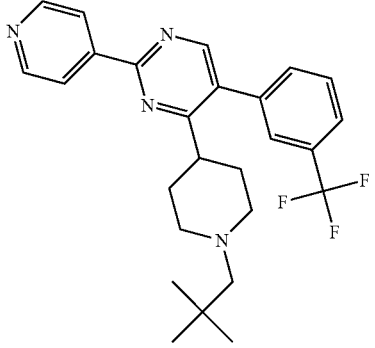 [SMILES: CC(C)(C)CN1CCC(c2nc(-c3ccncc3)ncc2-c2cccc(C(F)(F)F)c2)CC1] | 0.52 | 7.0 |
| 41 | 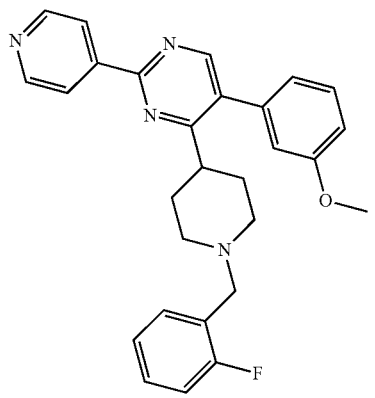 [SMILES: COc1cccc(-c2cnc(-c3ccncc3)nc2C2CCN(Cc3ccccc3F)CC2)c1] | 8.66 | 7.7 |
| 42 | 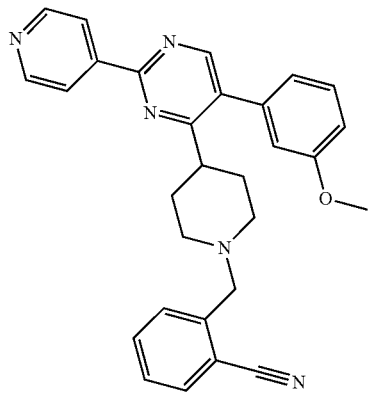 [SMILES: COc1cccc(-c2cnc(-c3ccncc3)nc2C2CCN(Cc3ccccc3C#N)CC2)c1] | 6.75 | 5.1 |

TABLE 1-continued
Compounds of formula (I).
| # | STRUCTURE | IC90 (μg/ml) | CC50 (μg/ml) |
|---|-----------|--------------|--------------|
| 43 | 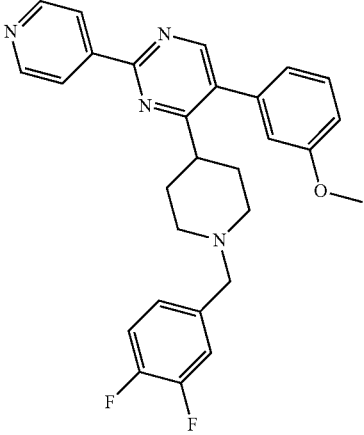 [SMILES: COc1cccc(-c2cnc(-c3ccncc3)nc2C2CCN(Cc3ccc(F)c(F)c3)CC2)c1] | 2.24 | 6.2 |
| 44 | 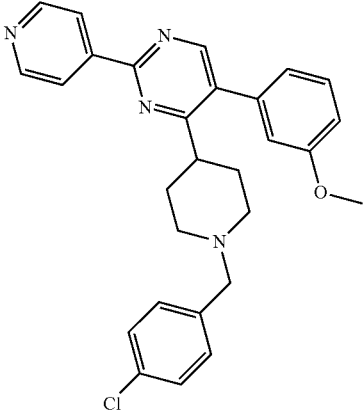 | 2.23 | 7.0 |
| 45 | 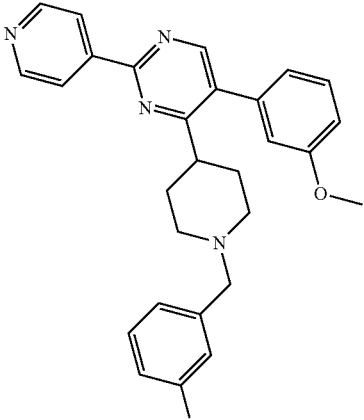 | 3.49 | 4.9 |

TABLE 1-continued
Compounds of formula (I).
| # | STRUCTURE | IC90 (μg/ml) | CC50 (μg/ml) |
|---|---|---|---|
| 46 | 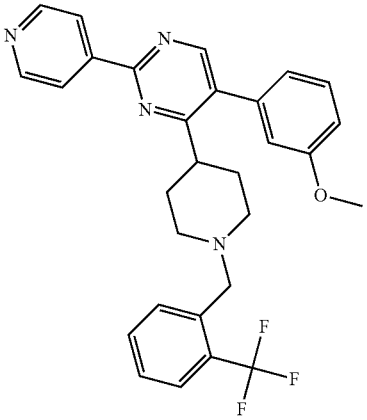 [SMILES: COc1cccc(-c2cnc(-c3ccncc3)nc2C2CCN(Cc3ccccc3C(F)(F)F)CC2)c1] | 4.10 | 4.2 |
| 47 | 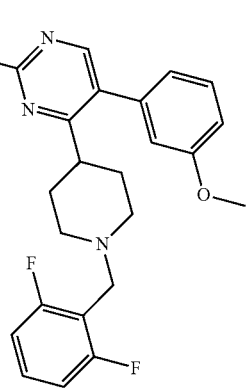 | 1.74 | 2.1 |
| 48 | 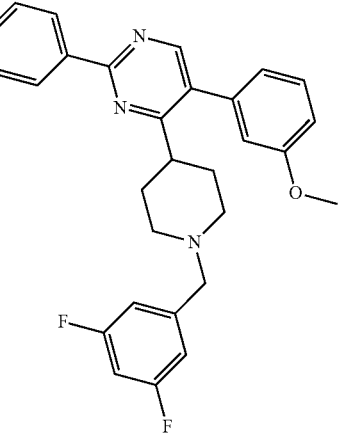 | 3.16 | 2.2 |

TABLE 1-continued

Compounds of formula (I).

| # | STRUCTURE | IC90 (µg/ml) | CC50 (µg/ml) |
|---|-----------|--------------|--------------|
| 49 | 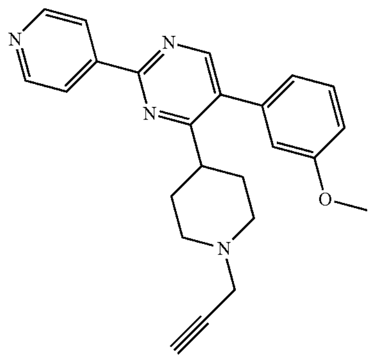 [SMILES: C#CCN1CCC(c2nc(-c3ccncc3)ncc2-c2cccc(OC)c2)CC1] | 12.16 | >9.7 |
| 50 | 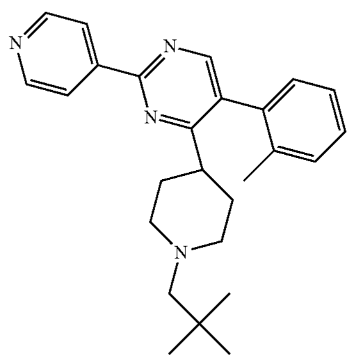 [SMILES: Cc1ccccc1-c1cnc(-c2ccncc2)nc1C1CCN(CC(C)(C)C)CC1] | 9.61 | >4.0 |
| 51 | 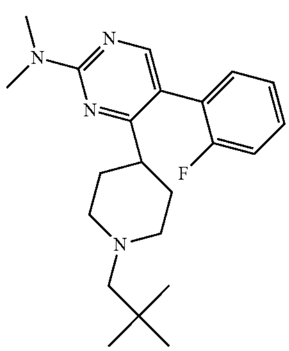 [SMILES: CN(C)c1ncc(-c2ccccc2F)c(C2CCN(CC(C)(C)C)CC2)n1] | 13.45 | 7.8 |
| 52 | 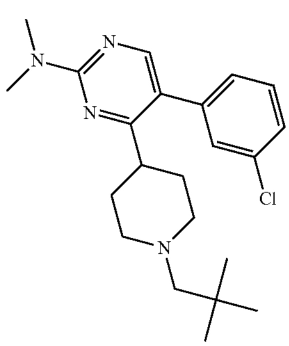 [SMILES: CN(C)c1ncc(-c2cccc(Cl)c2)c(C2CCN(CC(C)(C)C)CC2)n1] | 1.28 | 6.7 |

TABLE 1-continued

Compounds of formula (I).

| # | STRUCTURE | IC90 (µg/ml) | CC50 (µg/ml) |
|---|-----------|--------------|--------------|
| 53 | 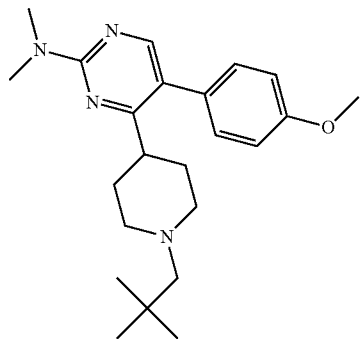 | 5.47 | 7.5 |
| 54 | 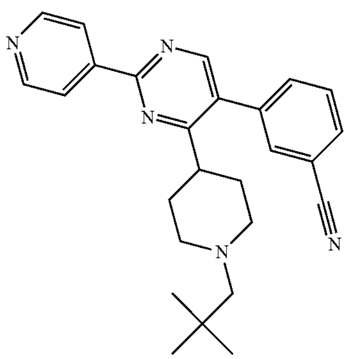 [SMILES: CC(C)(C)CN1CCC(c2nc(-c3ccncc3)ncc2-c2cccc(C#N)c2)CC1] | 1.29 | >10.3 |
| 55 | 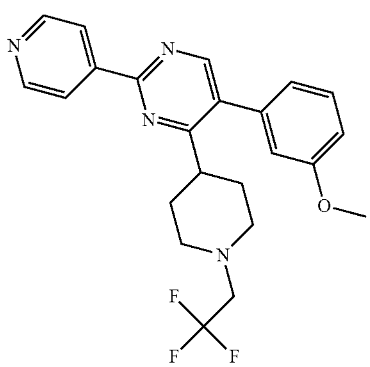 | 0.39 | 6.3 |
| 56 | 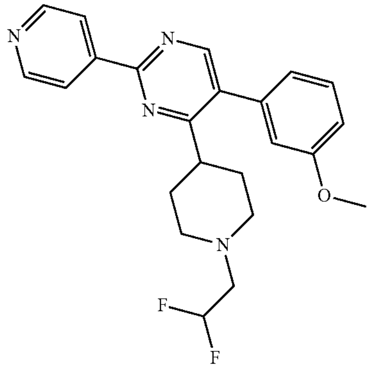 [SMILES: COc1cccc(-c2cnc(-c3ccncc3)nc2C2CCN(CC(F)F)CC2)c1] | 1.49 | >10.3 |

TABLE 1-continued
Compounds of formula (I).
| # | STRUCTURE | IC90 (µg/ml) | CC50 (µg/ml) |
|---|---|---|---|
| 57 | 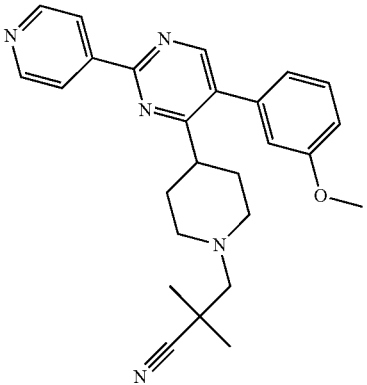 [SMILES: COc1cccc(-c2cnc(-c3ccncc3)nc2C2CCN(CC(C)(C)C#N)CC2)c1] | 0.39 | 7.3 |
| 58 | 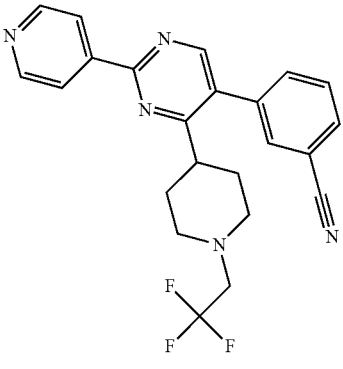 [SMILES: N#Cc1cccc(-c2cnc(-c3ccncc3)nc2C2CCN(CC(F)(F)F)CC2)c1] | 0.69 | >10.6 |
| 59 | 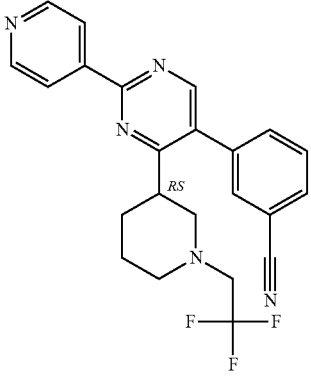 [SMILES: N#Cc1cccc(-c2cnc(-c3ccncc3)nc2C2CCCN(CC(F)(F)F)C2)c1] | >26.7 | >10.6 |
| 60 | 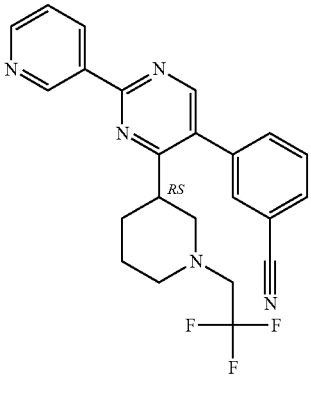 [SMILES: N#Cc1cccc(-c2cnc(-c3cccnc3)nc2C2CCCN(CC(F)(F)F)C2)c1] | >26.7 | >10.6 |

TABLE 1-continued
Compounds of formula (I).
| # | STRUCTURE | IC90 (µg/ml) | CC50 (µg/ml) |
|---|-----------|--------------|--------------|
| 61 | 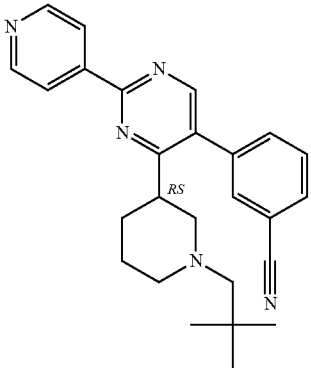 [SMILES: CC(C)(C)CN1CCCC(c2nc(-c3ccncc3)ncc2-c2cccc(C#N)c2)C1] | >25.9 | >10.3 |
| 62 | 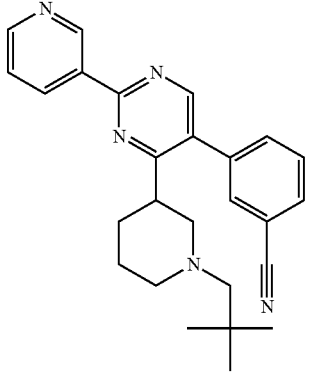 [SMILES: CC(C)(C)CN1CCCC(c2nc(-c3cccnc3)ncc2-c2cccc(C#N)c2)C1] | >25.9 | >10.3 |
| 63 | 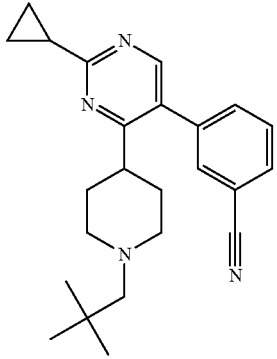 [SMILES: CC(C)(C)CN1CCC(c2nc(C3CC3)ncc2-c2cccc(C#N)c2)CC1] | 2.74 | >9.4 |
| 64 | 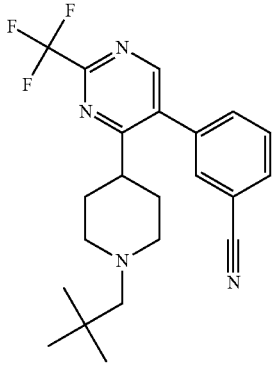 [SMILES: CC(C)(C)CN1CCC(c2nc(C(F)(F)F)ncc2-c2cccc(C#N)c2)CC1] | 1.46 | >10.1 |

TABLE 1-continued

Compounds of formula (I).

| # | STRUCTURE | IC90 (µg/ml) | CC50 (µg/ml) |
|---|---|---|---|
| 65 | 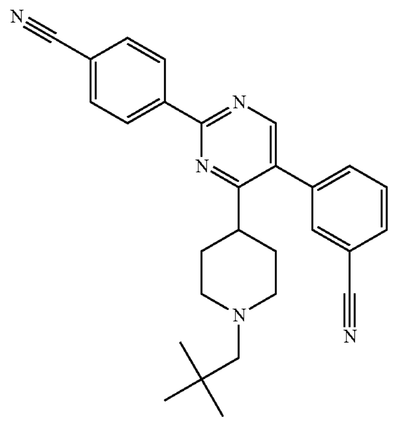 [SMILES: CC(C)(C)CN1CCC(c2nc(-c3ccc(C#N)cc3)ncc2-c2cccc(C#N)c2)CC1] | 0.13 | >4.4 |
| 66 | 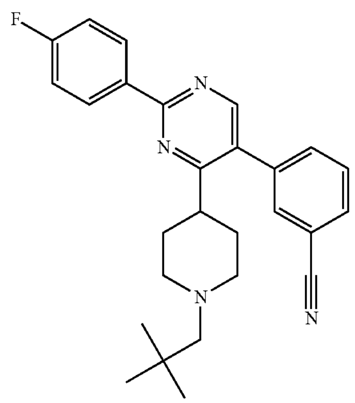 [SMILES: CC(C)(C)CN1CCC(c2nc(-c3ccc(F)cc3)ncc2-c2cccc(C#N)c2)CC1] | <0.21 | 8.8 |
| 67 | 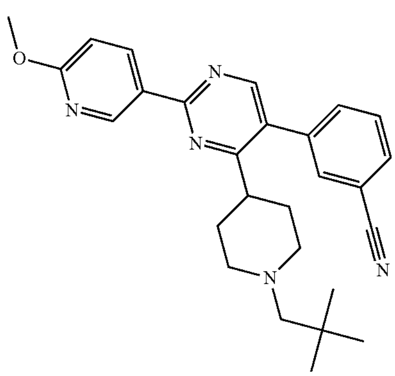 [SMILES: COc1ccc(-c2ncc(-c3cccc(C#N)c3)c(C3CCN(CC(C)(C)C)CC3)n2)cn1] | 0.81 | >11.1 |
| 68 | 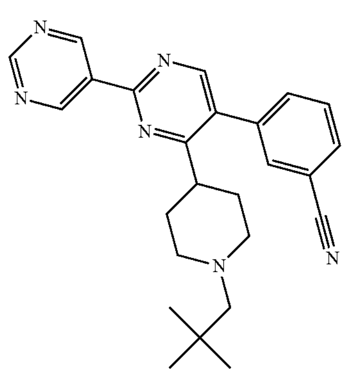 [SMILES: CC(C)(C)CN1CCC(c2nc(-c3cncnc3)ncc2-c2cccc(C#N)c2)CC1] | 6.10 | >10.4 |

TABLE 1-continued
Compounds of formula (I).
| # | STRUCTURE | IC90 (µg/ml) | CC50 (µg/ml) |
|---|---|---|---|
| 69 | 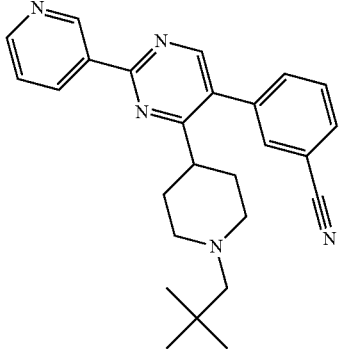 [SMILES: CC(C)(C)CN1CCC(c2nc(-c3cccnc3)ncc2-c2cccc(C#N)c2)CC1] | 3.02 | >10.3 |
| 70 | 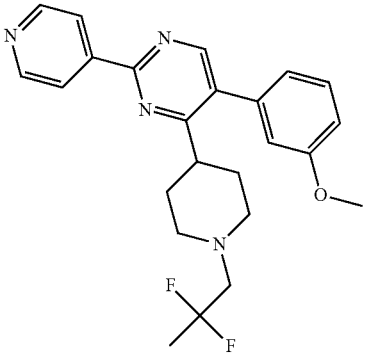 | 0.64 | 6.7 |
| 71 | 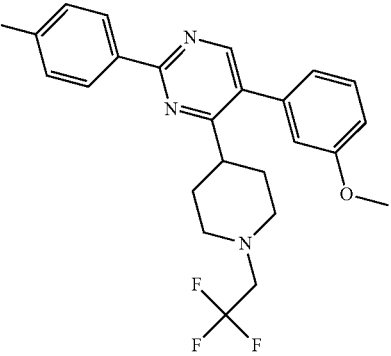 | <0.22 | |
| 72 | 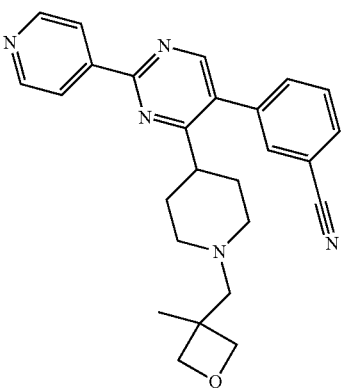 [SMILES: CC1(CN2CCC(c3nc(-c4ccncc4)ncc3-c3cccc(C#N)c3)CC2)COC1] | 25.94 | |

TABLE 2
Compounds of formula (I).
| # | STRUCTURE | MIC90 (μg/ml) |
|---|---|---|
| 73 | 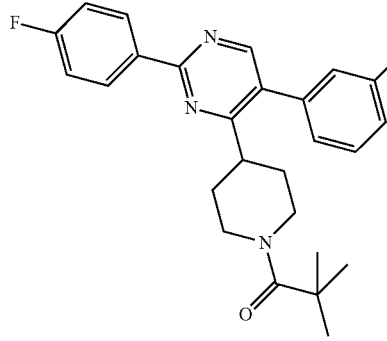 | >64 |
| 74 | 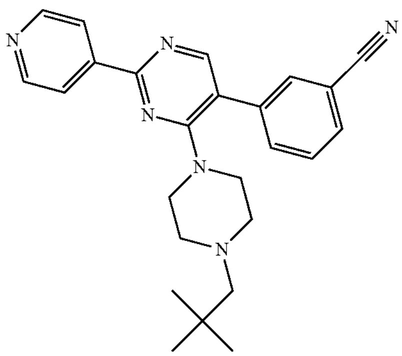 [SMILES: CC(C)(C)CN1CCN(c2nc(-c3ccncc3)ncc2-c2cccc(C#N)c2)CC1] | 0.125 |
| 75 | 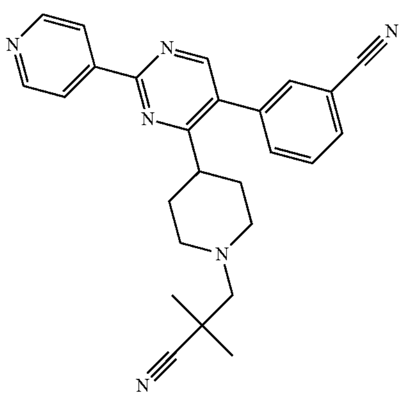 [SMILES: CC(C)(C#N)CN1CCC(c2nc(-c3ccncc3)ncc2-c2cccc(C#N)c2)CC1] | 0.5 |
| 76 | 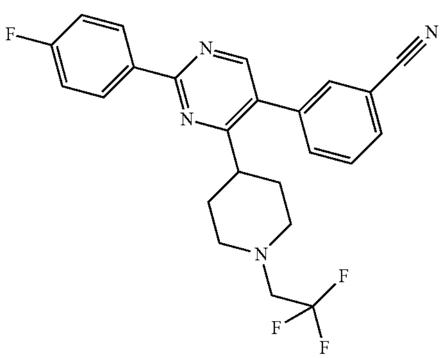 [SMILES: N#Cc1cccc(-c2cnc(-c3ccc(F)cc3)nc2C2CCN(CC(F)(F)F)CC2)c1] | 0.125 |
TABLE 2-continued
Compounds of formula (I).
| # | STRUCTURE | MIC90 (μg/ml) |
|---|---|---|
| 77 | 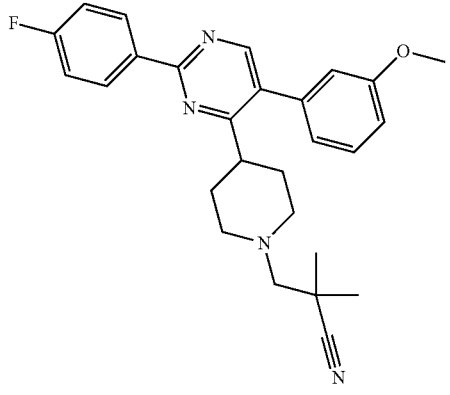 | 0.25 |
| 78 | 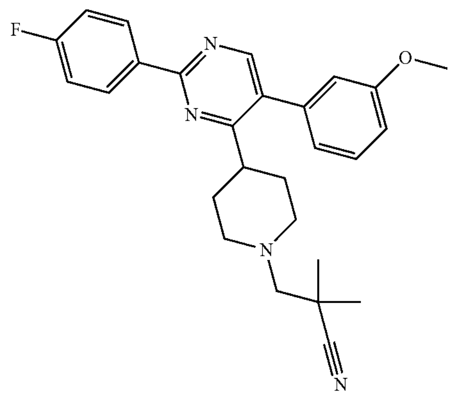 [SMILES: COc1cccc(-c2cnc(-c3ccc(F)cc3)nc2C2CCN(CC(C)(C)C#N)CC2)c1] | 0.125 |
| 79 | 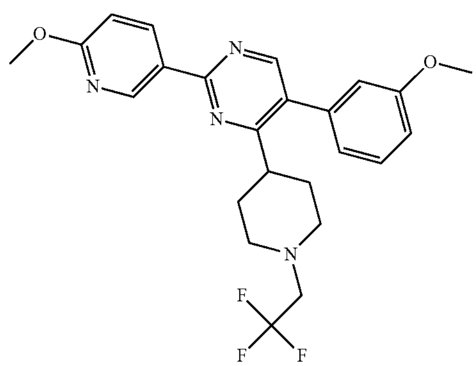 | 0.125 |
| 80 | 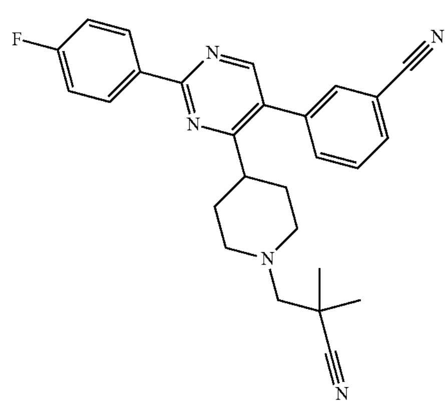 [SMILES: CC(C)(C#N)CN1CCC(c2nc(-c3ccc(F)cc3)ncc2-c2cccc(C#N)c2)CC1] | 0.125 |

TABLE 2-continued

Compounds of formula (I).

| # | STRUCTURE | MIC90 (µg/ml) |
|---|---|---|
| 81 | 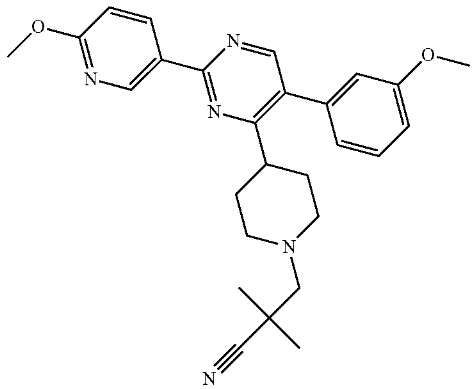 | 0.125 |
| 82 | 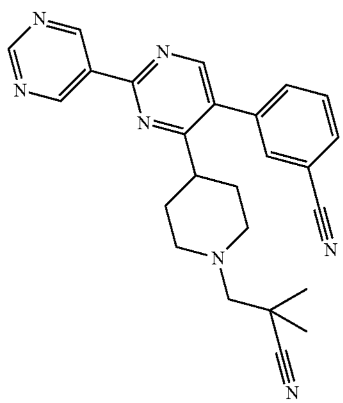 [SMILES: CC(C)(C#N)CN1CCC(c2nc(-c3cncnc3)ncc2-c2cccc(C#N)c2)CC1] | 1 |
| 83 | 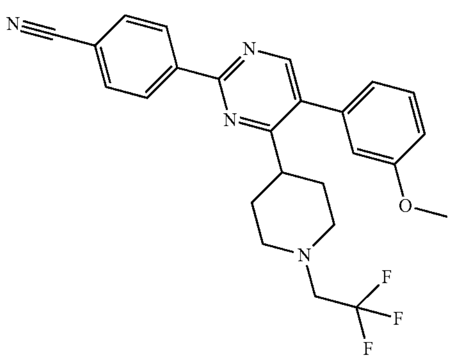 [SMILES: COc1cccc(-c2cnc(-c3ccc(C#N)cc3)nc2C2CCN(CC(F)(F)F)CC2)c1] | 0.125 |
| 84 | 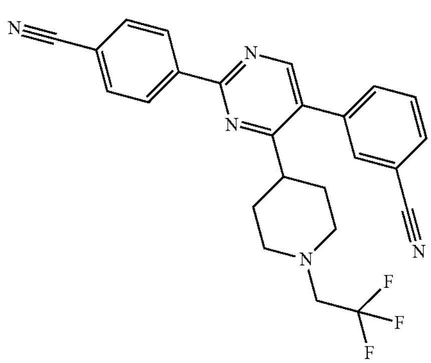 [SMILES: N#Cc1ccc(-c2ncc(-c3cccc(C#N)c3)c(C3CCN(CC(F)(F)F)CC3)n2)cc1] | 0.125 |
| 85 | | 0.125 |
| 86 | | 0.125 |
| 87 | | 2 |

TABLE 2-continued
Compounds of formula (I).
| # | STRUCTURE | MIC90 (μg/ml) |
|---|---|---|
| 88 | 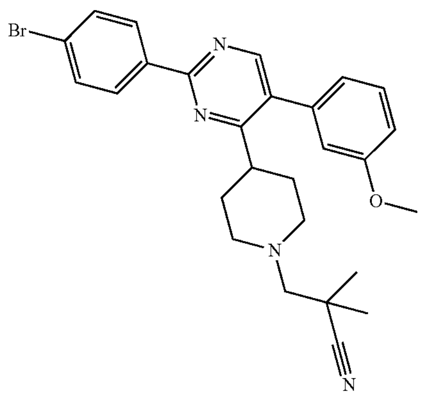 [SMILES: COc1cccc(-c2cnc(-c3ccc(Br)cc3)nc2C2CCN(CC(C)(C)C#N)CC2)c1] | 0.125 |
| 89 | 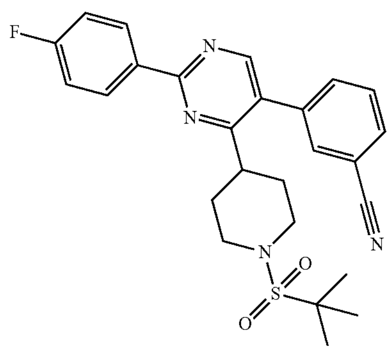 [SMILES: CC(C)(C)S(=O)(=O)N1CCC(c2nc(-c3ccc(F)cc3)ncc2-c2cccc(C#N)c2)CC1] | 0.125 |
| 90 | 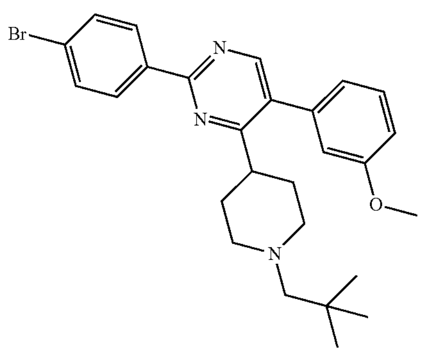 [SMILES: COc1cccc(-c2cnc(-c3ccc(Br)cc3)nc2C2CCN(CC(C)(C)C)CC2)c1] | 0.25 |
| 91 | 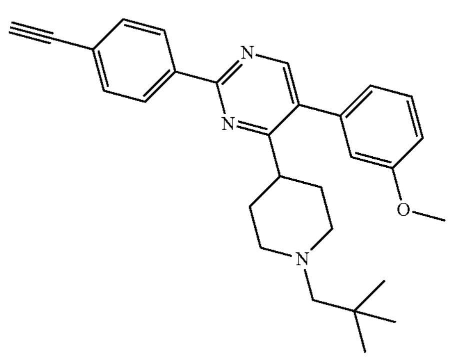 [SMILES: C#Cc1ccc(-c2ncc(-c3cccc(OC)c3)c(C3CCN(CC(C)(C)C)CC3)n2)cc1] | 0.5 |
| 92 | | 0.125 |
| 93 | | 0.125 |
The invention claimed is:
1. A compound of formula I:
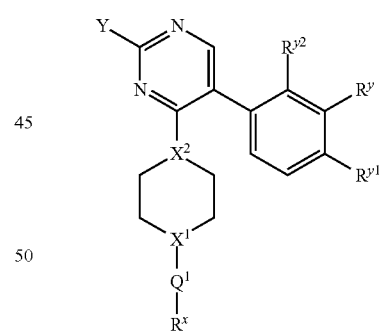
wherein:
Y represents:
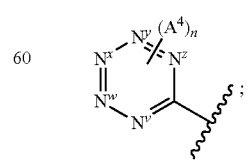
none or one of $N^v$, $N^w$, $N^x$, $N^y$ and $N^z$ (preferably one) represent(s) —N° and the others represent —C(H)=;

n represents 0 or 1;

X$^1$ represents —N—, X$^2$ is —C(H)—, and Q$^1$ represents a direct bond;

R$^z$ represents hydrogen or C$_{1-6}$ alkyl;

R$^x$ represents C$_{1-6}$ alkyl (optionally substituted by one or more substituents selected from A$^1$), aryl or heteroaryl (which latter two groups are each optionally substituted by one or more substituents selected from A$^2$ and A$^3$, respectively);

R$^y$, R$^{y1}$ and R$^{y2}$ independently represent hydrogen, halo, —CN, —OR$^{10}$, —N(R$^{11}$)(R$^{12}$) or C$_{1-6}$ alkyl (optionally substituted by one or more halo atoms);

A$^1$, A$^2$, A$^3$ and A$^4$ independently represent halo, —CN, —OR$^1$, —S(O)$_{0-2}$C$_{1-3}$alkyl, C$_{1-6}$ alkyl (optionally substituted by one or more halo substituents), heterocycloalkyl (optionally substituted by one or more substituents selected from C$_{1-3}$ alkyl and halo), aryl or heteroaryl (which latter two groups are optionally substituted by one or more substituents selected from B$^1$ and B$^2$, respectively);

each R$^1$ and R$^{10}$ independently represent hydrogen, C$_{1-6}$ alkyl (optionally substituted by one or more halo substituents), aryl or heteroaryl (which latter two groups are optionally substituted by one or more substituents selected from halo, C$_{1-3}$ alkyl and —O—C$_{1-3}$ alkyl);

R$^{11}$ and R$^{12}$ independently represent hydrogen or C$_{1-6}$ alkyl;

B$^1$ and B$^2$ independently represent halo, —CN, C$_{1-6}$ alkyl (optionally substituted by one or more halo, —OH or —O—C$_{1-6}$ alkyl (optionally substituted by one or more halo atoms), or a pharmaceutically acceptable salt thereof, with the proviso that the compound is not:

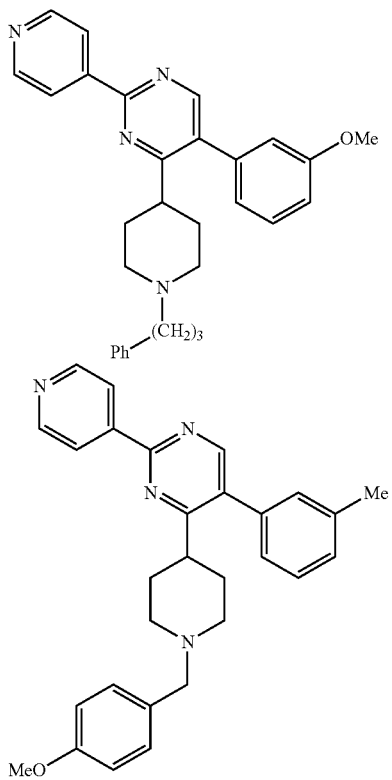

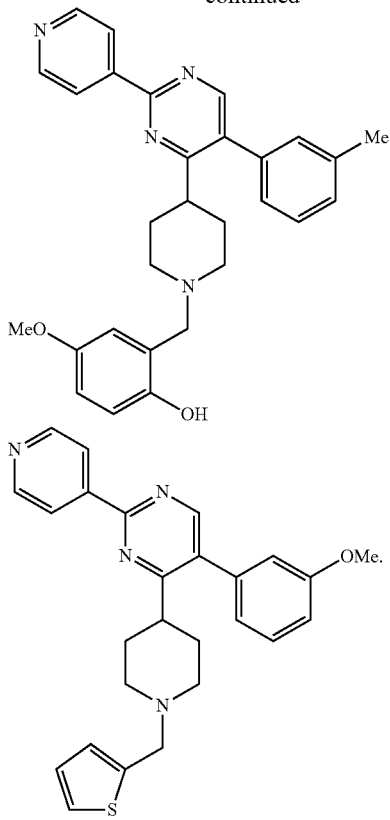

2. The compound according to claim 1 wherein:

R$^x$ represents C$_{1-6}$ alkyl (optionally substituted by one or more substituents selected from A$^1$);

A$^4$ (which is preferably present on a carbon atom of the phenyl ring, and is preferably in the para-position) represents halo, —CN or —OC$_{1-3}$ alkyl;

A$^1$ represents halo, —CN, C$_{1-6}$ alkyl or —OR$^1$;

either all of R$^y$, R$^{y1}$ and R$^{y2}$ represent hydrogen or, more preferably, at least one of R$^y$, R$^{y1}$ and R$^{y2}$ (preferably R$^y$) represents a substituent other than hydrogen and the others (preferably R$^{y1}$ and R$^{y2}$) represents hydrogen (i.e. there is preferably one substituent present on the phenyl ring, preferably in the meta-position);

when R$^y$ is other than hydrogen, it preferably represents halo, —OCH$_3$ or —CN; and/or R$^1$ represents hydrogen.

3. The compound according to claim 1 wherein the compound is:

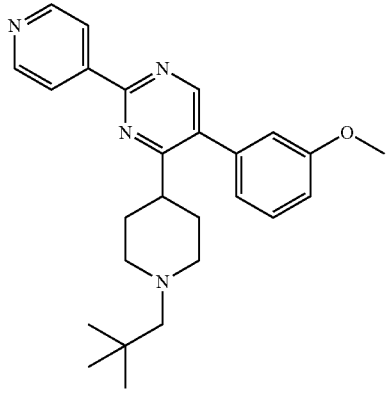

-continued
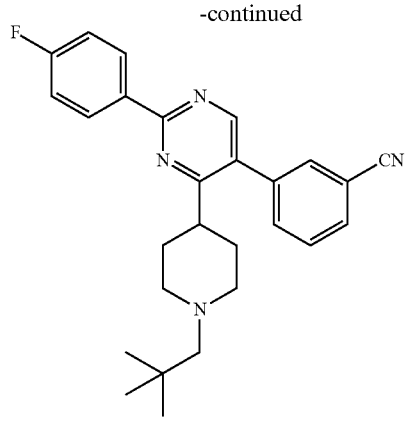
or a pharmaceutically acceptable salt thereof.
4. A combination of (a) a compound as defined in claim 1, and (b) one or more other antibacterial agents.
* * * * *